(12) United States Patent
Yokoi et al.

(10) Patent No.: US 11,344,206 B2
(45) Date of Patent: May 31, 2022

(54) ELECTRONIC DEVICE INCLUDING EARPHONE, AND METHOD OF CONTROLLING THE ELECTRONIC DEVICE

(71) Applicant: Samsung Electronics Co., Ltd., Suwon-si (KR)

(72) Inventors: Atsuya Yokoi, Yokohama (JP); Tadamasa Murakami, Yokohama (JP); Toshihiro Kitajima, Yokohama (JP); Edwardo Murakami, Yokohama (JP)

(73) Assignee: Samsung Electronics Co., Ltd., Suwon-si (KR)

( * ) Notice: Subject to any disclaimer, the term of this patent is extended or adjusted under 35 U.S.C. 154(b) by 438 days.

(21) Appl. No.: 16/713,925

(22) Filed: Dec. 13, 2019

(65) Prior Publication Data
US 2020/0187795 A1 Jun. 18, 2020

(30) Foreign Application Priority Data

Dec. 18, 2018 (JP) .............................. JP2018-236597
Feb. 20, 2019 (JP) .............................. JP2019-028415
(Continued)

(51) Int. Cl.
*A61B 5/0205* (2006.01)
*A61B 5/053* (2021.01)
(Continued)

(52) U.S. Cl.
CPC .......... *A61B 5/02055* (2013.01); *A61B 5/053* (2013.01); *A61B 5/6803* (2013.01);
(Continued)

(58) Field of Classification Search
CPC ... A61B 5/02055; A61B 5/053; A61B 5/7225; A61B 5/024; H04R 1/1016; H04R 1/1041; H04R 3/04
See application file for complete search history.

(56) References Cited

U.S. PATENT DOCUMENTS 8,199,956 B2   6/2012 Haartsen et al.
9,579,060 B1 * 2/2017 Lisy ..................... A61B 5/036
(Continued)

FOREIGN PATENT DOCUMENTS

JP   6018025 B2   11/2016
JP   6059937 B2   1/2017
(Continued)

OTHER PUBLICATIONS

International Search Report dated Apr. 28, 2020, issued in International Application No. PCT/KR2019/017812.
(Continued)

*Primary Examiner* — David L Ton
(74) *Attorney, Agent, or Firm* — Jefferson IP Law, LLP

(57) ABSTRACT

An electronic device is provided. The electronic device includes an earphone including a first impedance component, a signal generator configured to output a first alternating current (AC) signal, a first circuit including at least one first analog device having an impedance component electrically coupled to the first impedance component, and configured to receive the first AC signal and output a first detection signal including a voltage component corresponding to the first impedance component, and at least one processor configured to generate at least one piece of biometric information, based on the first detection signal, and output the at least one piece of biometric information.

20 Claims, 46 Drawing Sheets

(30) Foreign Application Priority Data

Aug. 21, 2019 (JP) ............................. JP2019-151395
Nov. 20, 2019 (KR) ........................ 10-2019-0149891

(51) Int. Cl.
| | |
|---|---|
| *A61B 5/00* | (2006.01) |
| *G06F 21/32* | (2013.01) |
| *A61B 5/024* | (2006.01) |
| *H04R 1/10* | (2006.01) |
| *H04R 3/04* | (2006.01) |
| *H03F 3/183* | (2006.01) |
| *G06F 21/31* | (2013.01) |

(52) U.S. Cl.
CPC ............ *A61B 5/7225* (2013.01); *G06F 21/31* (2013.01); *G06F 21/32* (2013.01); *H03F 3/183* (2013.01); *H04R 1/1016* (2013.01); *H04R 1/1041* (2013.01); *H04R 3/04* (2013.01); *A61B 5/024* (2013.01); *H03F 2200/03* (2013.01); *H03F 2200/102* (2013.01)

(56) References Cited

U.S. PATENT DOCUMENTS

| | | | |
|---|---|---|---|
| 9,973,870 B2 | 5/2018 | Ben-Ami et al. | |
| 11,298,064 B1* | 4/2022 | Lisy | A61B 5/282 |
| 2007/0297634 A1 | 12/2007 | Hansson | |
| 2014/0051939 A1* | 2/2014 | Messerschmidt | A61B 5/0205 |
| | | | 600/587 |
| 2014/0140567 A1* | 5/2014 | LeBoeuf | A61B 5/01 |
| | | | 381/381 |
| 2016/0166203 A1 | 6/2016 | Goldstein | |
| 2016/0324478 A1* | 11/2016 | Goldstein | A61B 5/1172 |
| 2017/0142521 A1* | 5/2017 | Xu | H04R 5/04 |
| 2018/0063621 A1 | 3/2018 | Qian et al. | |
| 2018/0139528 A1 | 5/2018 | Wen | |
| 2019/0380597 A1* | 12/2019 | Howard | A61B 5/318 |

FOREIGN PATENT DOCUMENTS

| | | |
|---|---|---|
| KR | 10-2012-0051898 A | 5/2012 |
| KR | 10-1439332 B1 | 9/2014 |
| WO | 2017/048476 A1 | 3/2017 |
| WO | 2018/071630 A1 | 4/2018 |

OTHER PUBLICATIONS

Vance Dickason Daniel R. Raichel, The Loudspeaker Design Cookbook, 5th Edition, Oct. 28, 1999 https://asa.scitation.org/doi/abs/10.1121/1.428228?journalCode=jas.

Engineering Acoustics/Moving Coil Loudspeaker https://en.wikibooks.org/wiki/Engineering_Acoustics/Moving_Coil_Loudspeaker.

Kurten Ihlenfeld W G et al., A Digital Quadrature Bridge for Impedance Measurements, 29th Conference on Precision Electromagnetic Measurements (CPEM 2014), IEEE, pp. 106-107, Aug. 24, 2014, XP032653066.

European Search Report dated Dec. 9, 2021, issued in European Application No. 19897771.2.

\* cited by examiner

ELECTRONIC DEVICE INCLUDING EARPHONE, AND METHOD OF CONTROLLING THE ELECTRONIC DEVICE

CROSS-REFERENCE TO RELATED APPLICATION(S)

This application is based on and claims priority under 35 U.S.C. § 119(a) of a Japanese patent application number 2018-236597, filed on Dec. 18, 2018, in the Japanese Intellectual Property Office, of a Japanese patent application number 2019-028415, filed on Feb. 20, 2019, in the Japanese Intellectual Property Office, and of a Japanese patent application number 2019-151395, filed on Aug. 21, 2019, in the Japanese Intellectual Property Office, and of a Korean patent application number 10-2019-0149891, filed on Nov. 20, 2019, in the Korean Intellectual Property Office, the disclosure of each of which is incorporated by reference herein in its entirety.

BACKGROUND

1. Field

The disclosure relates to an electronic device including an earphone, and a method of controlling the electronic device.

2. Description of Related Art

In case of electronic devices, various technologies for obtaining biometric information are under development. Electronic devices can monitor a body state of a user by using biometric information and provide various pieces of health information based on the biometric information. The biometric information can also be used for various purposes, such as user authentication and device control. However, a user may have to perform a special action to collect biometric information, or may have to make a part of his or her body in contact with a certain location on an electronic device. This may be burdensome to the user. Moreover, a factor, such as a surrounding environment makes it difficult to collect accurate biometric information.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide a device and a method of obtaining biometric information by using an earphone, so that a user is able to obtain the biometric information without performing a special action for obtaining the biometric information.

Another aspect of the disclosure is to provide a device and a method of obtaining biometric information by using an earphone while outputting audio through the earphone.

Additional aspects will be set forth in part in the description which follows and, in part, will be apparent from the description, or may be learned by practice of the presented embodiments of the disclosure.

In accordance with an aspect of the disclosure, an electronic device is provided. The electronic device includes an earphone including a first impedance component, a signal generator configured to output a first alternating current (AC) signal, a first circuit including at least one first analog device having an impedance component electrically coupled to the first impedance component, and configured to receive the first AC signal and output a first detection signal including a voltage component corresponding to the first impedance component, and at least one processor configured to generate at least one piece of biometric information, based on the first detection signal, and output the at least one piece of biometric information.

The electronic device may include a shape in which the earphone is inserted into the external auditory meatus of a human being, and a magnitude of the first impedance component may vary according to a change in the pressure of the external auditory meatus.

The at least one piece of biometric information may include heart rate information, and the at least one processor may generate the heart rate information, based on a phase component of the first detection signal.

The at least one piece of biometric information may include body temperature information, and the at least one processor may generate the body temperature information, based on an amplitude component of the first detection signal.

The first AC signal may include a frequency in an ultrasonic range.

The first AC signal may include a frequency of 20 kilohertz (kHz) to 40 kHz.

The first circuit may be configured to generate the first detection signal including an in-phase signal of an in-phase component and an orthogonal signal of a quadrature phase component from the first AC signal and an intermediate detection signal of a node connected to the first analog device, and output the first detection signal to the at least one processor.

The at least one processor may be configured to generate body temperature information, based on a sum of a square of the in-phase signal and a square of the orthogonal signal, and generate heart rate information, based on phase information extracted from the in-phase signal and the orthogonal signal.

The first device may include a second impedance device, a third impedance device, and a fourth impedance device connected with the first impedance component in a bridge circuit structure, and may be configured to receive the first AC signal via at least one of a first node or a second node of the bridge circuit structure or a combination thereof, generate an in-phase signal of an in-phase component and an orthogonal signal of a quadrature phase component from an intermediate detection signal of a third node of the bridge circuit structure, and output the in-phase signal and the orthogonal signal to the at least one processor.

Two impedance devices directly connected to the first node may have identical impedance values, and two impedance devices directly connected to the second node may have identical impedance values.

The first node may receive the first AC signal, the second node may receive a signal obtained by delaying the phase of the first AC signal by 180°, the first impedance component may be connected between a fourth node and the first node, and the fourth node may be connected to ground potential.

The first node may receive the first AC signal, the second node may be connected to ground potential, the first impedance component may be connected to between the second node and a fourth node, and the first circuit may be configured to differentially amplify a signal of the fourth node and a signal of the third node to generate the first detection signal.

The first impedance component may be connected to between the second node and a fourth node, the second impedance device may be connected to between the first node and the fourth node, the third impedance device may be connected to between the first node and the third node, and the fourth impedance device may be connected to between the second node and the third node. The earphone may include a first resistance component and a first inductance component, the second impedance device may include a second resistor, the third impedance device may include a third resistor and a third capacitor connected to the third resistor in parallel, and the fourth impedance device may include a fourth resistor. The first resistance component and a resistance component of the fourth resistor may include same magnitudes, the second resistor and the third resistor may include resistance components of which magnitudes are same, and the third capacitor may include a capacitor component of a magnitude {first inductance component/(resistance component of third resistor*resistance component of fourth resistor)}.

The first impedance component may be connected to between the second node and a fourth node.

The second impedance device may be connected to between the first node and the fourth node, the third impedance device may be connected to between the first node and the third node, and the fourth impedance device may be connected to between the second node and the third node.

The first impedance component may include a first first resistance component and a first inductance component serially connected to each other between the second node and the fourth node, and a second first resistance component connected to the first first resistance component and the first inductance component in parallel between the second node and the fourth node, the second impedance device may include a second resistor, the third impedance device may include a third resistor and a third capacitor connected to each other in parallel between the first node and the third node, and the fourth impedance device may include a first fourth resistor, a second fourth resistor, and a fourth capacitor connected to one another in parallel between the second node and the third node.

The first first resistance component and a resistance component of the first fourth resistor may include same magnitudes, the second resistor and the third resistor may include resistance components of which magnitudes are same, and the second first resistance component and a resistance component of the second fourth resistor may include same magnitudes. The third capacitor may include a capacitor component of a magnitude {first inductance component/(resistance component of third resistor*resistance component of first fourth resistor)}.

The first circuit may include a band pass filter and an envelope detector, and may be configured to generate a second intermediate detection signal by modulating a first intermediate detection signal of a node connected to the first analog device by using the band pass filter and the envelope detector and to generate the first detection signal including an amplitude change component signal and a direct current (DC) component signal generated from the second intermediate detection signal. The at least one processor may be configured to generate heart rate information from the amplitude change component signal and generate body temperature information from the DC component signal.

The first circuit may be configured to receive an electrical audio signal corresponding to an audio signal output via the earphone, process the electrical audio signal by using a high pass filter, and apply a result of the processing to at least one node of the first circuit.

The first circuit may be configured to generate the first detection signal including an in-phase signal of an in-phase component and an orthogonal signal of a quadrature phase component from the first AC signal and an intermediate detection signal of a node connected to the first analog device. The at least one processor may be configured to generate an amplitude signal of an amplitude component and a phase signal of a phase component from the in-phase signal and the orthogonal signal and remove a motion component of the electronic device by using the amplitude signal and the phase signal.

The first circuit may be configured to generate the first detection signal including an in-phase signal of an in-phase component and an orthogonal signal of a quadrature phase component from the first AC signal and an intermediate detection signal of a node connected to the first analog device. The at least one processor may be configured to generate an amplitude signal of an amplitude component and a phase signal of a phase component from the in-phase signal and the orthogonal signal, and to detect attachment or detachment of the electronic device, based on a variation in at least one of the amplitude signal or the phase signal.

In accordance with another aspect of the disclosure, a method of controlling an electronic device is provided. The method includes an earphone including a first impedance component, and a first circuit including at least one first analog device including an impedance component electrically coupled to the first impedance component, includes the operations of controlling a first AC signal to be output to the first circuit, obtaining a first detection signal including a voltage component corresponding to the first impedance component from the first circuit, generating at least one piece of biometric information, based on the first detection signal, and outputting the at least one piece of biometric information.

The electronic device may include a shape in which the earphone is inserted into the external auditory meatus of a human being, and a magnitude of the first impedance component may vary according to a change in the pressure of the external auditory meatus.

The at least one piece of biometric information may include heart rate information, and the method may include generating the heart rate information, based on a phase component of the first detection signal.

The at least one piece of biometric information may include body temperature information, and the method may include generating the body temperature information, based on an amplitude component of the first detection signal.

The first AC signal may include a frequency in an ultrasonic range.

The first AC signal may include a frequency of 20 kHz to 40 kHz.

The method may further include generating the first detection signal including an in-phase signal of an in-phase component and an orthogonal signal of a quadrature phase component from the first AC signal and an intermediate detection signal of a node connected to the first analog device, wherein the generation is performed by the first circuit.

The method may further include generating body temperature information, based on a sum of a square of the in-phase signal and a square of the orthogonal signal, and generating heart rate information, based on phase information extracted from the in-phase signal and the orthogonal signal.

The first circuit may include a second impedance device, a third impedance device, and a fourth impedance device connected with the first impedance component in a bridge circuit structure, and the method may further include receiving the first AC signal via at least one of a first node or a second node of the bridge circuit structure or a combination thereof, generating an in-phase signal of an in-phase component and an orthogonal signal of a quadrature phase component from an intermediate detection signal of a third node of the bridge circuit structure, and outputting the in-phase signal and the orthogonal signal.

Two impedance devices directly connected to the first node may have identical impedance values, and two impedance devices directly connected to the second node may have identical impedance values.

The method may further include receiving the first AC signal by the first node and receiving, by the second node, a signal obtained by delaying the phase of the first AC signal by 180°, the first impedance component may be connected between a fourth node and the first node, and the fourth node may be connected to ground potential.

The first node may receive the first AC signal, the second node may be connected to ground potential, the first impedance component may be connected to between the second node and a fourth node, and the method may further include differentially amplifying a signal of the fourth node and a signal of the third node to generate the first detection signal, wherein the differentially amplifying is performed by the first circuit.

The first impedance component may be connected to between the second node and a fourth node, the second impedance device may be connected to between the first node and the fourth node, the third impedance device may be connected to between the first node and the third node, and the fourth impedance device may be connected to between the second node and the third node. The earphone may include a first resistance component and a first inductance component, the second impedance device may include a second resistor, the third impedance device may include a third resistor and a third capacitor connected to the third resistor in parallel, and the fourth impedance device may include a fourth resistor. The first resistance component and a resistance component of the fourth resistor may include same magnitudes, the second resistor and the third resistor may include resistance components of which magnitudes are same, and the third capacitor may include a capacitor component of a magnitude {first inductance component/(resistance component of third resistor*resistance component of fourth resistor)}.

The first impedance component may be connected to between the second node and a fourth node, the second impedance device may be connected to between the first node and the fourth node, the third impedance device may be connected to between the first node and the third node, and the fourth impedance device may be connected to between the second node and the third node. The first impedance component may include a first first resistance component and a first inductance component serially connected to each other between the second node and the fourth node, and a second first resistance component connected to the first first resistance component and the first inductance component in parallel between the second node and the fourth node, the second impedance device may include a second resistor, the third impedance device may include a third resistor and a third capacitor connected to each other in parallel between the first node and the third node, and the fourth impedance device may include a first fourth resistor, a second fourth resistor, and a fourth capacitor connected to one another in parallel between the second node and the third node.

The first first resistance component and a resistance component of the first fourth resistor may include same magnitudes, the second resistor and the third resistor may include resistance components of which magnitudes are same, and the second first resistance component and a resistance component of the second fourth resistor may include same magnitudes. The third capacitor may include a capacitor component of a magnitude {first inductance component/(resistance component of third resistor*resistance component of first fourth resistor)}.

The first circuit may include a band pass filter and an envelope detector, and the method may further include generating a second intermediate detection signal by modulating a first intermediate detection signal of a node connected to the first analog device by using the band pass filter and the envelope detector, generating the first detection signal including an amplitude change component signal and a direct current (DC) component signal generated from the second intermediate detection signal, generating heart rate information from the amplitude change component signal, and generating body temperature information from the DC component signal.

The method may further include receiving an electrical audio signal corresponding to an audio signal output via the earphone, and processing the electrical audio signal by using a high pass filter and then applying a result of the processing to at least one node of the first circuit.

The method may further include generating the first detection signal including an in-phase signal of an in-phase component and an orthogonal signal of a quadrature phase component from the first AC signal and an intermediate detection signal of a node connected to the first analog device, generating an amplitude signal of an amplitude component and a phase signal of a phase component from the in-phase signal and the orthogonal signal, and removing a motion component of the electronic device by using the amplitude signal and the phase signal, wherein these operations are performed by the first circuit.

The method may further include generating the first detection signal including an in-phase signal of an in-phase component and an orthogonal signal of a quadrature phase component from the first AC signal and an intermediate detection signal of a node connected to the first analog device, generating an amplitude signal of an amplitude component and a phase signal of a phase component from the in-phase signal and the orthogonal signal, and detecting attachment or detachment of the electronic device, based on a variation in at least one of the amplitude signal or the phase signal, wherein these operations are performed by the first circuit.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
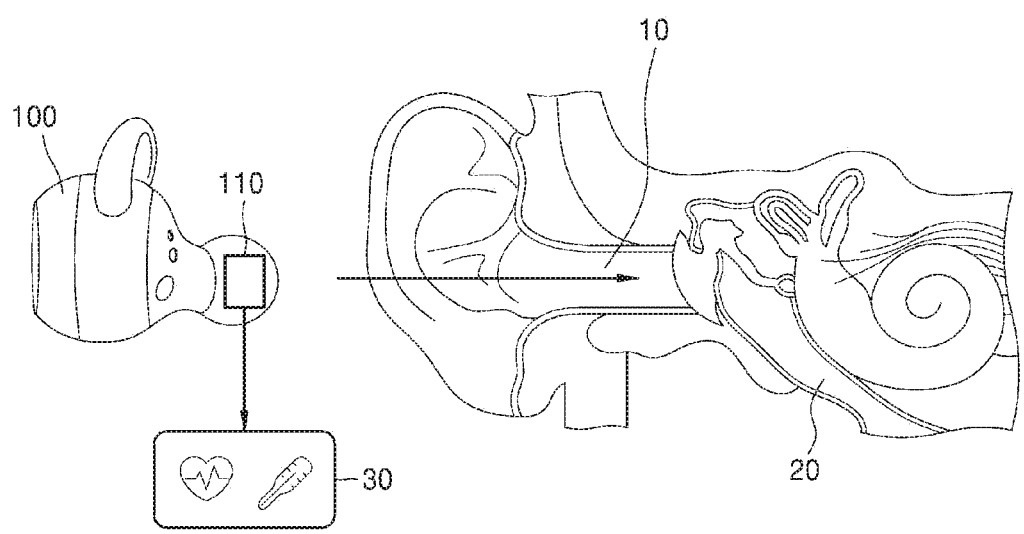
FIG. 1 illustrates a structure of an electronic device and an ear structure of a human being according to an embodiment of the disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Throughout the specification, like reference numerals or characters refer to like elements. In the specification, all elements of embodiments are not explained, but general matters in the technical field of the disclosure or redundant matters between embodiments will not be described. The term "module" or "unit" used herein may be implemented as one or more of software, hardware, or firmware. According to embodiments of the disclosure, a plurality of "modules" or "units" may be implemented as one element, or one "module" or "unit" may include a plurality of elements.

Throughout the disclosure, the expression "at least one of a, b or c" indicates only a, only b, only c, both a and b, both a and c, both b and c, all of a, b, and c, or variations thereof.

In the description of embodiments of the disclosure, certain detailed explanations of the related art are omitted when it is deemed that they may unnecessarily obscure the essence of the disclosure. While such terms as "first," "second," etc., may be used to describe various components, such components must not be limited to the above terms. The above terms are used only to distinguish one component from another.

When an element (e.g., a first element) is "coupled to" or "connected to" another element (e.g., a second element), the first element may be directly coupled to or connected to the second element, or, unless otherwise described, a third element may exist therebetween.

In the disclosure, blocks and various processing blocks within processors 140, 140a, 140b, 140c, 140d, 140e, and 140f may correspond to at least one software processing block, at least one dedicated hardware processor, and a combination thereof. The blocks defined within the processors 140, 140a, 140b, 140c, 140d, 140e, and 140f in the disclosure are merely examples of software processing units for performing embodiments of the disclosure. Other than the processing units disclosed in the disclosure, processing units that perform embodiments of the disclosure in various ways may be defined.

The operational principles of embodiments of the disclosure and various embodiments of the disclosure will now be described more fully with reference to the accompanying drawings.

FIG. 1 illustrates a structure of an electronic device and an ear structure of a human being according to an embodiment of the disclosure.

Referring to FIG. 1, an electronic device 100 according to embodiments of the disclosure is implemented in a type including an earphone 110. The electronic device 100 may be implemented as, for example, a wearable device including the earphone 110. The electronic device 100 may be implemented as, for example, a wireless earphone, a wired earphone, a head mount display, or smart glasses. The electronic device 100 has a shape that is inserted into an external auditory meatus 10 of the ear of a human being. The electronic device 100 may obtain various pieces of biometric information 30 by using the earphone 110 and a first circuit electrically coupled to the impedance component of the earphone 110.

The biometric information 30 is related to the body of a user who is wearing the electronic device 100. The biometric information 30 may be obtained via an interaction between the body of the user and the electronic device 100. The biometric information 30 may include, for example, at least one of a heart rate or a body temperature, or a combination thereof.

The electronic device 100 according to embodiments of the disclosure detects the biometric information of a wearer (examinee) of the earphone 110 by measuring a change in the impedance of the earphone 110. The earphone 110 is connected to the first circuit according to embodiments of the disclosure. The earphone 110 may be implemented such that it has a first impedance component and the first impedance component and the first circuit constitute a voltage distribution circuit. Specifically, an equivalent circuit of the earphone 110 includes an electrical circuit, a mechanical circuit, and an acoustical circuit, and the electrical circuit, the mechanical circuit, and the acoustical circuit interacts with one another.

When the earphone 110 is mounted on the external auditory meatus 10 of the examinee, the pressure in an auditory tube 20 is changed by pulsation within the body. Thus, an acoustic impedance of the acoustical circuit of the earphone 110 changes, and thus the impedance of the electrical circuit changes. Thus, according to embodiments of the disclosure, a change in the impedance of the electrical circuit is detected by inputting, as a driving signal voltage, an alternating current (AC) signal having a certain frequency to the electrical circuit of the earphone 110 and measuring a current generated in the electrical circuit of the earphone 110.

When the temperature of the entire earphone 110 is changed due to a change in the body temperature, a resistance value of the impedance of the electrical circuit changes. Thus, according to embodiments of the disclosure, a change in the body temperature of the examinee is detected by measuring an averaged change, over time, in the impedance of the electrical circuit of the earphone 110 attached to the ear of the examinee due to pulsation, and converting the change, over time, in the impedance of the earphone 110 into a change, over time, in the body temperature of the examinee.

According to embodiments of the disclosure, the biometric information may be detected noninvasively. According to embodiments of the disclosure, the biometric information may be collected when a user simply inserts the electronic device 100 into the external auditory meatus 10. Because the user inserts the electronic device 100 into the external auditory meatus 10 when necessary, the user does not need to perform a special action to collect the biometric information. Thus, according to embodiments of the disclosure, the biometric information may be detected noninvasively without requiring a user to perform an additional action.

Figure 2:
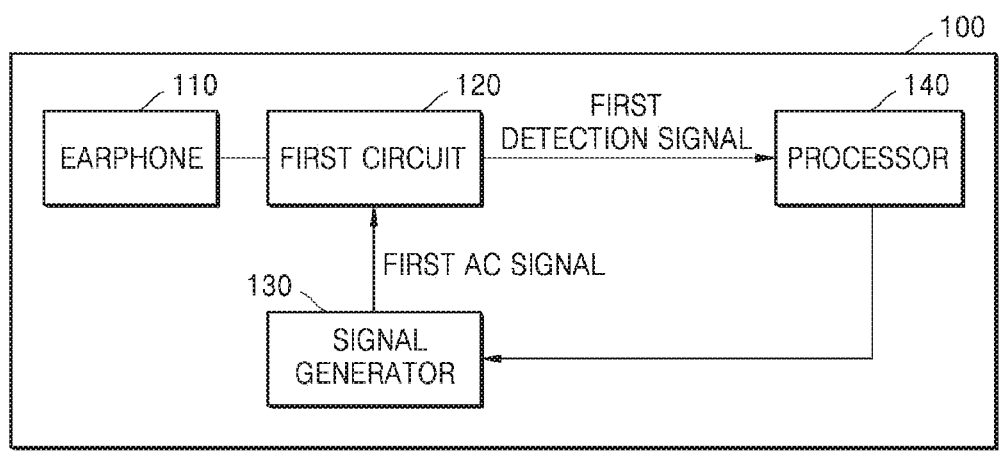
FIG. 2 is a block diagram of an electronic device according to an embodiment of the disclosure.

FIG. 2 is a block diagram of an electronic device according to an embodiment of the disclosure.

Referring to FIG. 2, the electronic device 100 according to an embodiment of the disclosure may include the earphone 110, a first circuit 120, a signal generator 130, and a processor 140.

The earphone 110 transforms an electrical signal into a sound wave signal and outputs the sound wave signal. The earphone 110 may transform the electrical signal into the sound wave signal by operating a vibration plate. The earphone 110 may be referred to as an earphone receiver. For example, the earphone 110 may be implemented as, for example, a crystal receiver or a magnetic receiver. The crystal receiver operates a vibration plate by using a piezoelectric effect of a crystal device, and the magnetic receiver operates a vibration plate by flowing a current corresponding to an audio signal into a coil.

The earphone 110 according to an embodiment of the disclosure may include a first impedance component. The first impedance component represents a sum of impedance components that are generated by an analog device, electric wires, and the like included in the earphone 110. The first impedance component may be represented by a resistance component and an inductance component.

The first circuit 120 includes at least one first analog device and is electrically coupled to the first impedance component of the earphone 110. The first analog device may include at least one of a resistor, an inductor, or a capacitor, or a combination thereof. The first analog device may have an impedance component. According to an embodiment of the disclosure, the first circuit 120 may include a plurality of first analog devices, and the plurality of first analog devices may be connected to each other in series or in parallel to constitute various circuit structures. The first analog device is electrically coupled to the first impedance component of the earphone 110, thereby constituting a resistance division circuit in which separate voltages are respectively applied to the first analog device and the first impedance component. The first circuit 120 may receive a first AC signal from the signal generator 130 via a certain node. In the first circuit 120, the voltage of the first AC signal may be divided between the first impedance component and the first analog device. At this time, the voltage of the first AC signal may be divided according to a ratio between the impedance component of the first analog device and the first impedance component, and thus voltages obtained by the division may be applied to the first analog device and the first impedance component, respectively.

The first circuit 120 outputs a first detection signal including a voltage component corresponding to the first impedance component. The first impedance component of the earphone 110 may be changed by a bio-signal. For example, a pulse wave signal due to a heartbeat may be transmitted to the vibration plate of the earphone 110, and thus the first impedance component may change in connection with the pulse wave signal. As another example, the first impedance component of the earphone 110 may be changed by the body temperature. The first circuit 120 is electrically coupled to the first impedance component and outputs a first detection signal associated with the magnitude of the first impedance component. As the first impedance component is changed by the bio-signal, the value of the first detection signal also changes in correspondence with a variation in the first impedance component. Accordingly, the processor 140 may obtain biometric information by detecting the variation in the first impedance component from the first detection signal.

The first circuit 120 includes an analog-to-digital converter (ADC), and performs analog-to-digital conversion on a detection signal of the first circuit 120 to generate the first detection signal having a digital form and output the first detection signal to the processor 140.

The first circuit 120 may be electrically coupled to the electrical circuit of the earphone 110 and provided on a substrate. The first circuit 120 may be implemented as, for example, a printed circuit board (PCB) or a flexible printed circuit board (FPCB).

The signal generator 130 generates a first AC signal having a first frequency. For example, the signal generator 130 may generate the first AC signal having the first frequency by using a frequency modulation circuit, a voltage division circuit, and the like.

According to an embodiment of the disclosure, the first frequency, which is a frequency within an ultrasonic range, may correspond to a frequency range that exceeds about 20 kHz. According to embodiments of the disclosure, noise due to the first AC signal may be prevented from being output to the earphone 110, by using a frequency signal within the ultrasonic range that exceeds an audible maximum limit range that is audible to human beings.

According to an embodiment of the disclosure, the first frequency may be 20 kHz to 40 kHz. The first circuit 120 converts a certain signal by using the ADC. A signal within the first circuit 120 has the first frequency of the first AC signal. However, during analog-to-digital conversion, signal sampling needs to be performed at a frequency that is two or more times the first frequency. When the first frequency is a frequency that exceeds 40 kHz, it is difficult to implement the ADC. Thus, according to an embodiment of the disclosure, the first frequency may be set to be 40 Hz or less, and accordingly the first circuit 120 may be easily configured.

The processor 140 controls all operations of the electronic device 100. The processor 140 may include at least one processor 140. The processor 140 may perform a certain operation by executing an instruction or command stored in a memory (not shown). The processor 140 may control outputting or non-outputting of the first AC signal by the signal generator 130, the intensity of the first AC signal, the frequency of the first AC signal, and the like.

The processor 140 receives the first detection signal from the first circuit 120 and generates at least one piece of biometric information. The first detection signal may have a magnitude component and a phase component, and the magnitude component and the phase component of the first detection signal may change according to a bio-signal. The processor 140 may extract the magnitude component and the phase component from the first detection signal to obtain biometric information. For example, the processor 140 may obtain body temperature information from the magnitude component of the first detection signal, and may obtain heart rate information from the phase component of the first detection signal.

According to an embodiment of the disclosure, the electronic device 100 may further include an output interface (not shown). The output interface outputs the biometric information generated by the processor 140. The output interface may correspond to, for example, a display or a communication interface.

According to an embodiment of the disclosure, the output interface may correspond to a communication interface, and the electronic device 100 may transmit the biometric information to an external device via the output interface. For example, the electronic device 100 may transmit the biometric information to a smailphone, which is a main device, while communicating with the smailphone. As another example, the electronic device 100 may transmit the biometric information to an external server while communicating with the external server.

According to an embodiment of the disclosure, the electronic device 100 may output the biometric information via the earphone 110. The processor 140 may convert the biometric information into audio data and output the biometric information via the earphone 110. For example, the processor 140 may generate heart rate information, heart rate abnormality information, body temperature information, and body temperature abnormality information and output the same to the earphone 110.

According to an embodiment of the disclosure, the output interface may correspond to a display, and the electronic device 100 may output the biometric information via the output interface. When the electronic device 100 is implemented as, for example, a head mount display or smart glasses, the processor 140 may generate biometric information or bio-signal abnormality information as visual information and output the biometric information or the bio-signal abnormality information via a graphical user interface (GUI).

Figure 3:
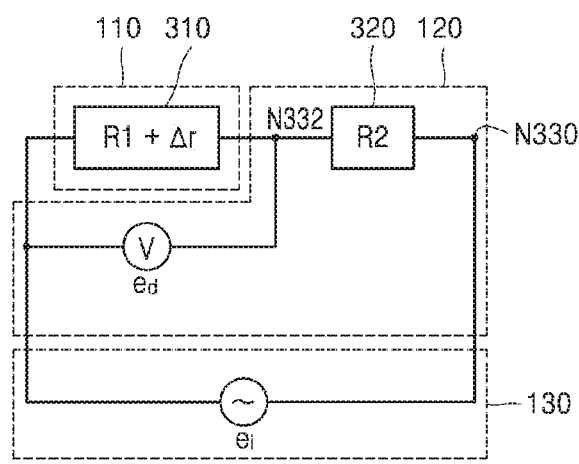
FIG. 3 illustrates an equivalent circuit of a first impedance component, a first circuit, and a signal generator according to an embodiment of the disclosure.

FIG. 3 illustrates an equivalent circuit of a first impedance component, a first circuit, and a signal generator according to an embodiment of the disclosure.

Referring to FIG. 3, the earphone 110 includes a first impedance component 310. The first impedance component 310 may have a resistance R1 and an impedance variation component Δr. The impedance variation Δr may be generated according to the bio-signal.

The first circuit 120 includes at least one first analog device 320. The first analog device 320 may include an impedance component. For example, the first analog device 320 may include a resistance component R2. The first analog device 320 may include one or more analog devices, and may have an impedance component that originates from the one or more analog devices.

The signal generator 130 may generate and output a first AC signal ei having a first frequency. The first AC signal ei has an AC voltage having a certain amplitude. The first AC signal ei may be input to a first node N330 of the first circuit 120. The signal generator 130 may also generate a first AC signal that vibrates about a certain ground potential, and an end of the first impedance component 310 may be connected to the certain ground potential. In other words, an end of the signal generator 130 and the end of the first impedance component 310 may have an electrically identical potential and accordingly may correspond to electrically identical nodes. The other end of the first impedance component 310 may be serially coupled to the first analog device 320. Accordingly, the voltage of the first AC signal ei may be applied to both ends of a circuit where the first impedance component 310 and the first analog device 320 are serially coupled with each other.

The first impedance component 310 and the first analog device 320 constitute a voltage division circuit. Accordingly, as a voltage applied to both ends of the voltage division circuit is divided, a second node N332 between the first impedance component 310 and the first analog device 320 has a voltage ed corresponding to the first impedance component 310 based on the certain ground potential. Because the electronic device 100 detects a voltage of the second node N332, the electronic device 100 may detect the first impedance component 310 and may detect the impedance variation Δr.

Figure 4:
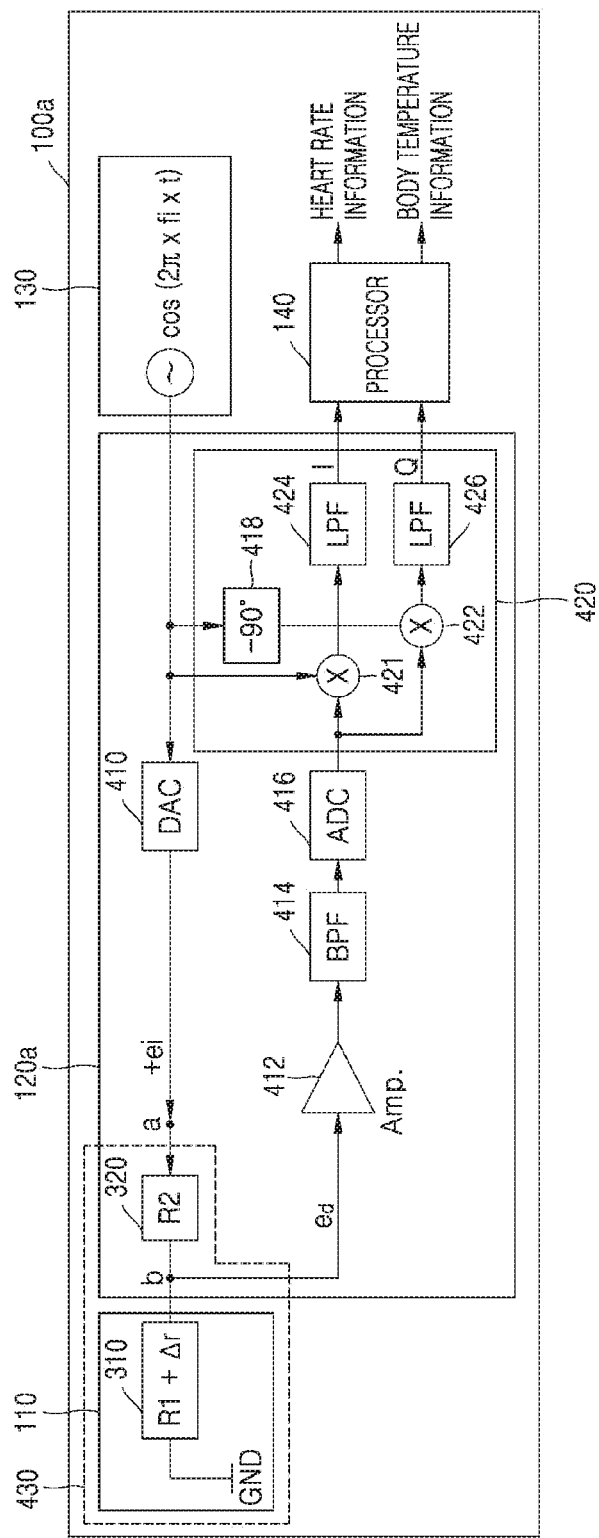
FIG. 4 is a block diagram of an electronic device according to an embodiment of the disclosure.

FIG. 4 is a block diagram of an electronic device according to an embodiment of the disclosure.

Referring to FIG. 4, an electronic device 100*a* includes the earphone 110, a first circuit 120*a*, the signal generator 130, and the processor 140. The first circuit 120*a* includes a digital-to-analog converter (DAC) 410, the first analog device 320, an amplifier (Amp.) 412, a band pass filter (BPF) 414, an ADC 416, and an orthogonal demodulator 420. The electronic device 100*a* according to an embodiment of the disclosure also includes an analog circuit 430 including the first analog device 320 and the first impedance component 310 of the earphone 110. The first analog device 320 has a fixed impedance component. The first analog device 320 is a circuit including at least one of a fixed resistor, a fixed inductor, or a fixed capacitor, or a combination thereof The signal generator 130 generates, as a driving signal voltage that is input to the electrical circuit of the earphone 110, an AC signal cos(2π×fi×t) having a predetermined frequency fi, where t indicates time (second). The AC signal cos(2π×fi×t) generated by the signal generator 130 is input to the analog circuit 430 via the DAC 410.

The predetermined frequency fi may be a frequency of 20 kHz or greater. When the predetermined frequency fi is 20 kHz or greater, because sound having the predetermined frequency fi is generally ultrasound inaudible to human beings, the electronic device 100*a* may detect biometric information without destroying an audio providing function of the earphone 110. The predetermined frequency fi may be 40 kHz or less. Because a sampling frequency of the ADC 416 to be described later needs to be twice or more the predetermined frequency fi, when the predetermined frequency fi is a frequency exceeding 40 kHz, it is difficult to realize the ADC 416 having a sampling frequency that is twice the predetermined frequency fi.

The DAC 410 performs digital-analog conversion on the AC signal generated by the signal generator 130, and inputs a result of the digital-analog conversion to the analog circuit 430.

Referring to FIG. 4, the analog circuit 430 includes the first analog device 320 serially connected to the first impedance component 310 of the earphone 110. A first AC signal obtained as an analog signal due to the digital-analog conversion by the DAC 410 is input to the first impedance component 310 via the first analog device 320. When a voltage of the first AC signal is expressed by $e_i$, the impedance of the first impedance component 310 of the earphone 110 is expressed by R1, an impedance variation of the first impedance component 310 due to detection of the bio-signal is expressed by Δr, and the impedance of the first analog device 320 is expressed by R2, a voltage $e_d$ of a point b of an input terminal of the earphone 110 is calculated using Equation 1.

$$e_d = \frac{R1 + \Delta r}{R1 + R2 + \Delta r} e_i \quad \text{Equation 1}$$

Assuming that R1=R2, the voltage $e_d$ is calculated using Equation 2.

$$e_d = \frac{R1 + \Delta r}{2R1 + \Delta r} e_i \quad \text{Equation 2}$$

Because the impedance variation $\Delta r$ of the first impedance component 310 due to detection of the bio-signal is very small compared with the original impedance R1 of the earphone 110, the voltage $e_d$ is calculated using Equation 3.

$$e_d \cong \frac{R1 + \Delta r}{2R1} e_i \quad \text{Equation 3}$$

In other words, the voltage $e_d$ varies in proportion to R1+$\Delta r$. Thus, the electronic device 100a according to an embodiment of the disclosure detects the voltage $e_d$ proportional to a sum of the original impedance R1 of the earphone 110 and the impedance variation $\Delta r$ caused by the bio-signal, in order to detect the impedance variation $\Delta r$ caused by the bio-signal.

First, the amplifier 412 amplifies the voltage $e_d$ of the point b of the input terminal of the earphone 110, and inputs an amplified voltage to the BPF 414.

Then, the BPF 414 uses the predetermined frequency fi as a central frequency and removes noise other than the predetermined frequency fi from the voltage $e_d$. The BPF 414 inputs, to the ADC 416, a voltage component from which noise has been removed and which includes the impedance variation $\Delta r$ of the first impedance component 310 and is proportional to R1+$\Delta r$.

The ADC 416 performs analog-to-digital conversion on the voltage component including the impedance variation $\Delta r$ and being proportional to R1+$\Delta r$, and inputs a result of the analog-to-digital conversion to the orthogonal demodulator 420.

The orthogonal demodulator 420 includes a mixer 421, a low pass filter (LPF) 424, a 90° phase shifter 418, a mixer 422, and an LPF 426. The orthogonal demodulator 420 orthogonally demodulates the voltage component proportional to R1+$\Delta r$ output by the BPF 414, by using the AC signal cos(2π×fi×t) generated by the signal generator 130 as a local signal, thereby generating an in-phase component I and a quadrature phase component Q.

The mixer 421 mixes the AC signal cos(2π×fi×t) generated by the signal generator 130 with a signal output by the ADC 416 and inputs a signal obtained by the mixing to the LPF 424. The LPF 424 removes a high frequency component from the signal output by the mixer 421, and generates the in-phase component I.

The 90° phase shifter 418 90°-shifts the phase of the AC signal cos(2π×fi×t) generated by the signal generator 130, and inputs a 90°-shifted AC signal sin(2π×fi×t) to the mixer 422. The mixer 422 mixes the 90°-shifted AC signal sin(2π×fi×t) obtained by the 90° phase shifter 418 with the signal output by the ADC 416 and inputs a signal corresponding to a result of the mixing to the LPF 426. The LPF 426 removes a high frequency component from the signal output by the mixer 422 and generates the quadrature phase component Q.

Figure 5:
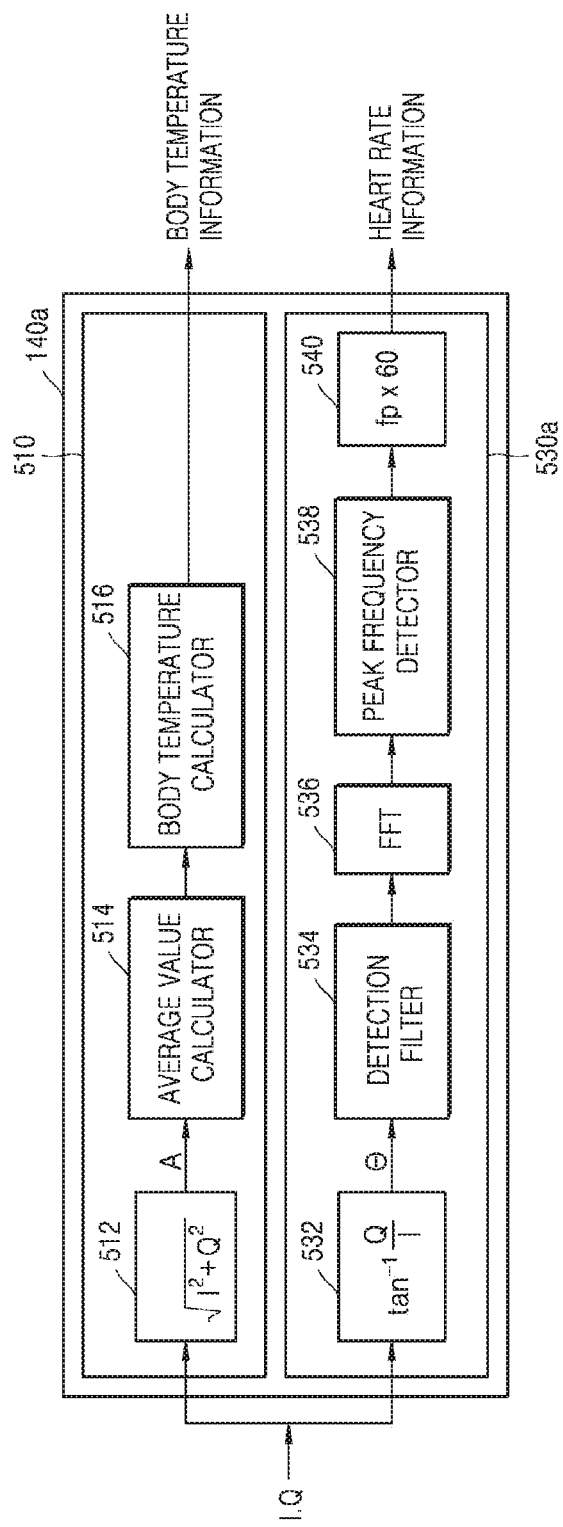
FIG. 5 is a block diagram of a processor according to an embodiment of the disclosure.

FIG. 5 is a block diagram of a processor according to an embodiment of the disclosure.

Referring to FIG. 5, the processor 140a calculates an amplitude component A and a phase component θ from the in-phase component I and the quadrature phase component Q generated by the orthogonal demodulator 420, and calculates biometric information by using at least one of the amplitude component A and the phase component θ. The processor 140a includes a body temperature information generator 510 and a heart rate information generator 530a. The body temperature information generator 510 and the heart rate information generator 530a generate body temperature information from the in-phase component I and the quadrature phase component Q. The body temperature generator 510 includes an amplitude calculator 512, an average value calculator 514, and a body temperature calculator 516. The heart rate information generator 530a includes a phase calculator 532, a detection filter 534, a fast Fourier transformer (FFT) 536, a peak frequency detector 538, and a pulse calculator 540.

The amplitude calculator 512 sums a square of the in-phase component I and a square of the quadrature phase component Q, and calculates a square root of a sum to thereby calculate the amplitude component A. The average value calculator 514 calculates an average value of a relatively long period (for example, at least several seconds or at most several minutes) of the amplitude component A calculated by the amplitude calculator 512. The body temperature calculator 516 calculates a body temperature from the average value calculated by the average value calculator 514. Specifically, the body temperature calculator 516 calculates the body temperature by using a linear expression using the average value calculated by the average value calculator 514 as a parameter. An integer of the linear expression is obtained in advance through an experiment.

The phase calculator 532 calculates the phase component θ by calculating an arctangent ($\tan^{-1}(Q/I)$) of a value obtained by dividing the quadrature phase component Q by the in-phase component I. The detection filter 534 is a BPF using a frequency including a target bio-signal (pulse in the example of FIG. 5) as a central frequency, and emphasizes a desired frequency (frequency of the pulse in the example of FIG. 5) from the phase component θ calculated by the phase calculator 532. The FFT 536 performs fast Fourier transformation on a signal output by the detection filter 534 and inputs a signal obtained by the fast Fourier transformation to the peak frequency detector 538. The peak frequency detector 538 detects a frequency fp having largest power from the signal received from the FFT 536. Next, the pulse calculator 540 calculates a pulse (the number of pulse waves) for one minute by multiplying the frequency fp [ Hz ] detected by the peak frequency detector 538 by 60, thereby calculating a heart rate for one second.

Figure 6:
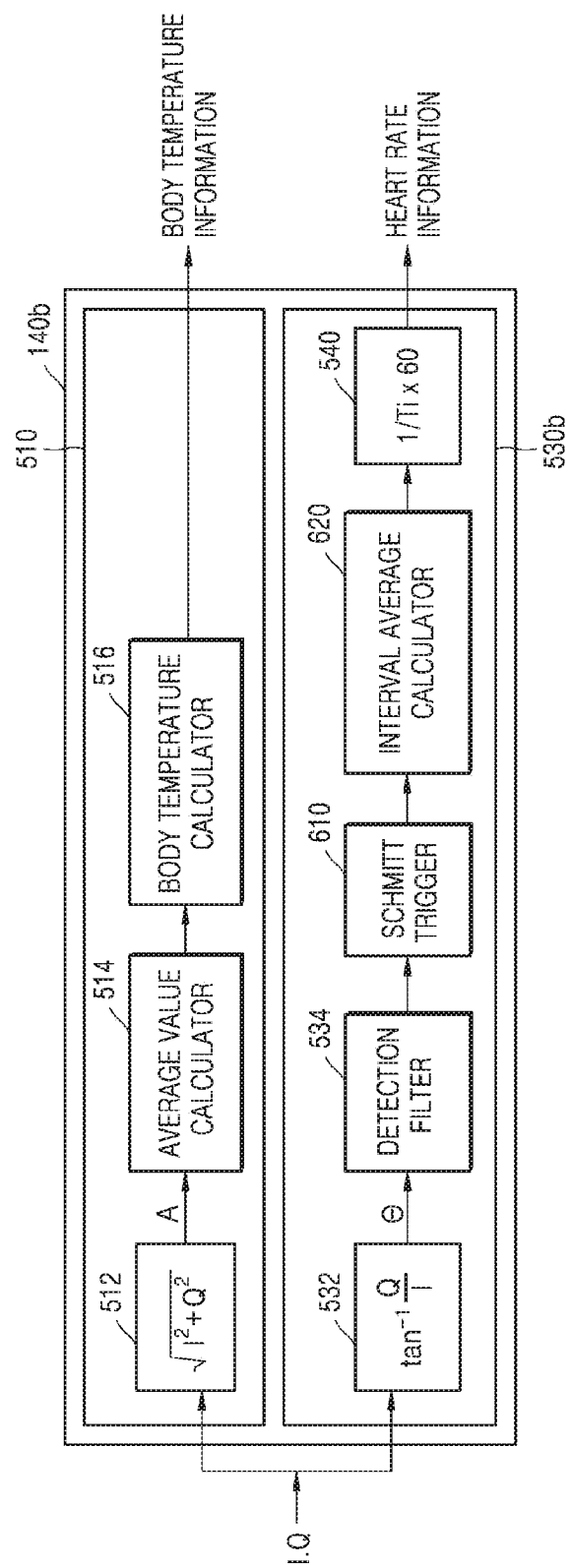
FIG. 6 is a block diagram of a processor according to an embodiment of the disclosure.

FIG. 6 is a block diagram of a processor according to an embodiment of the disclosure.

Referring to FIG. 6, a processor 140b includes a body temperature information generator 510 and a heart rate information generator 530b. The body temperature information generator 510 is the same as that described above with reference to FIG. 5. The heart rate information generator 530b includes the phase calculator 532, the detection filter 534, a Schmitt trigger 610, an interval average calculator 620, and the pulse calculator 540. The description of components of FIG. 6 which are the same as those of FIG. 5 is omitted herein.

The Schmitt trigger 610 binarizes the signal output by the detection filter 534. Then, the interval average calculator 620 calculates an average value Ti by averaging a waveform period of a binarized signal obtained by the Schmitt trigger 610 in a predetermined time interval (for example, a time interval of several seconds to about 10 seconds). The pulse calculator 540 calculates a pulse (the number of pulse waves) for one minute by multiplying a reciprocal of the average value Ti [second] calculated by the interval average calculator 620 by 60.

Figure 7:
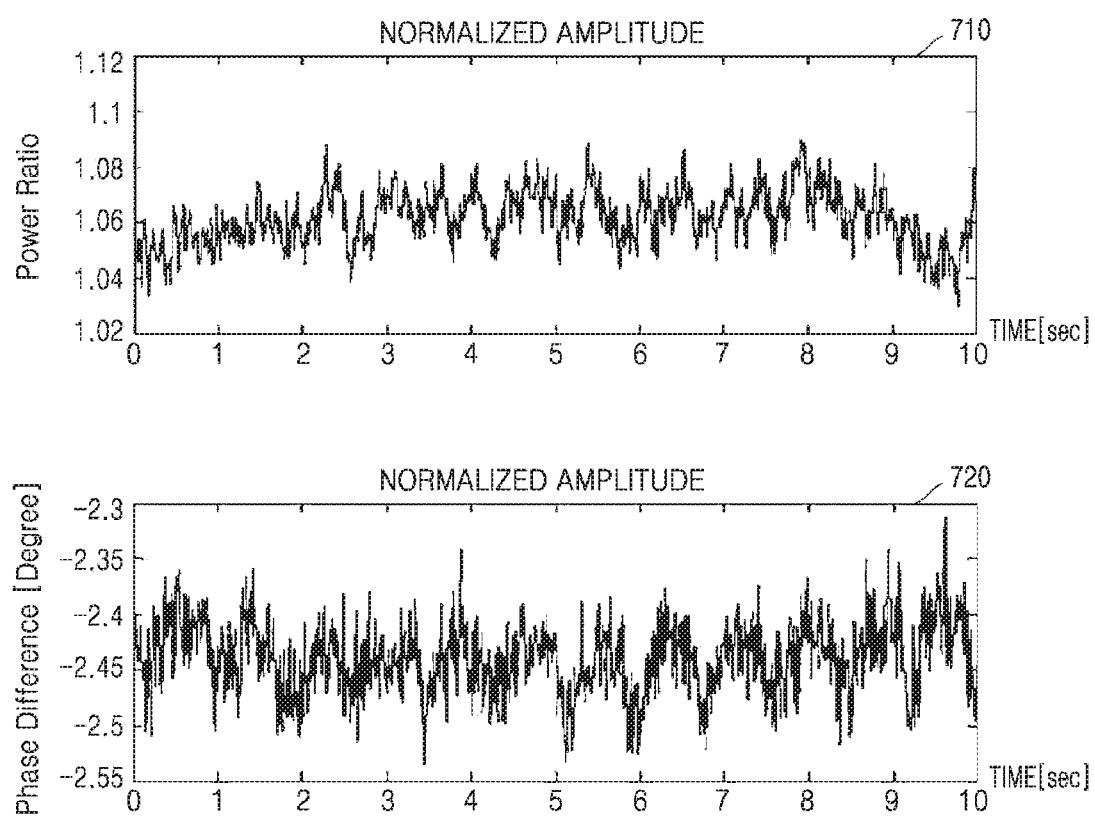
FIG. 7 illustrates a waveform representing a change, over time, in an amplitude component generated by a processor, and a waveform representing a change, over time, in a phase component generated by the processor according to an embodiment of the disclosure.

FIG. 7 illustrates an example 710 of a waveform representing a change, over time, in an amplitude component A generated by a processor, and an example 720 of a waveform representing a change, over time, in a phase component θ generated by the processor according to an embodiment of the disclosure.

The vertical axis of the graph of FIG. 7 indicates the amplitude component A or the phase component θ, and the horizontal axis thereof indicates time (second).

Figure 8:
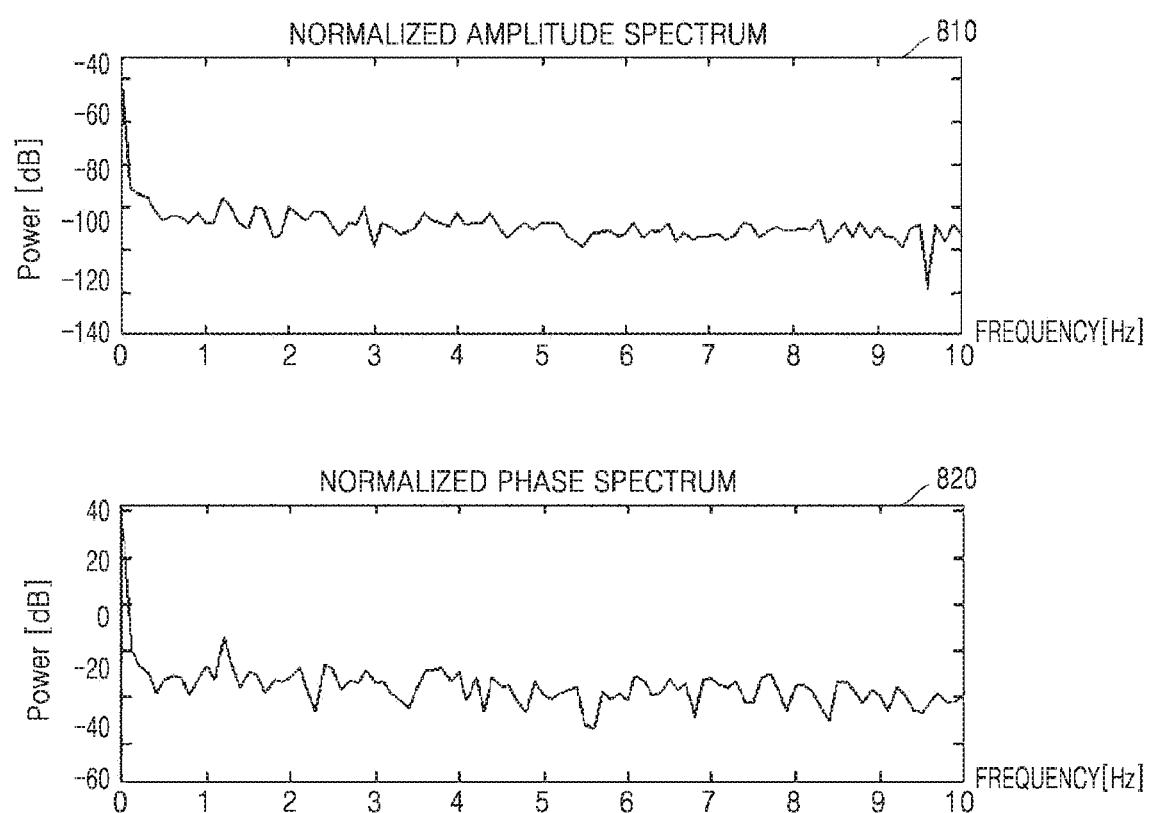
FIG. 8 illustrates a spectrum of an amplitude component generated by a processor, and a spectrum of a phase component generated by the processor according to an embodiment of the disclosure.

FIG. 8 illustrates an example 810 of a spectrum of an amplitude component A generated by a processor according to an embodiment of the disclosure, and an example 820 of a spectrum of a phase component θ generated by the processor.

Figure 9:
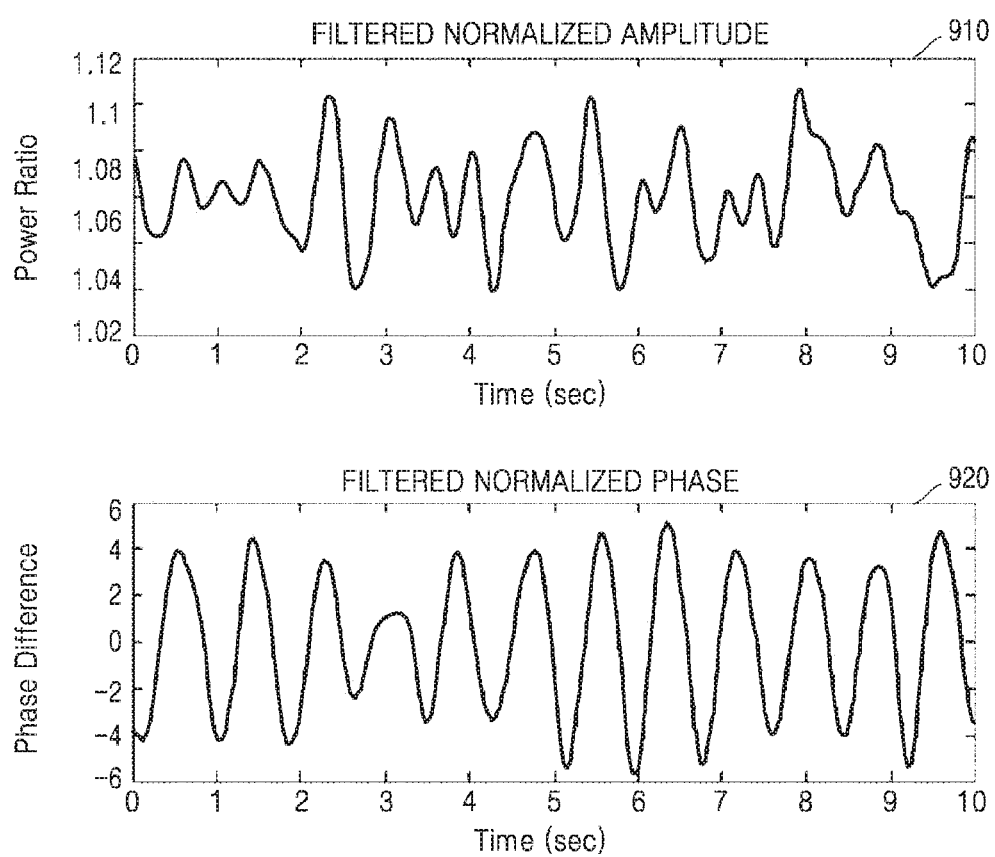
FIG. 9 illustrates a waveform representing a change, over time, in an amplitude component having passed through a detection filter of a processor, and a waveform representing a change, over time, in a phase component having passed through the detection filter of the processor according to an embodiment of the disclosure.

FIG. 9 illustrates an example 910 of a waveform representing a change, over time, in an amplitude component A having passed through a detection filter of a processor, and an example 920 of a waveform representing a change, over time, in a phase component θ having passed through the detection filter of the processor according to an embodiment of the disclosure.

The vertical axis of FIG. 9 indicates the amplitude component A or the phase component θ, and the horizontal axis thereof indicates time (second).

Figure 10:
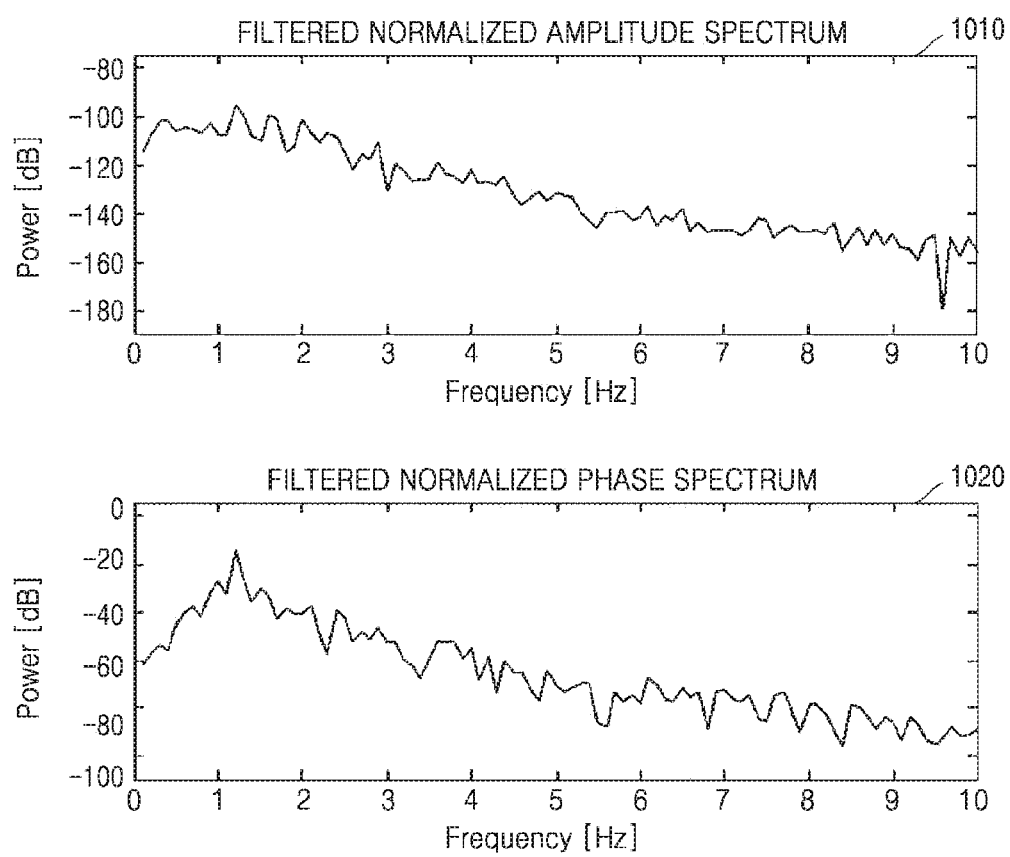
FIG. 10 illustrates a spectrum of an amplitude component having passed through a detection filter of a processor, and a spectrum of a phase component having passed through the detection filter of the processor according to an embodiment of the disclosure.

FIG. 10 illustrates an example 1010 of a spectrum of an amplitude component A having passed through a detection filter of a processor, and an example 1020 of a spectrum of a phase component θ having passed through the detection filter of the processor according to an embodiment of the disclosure.

Referring to FIGS. 7 and 8, the examples 720 and 820 associated with the phase component θ generated by the processors 140a and 140b more clearly represent pulse waves than the examples 710 and 810 associated with the amplitude component A generated by the processors 140a and 140b do.

Referring to FIGS. 9 and 10, because noise other than the central frequency is removed by the detection filter 534, the examples 920 and 1020 associated with the phase component θ more clearly represent pulse waves, and clearly represent a component including a peak frequency even after fast Fourier transformation is performed.

In the above-described electronic device 100 according to an embodiment of the disclosure, an AC signal having the predetermined frequency fi is input to the analog circuit 430 including the first impedance component 310 of the earphone 110, and thus the analog circuit 430 outputs a voltage including the voltage component corresponding to the impedance variation of the earphone 110. Accordingly, the above-described electronic device 100 may calculate biometric information, based on the impedance variation caused by a bio-signal, such as a pulse wave or a body temperature, of a human body wearing the earphone 110. Thus, the electronic device 100 according to an embodiment of the disclosure may detect the biometric information while providing sound waves corresponding to an audio signal.

Because the frequency of a pulse wave is about several Hz and the size thereof is very small, it is difficult to detect the pulse wave. According to embodiments of the disclosure, even when an amplifier having a high amplification factor at a frequency close to a direct current (DC) is not used, the impedance variation caused by the bio-signal of the human body wearing the earphone 110 may be detected. Therefore, according to embodiments of the disclosure, a large coil and a condenser are not needed to realize an amplifier having a high amplification factor. Accordingly, according to embodiments of the disclosure, a circuit may be formed to have a small and simple structure.

In addition, according to embodiments of the disclosure, because the predetermined frequency fi is a frequency having 20 kHz or greater, ultrasound waves of 20 kHz or greater that is inaudible to human being may be input to the electrical circuit of the earphone 110 via the analog circuit 430, and the biometric information may be detected without destroying an audio providing function of the earphone 110.

According to embodiments of the disclosure, because the predetermined frequency fi is less than or equal to 40 kHz, difficulty in realizing the ADC 416 having a sampling frequency that is twice the predetermined frequency fi may be prevented.

According to embodiments of the disclosure, the BPF 414 may remove noise other than the predetermined frequency fi from the voltage $e_d$ that is applied to the first impedance component 310. In other words, the BPF 414 is able to input, to the ADC 416, a voltage component from which noise has been removed and which is proportional to R1+Δr including the impedance variation Δr, leading to an increase in a signal-to-noise ratio (SNR) of the first detection signal.

According to embodiments of the disclosure, the analog circuit 430 is configured using the first impedance component 310 of the earphone 110 and the first analog device 320 being a fixed impedance component serially connected to the first impedance component 310, thereby having a simple structure.

According to embodiments of the disclosure, the orthogonal demodulator 420 orthogonally demodulates the signal output by the BPF 414 by using the AC signal generated by the signal generator 130 as a local signal, and thus the in-phase component I and the quadrature phase component Q are generated, the processor 140 calculates the amplitude component A and the phase component θ from the in-phase component I and the quadrature phase component Q, and the biometric information is calculated using at least one of the amplitude component A or the phase component θ. Thus, the biometric information may be calculated based on the impedance variation Δr of the earphone 110.

Next, a first circuit according to another embodiment of the disclosure will be described with reference to FIGS. 11 and 12.

Figure 11:
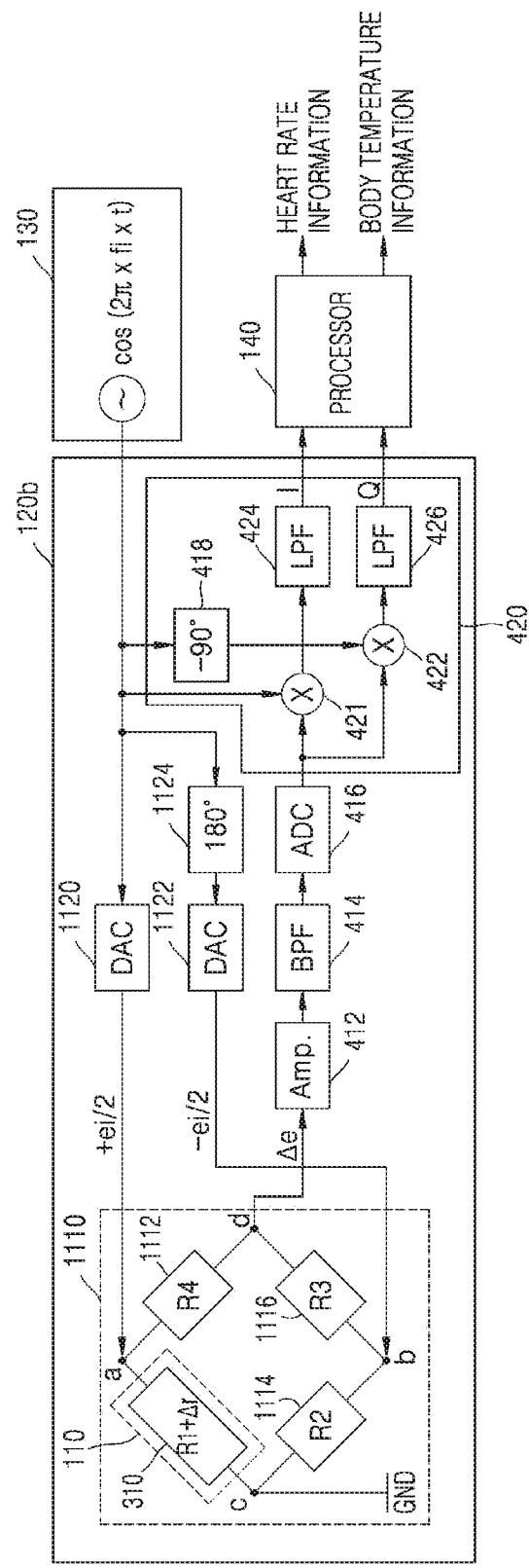
FIG. 11 is a block diagram of an electronic device according to an embodiment of the disclosure.

FIG. 11 is a block diagram of an electronic device according to an embodiment of the disclosure.

Figure 12:
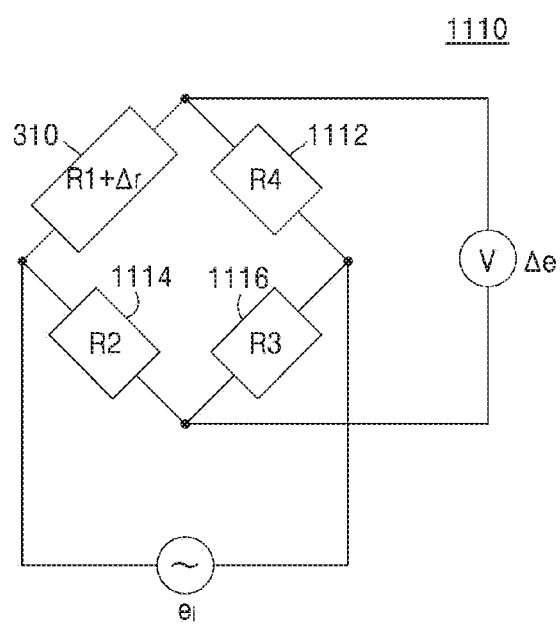
FIG. 12 is a schematic circuit diagram of an analog circuit according to an embodiment of the disclosure.

FIG. 12 is a schematic circuit diagram of an analog circuit according to an embodiment of the disclosure.

Referring to FIG. 11, the electronic device 100 according to another embodiment of the disclosure includes the earphone 110, a first circuit 120b, the signal generator 130, and the processor 140. The first circuit 120b includes a DAC 1120, a 180° phase shifter 1124, a DAC 1122, and the analog circuit 1110, and thus the electronic device 100 of FIG. 11 is different from the electronic device 100 of FIG. 4. Like reference numerals or characters are assigned to components of the electronic device 100 of FIGS. 11 and 12 corresponding to those of the electronic device 100 of FIG. 4, and repeated descriptions thereof will be omitted.

Referring to FIG. 11, the AC signal generated by the signal generator 130 is transmitted along different paths, one path thereof leading to the DAC 1120 and the other path leading to the 180° phase shifter 1124. The DAC 1120 performs digital-to-analog conversion on the AC signal generated by the signal generator 130, and inputs a result of the digital-analog conversion to the analog circuit 1110. The 180° phase shifter 1124 180°-shifts the phase of the first AC signal generated by the signal generator 130, and inputs an AC signal having a 180°-shifted phase to the DAC 1122. The DAC 1122 performs digital-to-analog conversion on the AC signal having a 180°-shifted phase, and inputs a result of the digital-to-analog conversion to the analog circuit 1110.

Referring to FIG. 12, the analog circuit 1110 is a bridge circuit. The bridge circuit includes the first impedance component 310, being the impedance of the earphone 110, a second impedance 1114, a third impedance 1116, and a fourth impedance 1112. Each of the second impedance 1114, the third impedance 1116, and the fourth impedance 1112 may correspond to at least one analog device (for example, at least one of a resistor, a capacitor, or an inductor, or a combination thereof). The second impedance 1114, the third impedance 1116, and the fourth impedance 1112 are fixed impedances. A fixed impedance is a circuit including at least one of a fixed resistor, a fixed inductor, or a fixed capacitor, or a combination thereof Given that the voltage of the first AC signal is $e_i$, a half of the first AC signal, $+e_i/2$, is input from the signal generator 130 to a first node (node a) between the first impedance 310 and the fourth impedance 1112, and a half of an inversion signal obtained by inverting the phase of the first AC signal, $-e_i/2$, is input to a second node (node b) between the second impedance 1114 and the third impedance 1116. Accordingly, a sinusoidal voltage of an amplitude ei is input between the nodes a and b of the bridge circuit.

Given that the first impedance 310 being an impedance of the earphone 110 is R1, the impedance variation of the first impedance 310 due to detection of the bio-signal is Δr, the impedance of the second impedance 1114 is R2, the impedance of the third impedance 1116 is R3, and the impedance of the fourth impedance 1112 is R4, a voltage Δe between a node c and a node d of the bridge circuit is calculated using Equation 4.

$$\Delta e = \frac{\left(1 + \frac{\Delta R}{R1}\right) - \frac{R2 R4}{R1 R3}}{\left(1 + \frac{\Delta r}{R1} + \frac{R4}{R1}\right)\left(\frac{R2}{R3} + 1\right)} e_i \qquad \text{Equation 4}$$

Assuming that R4=R1 and R3=R2, the voltage Δe is calculated using Equation 5.

$$\Delta e = \frac{\frac{\Delta r}{R1}}{\left(2 + \frac{\Delta r}{R1}\right) \cdot 2} e_i = \frac{\Delta r}{4R1 + 2\Delta r} e_i \qquad \text{Equation 5}$$

Because the impedance variation Δr of the first impedance component 310 due to detection of the bio-signal is very small compared with the original impedance R1 of the earphone 110, the voltage Δe is calculated using Equation 6 below.

$$\Delta e \cong \frac{\Delta r}{4R1} e_i \qquad \text{Equation 6}$$

In other words, the voltage Δe varies in proportion to Δr. Thus, the electronic device 100 according to another embodiment of the disclosure detects the voltage Δe proportional to Δr that originates from the bio-signal.

First, the amplifier 412 amplifies the voltage Δe between the nodes c and d of the bridge circuit, and inputs an amplified voltage Δe to the BPF 414.

Then, the BPF 414 uses the predetermined frequency fi as the central frequency and removes noise other than the predetermined frequency fi from the voltage Δe. The BPF 414 inputs a noise-removed voltage Δe to the ADC 416. Then, the ADC 416 converts the noise-removed voltage Δe into a digital signal, and the orthogonal demodulator 420 generates the in-phase component I and the quadrature phase component Q. Next, the processor 140 calculates the biometric information, based on the in-phase component I and the quadrature phase component Q.

The above-described electronic device 100 according to another embodiment of the disclosure obtains the same effects as the electronic device 100 of FIG. 4. Moreover, because the analog circuit 1110 is a bridge circuit, the above-described electronic device 100 may input the voltage Δe proportional to the impedance variation Δr caused by the bio-signal to the BPF 414 and may more precisely detect biometric information.

In the electronic device 100 of FIG. 4, the voltage $e_d$ proportional to the sum of the original impedance R1 of the earphone 110 and the impedance variation Δr caused by the bio-signal is input to the BPF 414. Because the impedance variation Δr is very small compared with the original impedance R1 of the earphone 110, a variation in the voltage $e_d$ that accompanies a change in Δr is very small, and a detection sensitivity is low. However, in the electronic device 100 of FIGS. 11 and 12, the voltage Δe proportional to only the impedance variation Δr caused by the bio-signal is input to the BPF 414, and thus a change in Δr and a variation in the voltage Δe become equal. Therefore, biometric information may be more precisely detected.

Next, another embodiment of the disclosure will be described with reference to FIG. 13.

Figure 13:
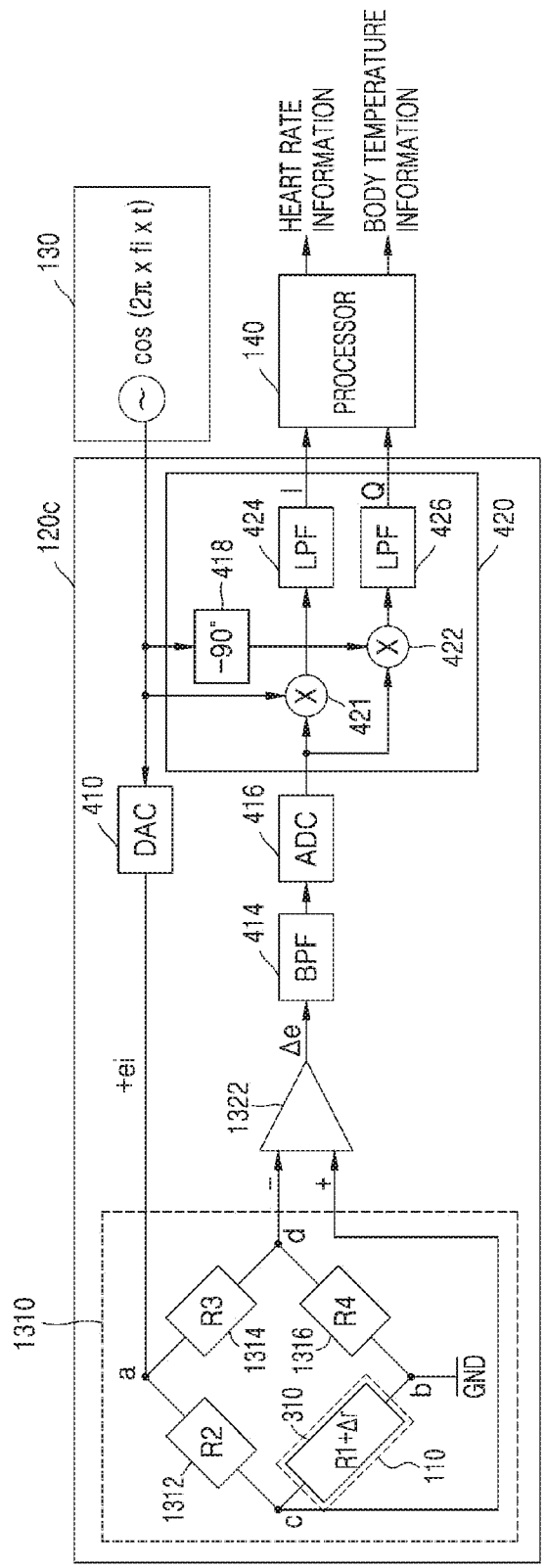
FIG. 13 is a block diagram of an electronic device according to an embodiment of the disclosure.

FIG. 13 is a block diagram of an electronic device according to an embodiment of the disclosure.

Referring to FIG. 13, the electronic device 100 is different from the electronic device 100 of FIG. 4 in that a first circuit 120c, a DAC 410, a differential amplifier 1322, and an analog circuit 1310 are included. Like reference numerals or characters are assigned to components of the electronic device 100 of FIG. 13 corresponding to those of the electronic device 100 of FIG. 4, and repeated descriptions thereof will be omitted.

Referring to FIG. 13, the first AC signal generated by the signal generator 130 is input to the DAC 410. The DAC 410 performs digital-to-analog conversion on the first AC signal generated by the signal generator 130, and inputs a result of the digital-to-analog conversion to the analog circuit 1310.

Referring to FIG. 13, the analog circuit 1310 is a bridge circuit. The bridge circuit includes the first impedance component 310, being the impedance of the earphone 110, a second impedance 1312, a third impedance 1314, and a fourth impedance 1316.

The second impedance 1312, the third impedance 1314, and the fourth impedance 1316 are fixed impedances. A fixed impedance is a circuit including at least one of a fixed resistor, a fixed inductor, or a fixed capacitor, or a combination thereof Given that the voltage of the first AC signal is $+e_i$, the voltage $+e_i$ of the first AC signal is input from the signal generator 130 to a first node (node a) between the second impedance 1312 and the third impedance 1314, and a second node (node b) between the first impedance 310 and the fourth impedance 1316 is grounded. Accordingly, a sinusoidal voltage of an amplitude $e_i$ is input between the nodes a and b of the bridge circuit.

Similar to the analog circuit 1110 of FIGS. 11 and 12, a voltage Δe between nodes c and d the analog circuit 1310 of FIG. 13 varies in proportion to the impedance variation Δr of the first impedance 310 due to detection of the bio-signal. Thus, the electronic device 100 according to various embodiments of the disclosure detects the voltage Δe proportional to Δr that originates from the bio-signal.

The differential amplifier 1322 detects the voltage Δe by taking a differential value between an input voltage at the node c between the second impedance 1312 and the first impedance 310 and an input voltage at the node d between the third impedance 1314 and the fourth impedance 1316. The differential amplifier 1322 amplifies the voltage Δe and inputs an amplified voltage Δe to the BPF 414. Subsequent processes are the same as those of FIG. 11, and thus detailed descriptions thereof will be omitted.

In the above-described electronic device 100 of FIG. 13 according to another embodiment of the disclosure, the same effects as those of the electronic device 100 of FIGS. 11 and 12 are obtained, and, because the first AC signal is input from the signal generator 130 to between the second impedance 1312 and the third impedance 1314, and the node between the first impedance 310 and the fourth impedance 1316 is grounded, a single AC signal is input from the signal generator 130 to the bridge circuit of the analog circuit 1310. Accordingly, compared with the electronic device 100 of FIG. 11 in which two AC signals, namely, the half of the AC signal $+e_i/2$ and the half of the inversion signal obtained by inverting the AC signal, $-e_i/2$, are input to the bridge circuit of the analog circuit 1110, in the embodiment of FIG. 13, phase adjustment enabling a phase difference of two AC signals to be accurately 180° is unnecessary, and biometric information may be detected more easily and more precisely.

Next, another embodiment of the disclosure will be described with reference to FIG. 14.

Figure 14:
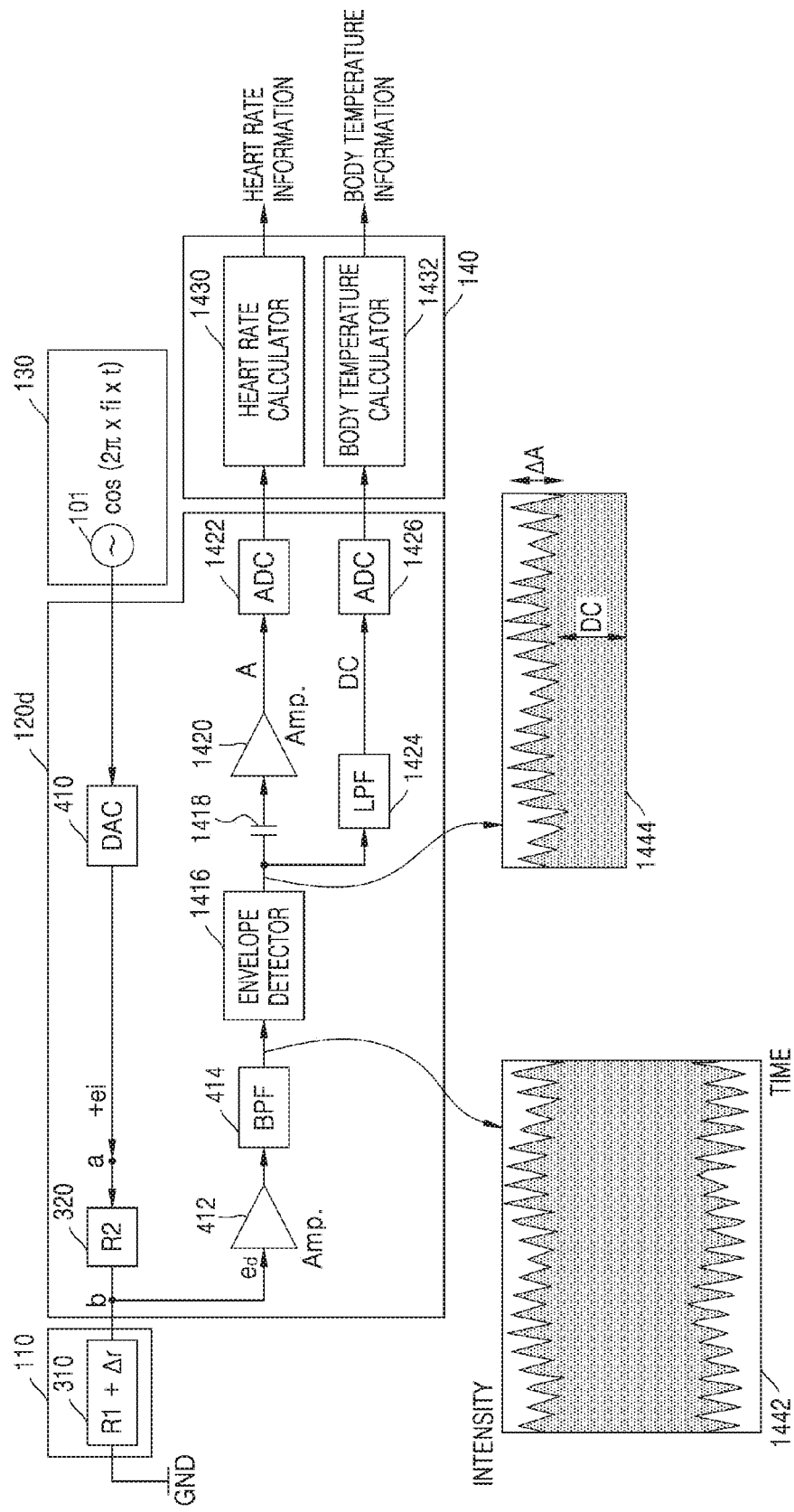
FIG. 14 is a block diagram of an electronic device according to an embodiment of the disclosure.

FIG. 14 is a block diagram of an electronic device according to an embodiment of the disclosure.

Referring to FIG. 14, the electronic device 100 according to the embodiment is different from the embodiment of FIG. 4 in that a first circuit 120d includes an envelope detector 1416, a condenser 1418, an amplifier 1420, an ADC 1422, a pulse calculator 405 as a biometric information calculator, an LPF 1424, and an ADC 1426. The embodiment is also different from the embodiment of FIG. 4 in terms of a first detection signal that is input to the processor 140. Accordingly, operations of a heart rate calculator 1430 and a body temperature calculator 1432 of the processor 140 are different from the processor 140 of FIG. 4. Like reference numerals or characters are assigned to components of the electronic device 100 of FIG. 14 corresponding to those of the electronic device 100 of FIG. 4, and repeated descriptions thereof will be omitted.

In the electronic device 100 of FIG. 4, the signal $e_d$ input from the analog circuit 430 to the BPF 414 via the amplifier 412 includes the voltage component proportional to the impedance R1 of the original first impedance component of the earphone 110 in addition to the voltage component proportional to Δr originating from the bio-signal. Moreover, because the impedance variation Δr among the first impedance component is very small compared with the original impedance R1 of the earphone 110, a variation in the voltage $e_d$ that accompanies a change in Δr becomes very small, and thus a detection sensitivity is low.

Accordingly, in the electronic device 100, first, the envelope detector 1416 detects an envelope of the signal output by the BPF 414. The envelope detector 1416 envelope-detects the voltage change ed of the node b to obtain an amplitude change component ΔA and a DC component DC. For example, the envelope detector 1416 receives an AC signal 1442, and outputs a signal representing an envelope 1444 of the received AC signal 1442. The signal output by the envelope detector 1416 is transmitted along two paths.

On one path, the condenser 1418 removes a DC component of an envelope detection signal output by the envelope detector 1416. The DC component of the envelope detection signal corresponds to the voltage component proportional to the original impedance R1 of the earphone 110. Accordingly, due to the removal of the DC component of the envelope detection signal by the condenser 1418, the voltage component proportional to the impedance variation Δr originating from the bio-signal is extracted from the envelope detection signal. A signal output by the condenser 1418 is amplified by the amplifier 1420 and converted into a digital signal by the ADC 1422. The digital signal output by the ADC 1422 corresponds to the amplitude component A generated by the processor 140 of FIG. 4. As shown in FIGS. 7 and 8, the phase component θ generated by the processor 140 represents a pulse wave better than the amplitude component A generated by the processor 140. According to the embodiment of the disclosure, a pulse may be calculated using the same method even when the amplitude component A instead of the phase component θ is used. The heart rate calculator 1430 calculates a pulse, based on the signal output by the ADC 1422, by using the same method as that used in the processor 140 of FIG. 4.

On the other path, the LPF 1424 transmits the DC component of the envelope detection signal output by the envelope detector 1416. As described above, the DC component of the envelope detection signal corresponds to the voltage component proportional to the original impedance R1 of the earphone 110. For example, because the body temperature of the examinee wearing the earphone 110 changes, the temperature of the entire earphone 110 changes, and the original impedance R1 of the earphone 110 also changes. Accordingly, biometric information, such as a body temperature may be detected based on the DC component of the envelope detection signal output by the envelope detector 1416, which corresponds to the voltage component proportional to the original impedance R1 of the earphone 110.

The ADC 1426 converts the DC component of the envelope detection signal output by the LPF 1424 into a digital signal. The digital signal output by the ADC 1426 corresponds to an average of a relatively long period (for example, at least several seconds or greater or at most several minutes) of the amplitude component A generated by the processor 140 of FIG. 4. Accordingly, the body temperature calculator 1432 calculates a body temperature, based on the digital signal output by the ADC 1426, by using the same method as that used in the processor 140 of FIG. 4.

In the above-described electronic device 100 of FIG. 14 according to another embodiment of the disclosure, the same effects as those of the electronic device 100 of FIG. 4 are obtained, and, because the condenser 1418 removes the DC component of the envelope detection signal, the biometric information may be calculated by extracting the impedance variation Δr of the earphone 110 caused by the bio-signal.

Therefore, the above-described electronic device 100 of FIG. 14 may more precisely detect the biometric information.

Moreover, because the DC component of the envelope detection signal is extracted by the LPF 1424, the above-described electronic device 100 of FIG. 14 may calculate the biometric information, based on a change in the DC component caused by the bio-signal.

Next, another embodiment of the disclosure will be described with reference to FIG. 15.

Figure 15:
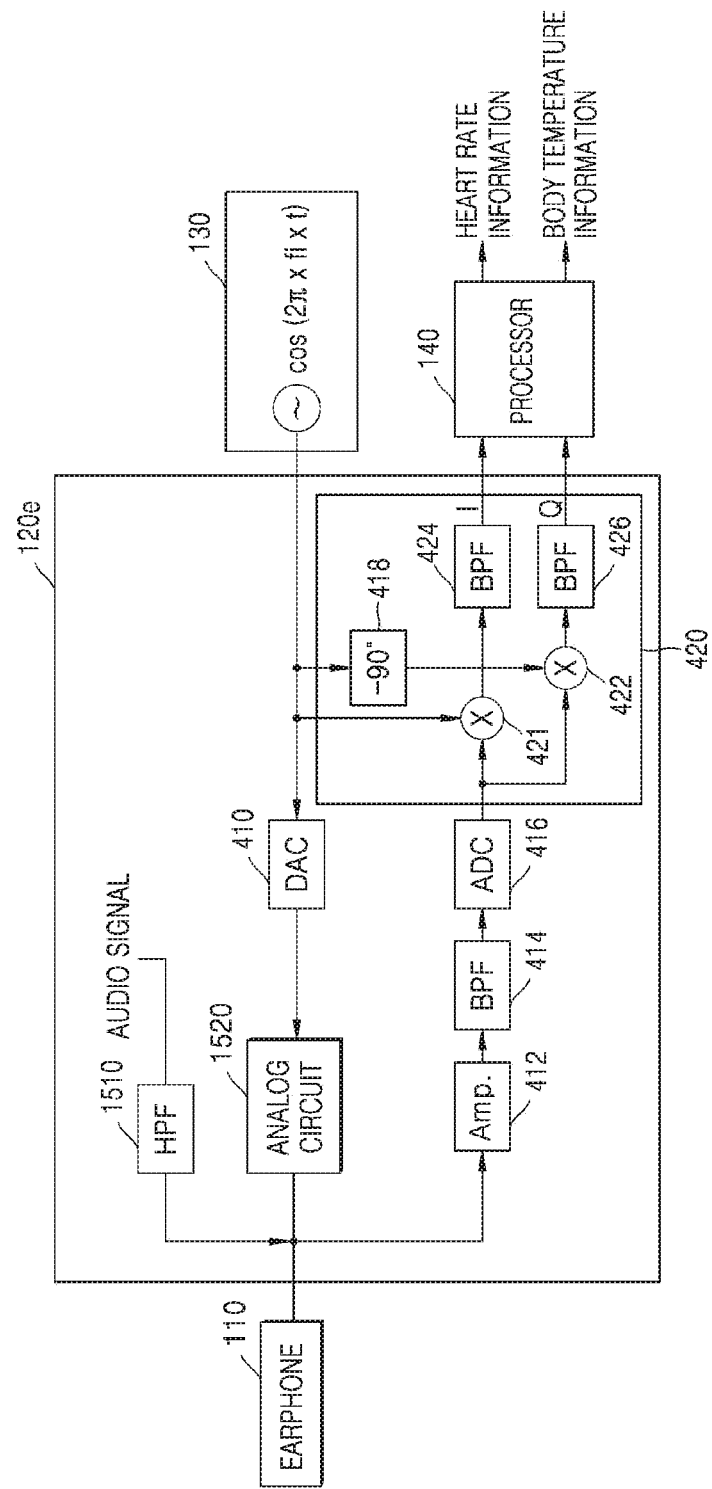
FIG. 15 is a block diagram of an electronic device according to an embodiment of the disclosure.

FIG. 15 is a block diagram of an electronic device according to an embodiment of the disclosure.

Referring to FIG. 15, the electronic device 100 according to another embodiment of the disclosure is different from the electronic devices 100 according to the embodiments of FIGS. 4, 11, 13, and 14 in that a first circuit 120e, a DAC 410, and a high pass filter (HPF) 1510 is included. Like reference numerals or characters are assigned to components of the electronic device 100 of FIG. 15 corresponding to those of the electronic device 100 of FIG. 4, and repeated descriptions thereof will be omitted. An analog circuit 1520 of the electronic device 100 of FIG. 15 corresponds to each of the analog circuits 430, 1110, and 1310 of FIGS. 4, 11, 13, and 14.

The HPF 1510 has a cutoff frequency of the predetermined frequency fi and transmits a higher frequency than the predetermined frequency fi. An audio signal output by an audio player, such as an audio apparatus is input to the earphone 110 via the HPF 1510. In other words, the HPF 1510 inputs to the earphone 110 an audio signal from which a frequency component less than or equal to the predetermined frequency fi has been removed. The audio signal indicates an electrical analog signal representing audio data. The audio signal is input to the earphone 110, and the earphone 110 transforms the audio signal into a sound wave signal and outputs the sound wave signal.

Likewise the embodiment of FIG. 4, the predetermined frequency fi may be a frequency of at least 20 kHz being a lower limit frequency of an ultrasound wave that is generally inaudible to human beings. When the predetermined frequency fi is a frequency of 20 kHz or greater, the HPF 1510 may input, to the earphone 110, an audio data signal from which ultrasound waves being a noise component have been removed.

The HPF 1510 removes a frequency component less than or equal to the predetermined frequency fi from the audio data signal. Accordingly, even when the audio data signal is input from the audio player, such as an audio apparatus to the earphone 110, a first AC signal $\cos(2\pi \times fi \times t)$ having the predetermined frequency fi is input to the earphone 110 via the analog circuit 1520, and thus the frequency component of the audio data signal may be prevented from interfering in detecting the impedance variation $\Delta r$ caused by the bio-signal of the earphone 110.

In the above-described electronic device 100 of FIG. 15 according to another embodiment of the disclosure, the same effects as those of the electronic devices 100 of FIGS. 4, 11, 13, and 14 are obtained, and the HPF 1510 removes, from the audio data signal output by the audio player, such as an audio apparatus, a nose component of the audio signal corresponding to the frequency component less than or equal to the predetermined frequency fi of the first AC signal generated by the signal generator 130. Accordingly, the frequency component of the audio data signal may be prevented from interfering in detection of the impedance variation $\Delta r$ caused by the bio-signal of the earphone 110 that is performed due to the inputting of the first AC signal having the predetermined frequency fi to the analog circuit 1520. Thus, according to the embodiment of the disclosure, the electronic device 100 may more precisely detect biometric information while providing the audio signal.

Because the frequency of a pulse wave is about several Hz, it is difficult to be separated from a low frequency component included in audio data, such as sound or music. Thus, when the embodiment is not applied, it is difficult to detect biometric information, such as a pulse wave, while providing an audio signal, such as sound or music.

Because the frequency of a pulse wave is about several hertz (Hz) and is weak, an amplifier having a high amplification factor is necessary at a frequency close to a DC. However, a large coil and a condenser are needed to realize such an amplifier. Because a condenser is unable to be used for end-to-end coupling of a low frequency amplification circuit, a voltage offset countermeasure of an amplifier is necessary, and a circuit is prone to be large and complicated.

To address this problem, the embodiment provides the electronic device 100 capable of detecting biometric information while providing audio.

Next, another embodiment of the disclosure will be described with reference to FIG. 16.

Figure 16:
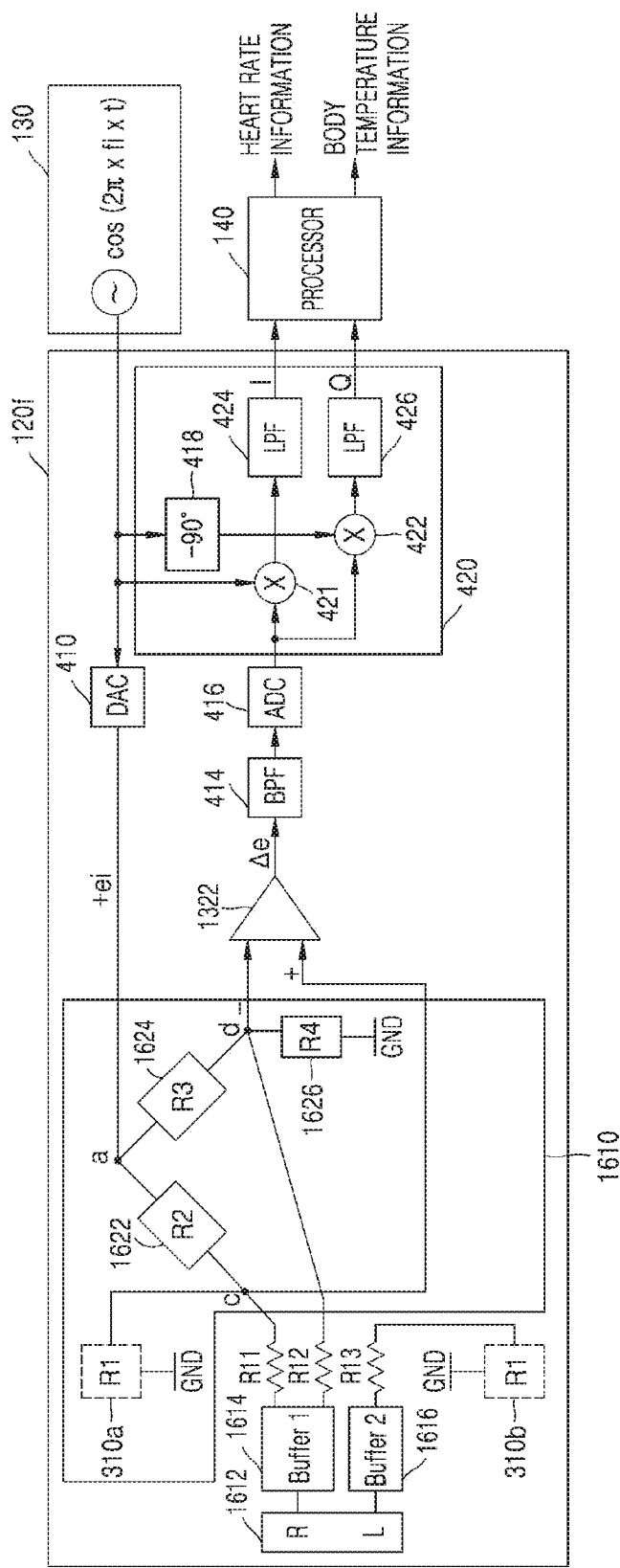
FIG. 16 is a block diagram of an electronic device according to an embodiment of the disclosure.

FIG. 16 is a block diagram of an electronic device according to an embodiment of the disclosure.

Referring to FIG. 16, the electronic device 100 according to the embodiment is different from the electronic device 100 of FIG. 13 in terms of the structure of an analog circuit 1610 and a first circuit 120f. Like reference numerals or characters are assigned to components of the electronic device 100 of FIG. 16 corresponding to those of the electronic device 100 of FIG. 13, and repeated descriptions thereof will be omitted.

In the example of FIG. 16, an audio signal is input from an audio player 1612, such as an audio apparatus to a right-ear earphone and a left-ear earphone, and the electronic device 100 detects a variation $\Delta r$ caused by a bio-signal of an impedance 310a of the right-ear earphone. According to another embodiment of the disclosure, the electronic device 100 may detect a variation $\Delta r$ caused by a bio-signal of an impedance 310b of the left-ear earphone. In this case, the analog circuit 1610 includes the impedance 310b of the left-ear earphone instead of the impedance 310a of the right-ear earphone. An audio signal may be input from the audio player 1612 to an earphone 110 for only one ear (also referred to as a monaural earphone), and the electronic device 100 may detect an impedance variation $\Delta r$ caused by a bio-signal of the earphone 110 for only one ear. In this case, the analog circuit 1610 includes the impedance of the earphone 110 for only one ear instead of the impedance 310a of the right-ear earphone.

Referring to FIG. 16, the analog circuit 1610 is a bridge circuit. The bridge circuit includes the first impedance component 310a, being the impedance of the right-ear earphone, a second impedance 1622, a third impedance 1624, and a fourth impedance 1626. The second impedance 1622, the third impedance 1624, and the fourth impedance 1626 are fixed impedances. A fixed impedance is a circuit including at least one of a fixed resistor, a fixed inductor, or a fixed capacitor, or a combination thereof Given that the voltage of the first AC signal is $+e_i$, the voltage $+e_i$ of the first AC signal is input from the signal generator 130 to a first node (node a) between the second impedance 1622 and the third impedance 1624, and the first impedance 310a and the fourth impedance 1626 are grounded. In other words, a node c of the bridge circuit is grounded via the first impedance 310a, and a node d of the bridge circuit is grounded via the fourth impedance 1626. Accordingly, a sinusoidal voltage of the amplitude $e_i$ is input between the node a of the bridge circuit and ground points of the first impedance 310a and the fourth impedance 1626.

Likewise the analog circuit 1310 of FIG. 13, a voltage Δe between nodes c and d the analog circuit 1610 of FIG. 16 varies in proportion to the impedance variation Δr of the first impedance 310a due to detection of a bio-signal. Thus, the electronic device 100 according to the embodiment detects the voltage Δe proportional to Δr that originates from the bio-signal.

The differential amplifier 1322 detects the voltage Δe by taking a differential value between an input voltage at the node c between the second impedance 1622 and the first impedance 310a and an input voltage at the node d between the third impedance 1624 and the fourth impedance 1626. The differential amplifier 1322 amplifies the voltage Δe and inputs an amplified voltage Δe to the BPF 414. Subsequent processes are the same as those of FIGS. 4 and 11, and thus detailed descriptions thereof will be omitted.

According to the embodiment of the disclosure, the audio signal input from the audio player 1612 to the right-ear earphone is input between the second impedance 1622 and the first impedance 310a and is also input between the third impedance 1624 and the fourth impedance 1626.

The electronic device 100 according to the embodiment further includes a first buffer 1614, a second buffer 1616, a first resistor R11, a second resistor R12, and a third resistor R13.

According to an embodiment of the disclosure, the first resistor R11, the second resistor R12, and the third resistor R13 have the same resistance values. According to an embodiment of the disclosure, condensers or inductors may be used instead of the first resistor R11, the second resistor R12, and the third resistor R13. According to an embodiment of the disclosure, the first buffer 1614 and the second buffer 1616 are buffer circuits having the same structures and the same properties, for example, voltage follower circuits.

The audio player 1612 outputs an analog audio signal for right ears to the right-ear earphone via the first buffer 1614 and either the first resistor R11 or the second resistor R12. The audio player 1612 outputs an analog audio signal for left ears to the left-ear earphone via the second buffer 1616 and the third resistor R13. An output side of the first resistor R11 is coupled to the node c of the bridge circuit and an output side of the second resistor R12 is coupled to the node d of the bridge circuit. Accordingly, an audio signal input from the audio player 1612 to the right-ear earphone is input between the second impedance 1622 and the first impedance 310a and is also input between the third impedance 1624 and the fourth impedance 1626. In other words, the audio signal is added to the input voltage input from between the second impedance 1622 and the first impedance 310a to the differential amplifier 1322 and the input voltage input from between the third impedance 1624 and the fourth impedance 1626 to the differential amplifier 1322.

Because the differential amplifier 1322 takes a differential value between the input voltage at the node c between the second impedance 1622 and the first impedance 310a and the input voltage at the node d between the third impedance 1624 and the fourth impedance 1626, an audio signal included in the input voltage between the second impedance 1622 and the first impedance 310a and an audio signal included in the input voltage between the third impedance 1624 and the fourth impedance 1626 are offset by each other. Accordingly, an output of the differential amplifier 1322 does not include a voltage component originating from the audio signal, and thus biometric information may be detected more precisely.

Figure 17:
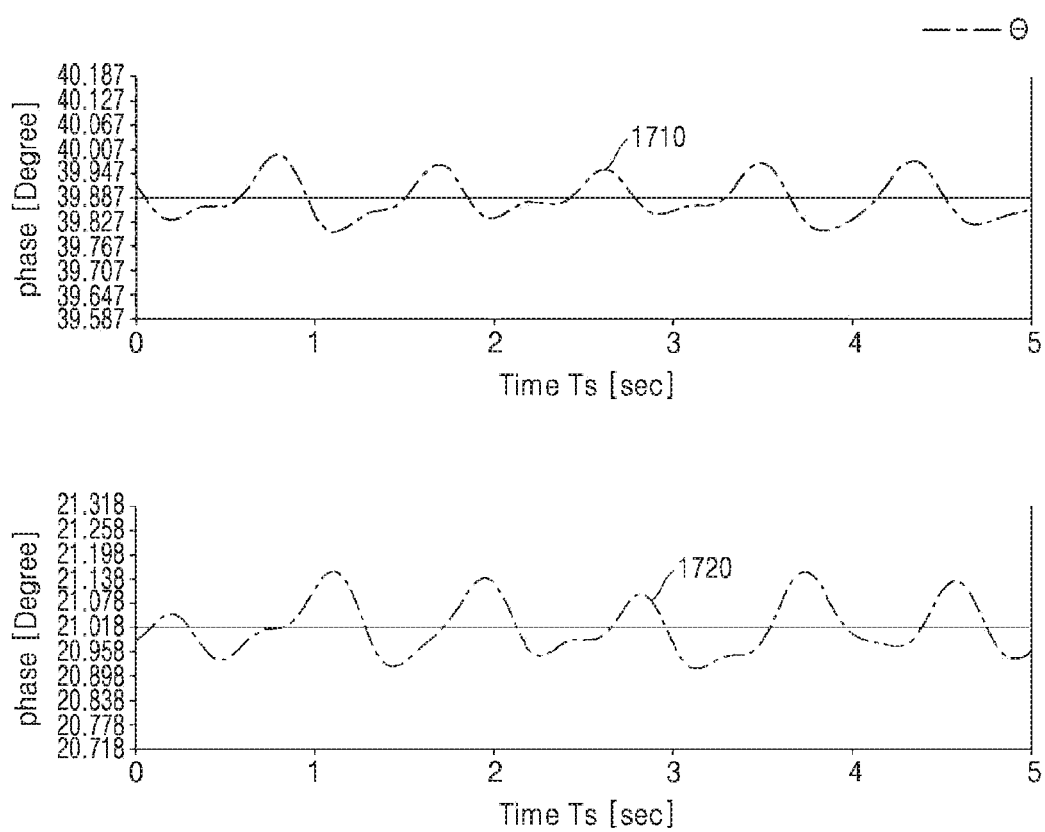
FIG. 17 illustrates a waveform of a detection signal of a pulse wave output by a processor of an electronic device when no audio signals are output by an audio player, and a waveform of a detection signal of a pulse wave output by the processor of the electronic device when an audio signal is output by the audio player according to an embodiment of the disclosure.

FIG. 17 illustrates an example 1710 of the waveform of a detection signal of a pulse wave output by a processor of an electronic device when no audio signals are output by an audio player, and an example 1720 of the waveform of a detection signal of a pulse wave output by the processor of the electronic device when an audio signal is output by the audio player according to an embodiment of the disclosure. The vertical axis of FIG. 17 indicates a phase (degree), and the horizontal axis thereof indicates time (second). One-dot dashed lines of FIG. 17 indicate the waveforms of the detection signals of the pulse waves.

Referring to FIG. 17, in the electronic device 100 of FIG. 16, even when an audio signal is output from the audio player 1612 to the right-ear earphone, the biometric information, such as a pulse may be detected to the same degree as that when no audio signals are output from the audio player 1612 to the right-ear earphone, based on the variation Δr of the impedance 310a of the right-ear earphone.

In the electronic device 100 of FIG. 16, the same effects as those of the electronic device 100 of FIG. 13 are obtained, and, when the differential amplifier 1322 takes a differential value between the input voltage between the second impedance 1622 and the first impedance 310a and the input voltage between the third impedance 1624 and the fourth impedance 1626, the audio signal included in the input voltage between the second impedance 1622 and the first impedance 310a and the audio signal included in the input voltage between the third impedance 1624 and the fourth impedance 1626 are offset by each other. Accordingly, an output of the differential amplifier 1322 does not include a voltage component originating from the audio signal, and thus biometric information may be detected more precisely.

To remove the voltage component originating from the audio signal, a HPF or the like using the predetermined frequency fi as a cutoff frequency, like the HPF 1510 of FIG. 15, is not needed between the audio player 1612 and the analog circuit 1610. Accordingly, degradation of the sound quality of an audio signal output by the earphone 110 due to the use of the HPF is prevented.

According to the embodiment of the disclosure, because the first resistor R11, the second resistor R12, and the third resistor R13 have the same resistance values and the first buffer 1614 and the second buffer 1616 are buffer circuits having the same structures and the same properties, a balance between a right-ear audio signal and a left-ear audio signal output by the audio player 1612 is maintained. Accordingly, a stereo audio signal may be output by the right-ear earphone and the left-ear earphone.

When the first buffer 1614 and the second buffer 1616 are, for example, voltage follower circuits, the impedance of an audio signal is transformed such that a current value of the audio signal is increased by the first buffer 1614 and the second buffer 1616. Accordingly, for example, even when the current value of the audio signal output by the audio player 1612 is not enough to drive the bridge circuit of the analog circuit 1610, the audio signal may be more securely added to the input voltages of the nodes c and d of the bridge circuit.

Figure 18:
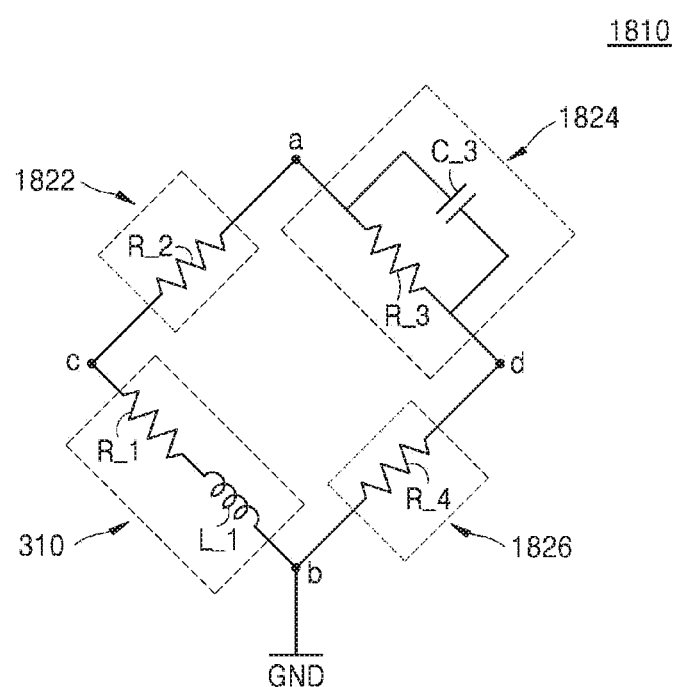
FIG. 18 illustrates an analog circuit according to an embodiment of the disclosure.

FIG. 18 illustrates an analog circuit according to an embodiment of the disclosure.

Figure 19:
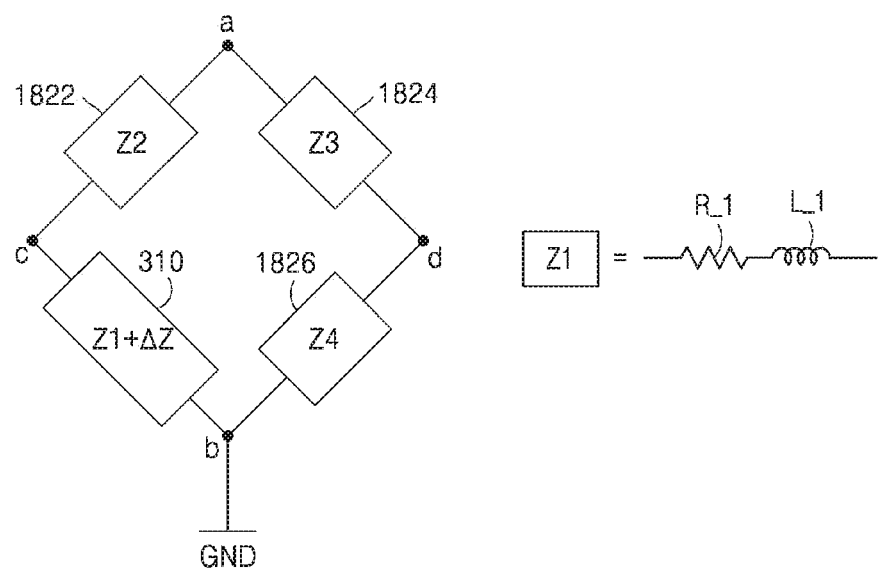
FIGS. 19 and 20 are circuit diagrams illustrating an analog circuit of FIG. 18 according to various embodiments of the disclosure.
Figure 20:
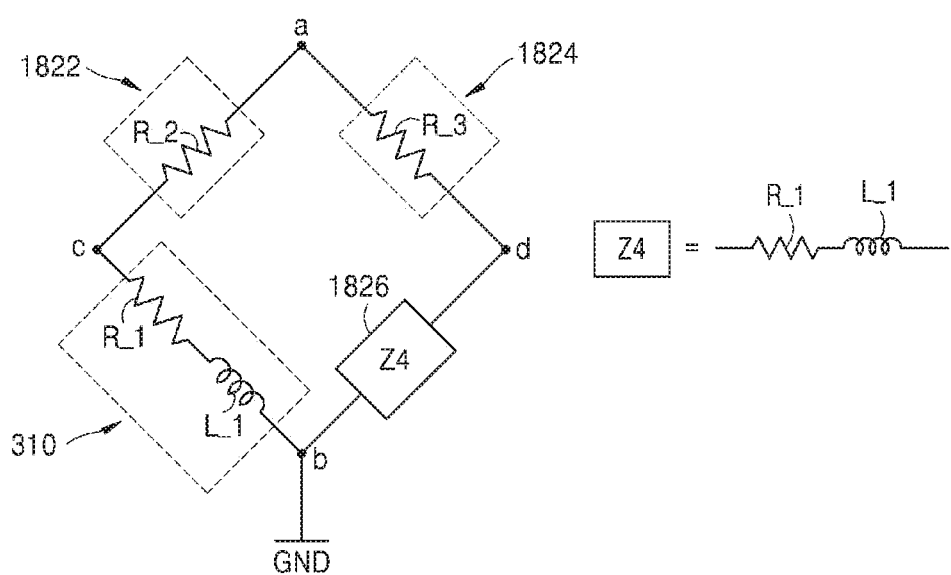

FIGS. 19 and 20 are circuit diagrams illustrating an analog circuit of FIG. 18 according to various embodiments of the disclosure.

Referring to FIG. 18, an analog circuit 1810 according to the embodiment is a modification of the analog circuit 1310 of FIG. 13.

In the analog circuit 1310 of FIG. 13, each of an impedance R1+Δr of the first impedance 310, an impedance R2 of the second impedance 1312, an impedance R3 of the third impedance 1314, and an impedance R4 of the fourth impedance 1316 is an impedance that may include an imaginary component. Accordingly, instead of R1+Δr, R2, R3, and R4 of FIGS. 13, Z1+Δz, Z2, Z3, and Z4 are used in FIGS. 19 and 20. Because the first impedance 310 is an impedance of the earphone 110, as shown in FIG. 19, the first impedance 310 may be expressed as a serial circuit between the resistance of a resistance value R_1 and the inductance of an inductance value L_1. For example, the resistance value R_1 is about several tens of Ω, and the inductance value L_1 is about several tens of μH to about several hundreds of μH.

In the analog circuit 1810, to satisfy a precondition Z1=Z4 of Equation 5, as shown in FIG. 20, a fourth impedance 1826 also needs to be formed as a serial circuit between the resistance of the resistance value R_1 and the inductance of the inductance value L_1.

Referring to FIG. 20, a second impedance 1822 may include a resistance having the resistance value R_2, and a third impedance 1824 may include a resistance having the resistance value R_3 that is the same as the resistance value R_2. In other words, the fourth impedance 1826 needs to be an impedance of an earphone 110 of the same product as the earphone 110 corresponding to the first impedance 310. However, when an earphone 110 of the same product as the earphone 110 corresponding to the first impedance 310 is prepared, costs are greatly increased, and it is difficult to mount the analog circuit 1810 on a small substrate that is used in mobile apparatuses. Thus, this case is unrealistic.

To satisfy Z1=Z4, a method of forming the fourth impedance 1826 with a resistance component and an inductance component may be considered. However, even when an inductance of several tens of μH is formed as a chip inductance, because it has a relatively large size, it is difficult to mount the analog circuit 1810 on a small substrate that is used in mobile apparatuses.

Accordingly, in the analog circuit 1810, as shown in FIG. 18, the first impedance 310 is formed as a serial circuit between the resistance of the resistance value R_1 and the inductance of the inductance value L_1, the second impedance 1822 is formed as the resistance having the resistance value R_2, the third impedance 1824 is formed as a parallel circuit between the resistance having the resistance value R_3 and a condenser of a capacity C_3, and the fourth impedance 1826 is formed as a resistance having the resistance value R_4.

Assuming that Z2/Z1=Z3/Z4 instead of Z1=Z4 and Z2=Z3, as an equilibrium condition of the bridge circuit being the analog circuit 1810, is satisfied, Equation 7 below is established.

$$\frac{R\_2}{R\_1 + j\omega L\_1} = \frac{R\_3}{R\_4 * (1 + j\omega C\_3 * R\_3)} \quad \text{Equation 7}$$

Respective equations for the real part and the imaginary part of Equation 7 are expressed as Equations 8 and 9, respectively.

$$\frac{R\_1 * R\_2}{R\_1^2 + (L\_1 * \omega)^2} = \frac{R\_3}{R\_4 + R\_4 * (C\_3 * R\_3 * \omega)^2} \quad \text{Equation 8}$$

$$\frac{L\_1 * R\_2 * \omega}{R\_1^2 + (L\_1 * \omega)^2} = \frac{C\_3 * R\_3^2 * \omega}{R\_4 + R\_4 * (C\_3 * R\_3 * \omega)^2} \quad \text{Equation 9}$$

For example, when α is a positive real number, given that R_1=α*R_4, R_2=α*R_3, and C_3=L_1/(α*R_3*R_4), Equations 8 and 9 become identical equations for a frequency ω, and the analog circuit 1810 may satisfy Equations 8 and 9 with respect to any frequency ω. Accordingly, the analog circuit 1810 may realize an equilibrium having a high detection sensitivity.

According to the embodiment described above, in the electronic device 100 of FIG. 13, the analog circuit 1810 may be formed with a cheap and small capacity component rather than an expensive and large additional earphone 110 or inductor component, and the analog circuit 1810 may realize an equilibrium state having a high detection sensitivity.

According to the embodiment of the disclosure, a modification of the analog circuit 1310 of FIG. 13 has been described. However, the same modification may be made to the analog circuit 1110 of FIG. 11.

Figure 21:
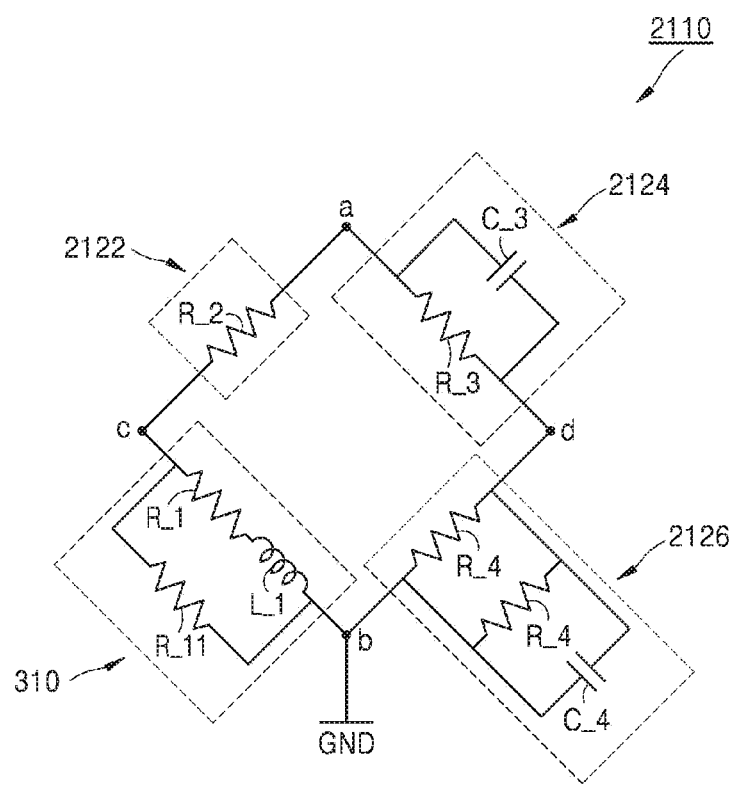
FIG. 21 illustrates an analog circuit according to an embodiment of the disclosure.

FIG. 21 illustrates an analog circuit according to an embodiment of the disclosure.

Referring to FIG. 21, an analog circuit 2110 according to the embodiment is a modification of the analog circuit 1610 of FIG. 16. In FIG. 16, an output of the first buffer 1614 to which the first resistor R11 and the second resistor R12 are coupled is grounded, and an output impedance of the first buffer 1614 is assumed to be nearly 0 Ω. Accordingly, the analog circuit 1610 of FIG. 16 is replaced by an equivalent circuit (analog circuit 2110) shown in FIG. 21. In FIG. 21, the resistance values R4, R11, and R12 of the fourth impedance 1626, the first resistor R11, and the second resistor R12 of FIG. 16 are a resistance value R_4, a resistance value R_11, and a resistance value R_14, respectively. Likewise the embodiment of FIG. 18, each of the impedances R1, R2, R3, and R4 of the first impedance 310, the second impedance 1622, the third impedance 1624, and the fourth impedance 1626 is an impedance that may include an imaginary component. Thus, in the embodiment of FIGS. 21, Z1, Z2, Z3, and Z4 are used instead of R1, R2, R3, and R4 of FIG. 16.

In the analog circuit 2110, a first impedance 310 is formed as a parallel circuit between a resistance of the resistance value R_1 and an inductance of the inductance value L_1 serially connected to each other and a resistance of the resistance value R_11, a second impedance 2122 is formed as a resistance having the resistance value R_2, a third impedance 2124 is formed as a parallel circuit between a resistance having the resistance value R_3 and a condenser of a capacity C_3, and a fourth impedance 2126 is formed as a parallel circuit between a resistance having the resistance value R_4 and a condenser of a capacity C_4.

Likewise the embodiment of FIG. 18, assuming that Z2/Z1=Z3/Z4 instead of Z1=Z4 and Z2=Z3, as an equilibrium condition of a bridge circuit being the analog circuit 2110, is satisfied, Equation 10 below is established.

$$\frac{R\_2}{(R\_1 + j\omega L\_1) // R\_11} = \frac{R\_3}{(R\_4 // R\_14 // 1 / j\omega C\_4) * (1 + j\omega C\_3 * R\_3)} \quad \text{Equation 10}$$

Respective equations for the real part and the imaginary part of Equation 10 are expressed as Equations 11 and 12, respectively.

$$\frac{R\_2 * ((R\_1 + R\_11) * R\_1 + (L\_1 * \omega)^2)}{R\_11 * (R\_1^2 + (L\_1 * \omega)^2)} = \frac{R\_3 * ((R\_4 + R\_14 + R\_4 * R\_14 * C\_3 * C\_4 * R\_3 * \omega^2))}{R\_4 * R\_14 * (1 + (C\_3 * R\_3 * \omega)^2)} \quad \text{Equation 11}$$

$$\frac{-R\_2 * R\_11 * L\_1 * \omega}{R\_11 * (R\_1^2 + (L\_1 * \omega)^2)} = \frac{-R\_3 * ((R\_4 + R\_14) * C\_3 * R\_3 * -R\_4 * R\_14 * C\_4) * \omega}{R\_4 * R\_14 * (1 + (C\_3 * R\_3 * \omega)^2)} \quad \text{Equation 12}$$

For example, when $\alpha$ is a positive real number, given that R_1=$\alpha$*R_4, R_2=$\alpha$*R_3, R_11=$\alpha$*R_14, C_3=L_1/($\alpha$*R_3*R_4), and C_4=L_1/($\alpha$*R_4*R_14), Equations 11 and 12 become identical equations for a frequency $\omega$, and the analog circuit 2110 may satisfy Equations 11 and 12 with respect to any frequency $\omega$. Accordingly, the analog circuit 2110 may realize an equilibrium having a high detection sensitivity.

According to the embodiment described above, in the electronic device 100 of FIG. 16, the analog circuit 2110 may be formed with a cheap and small capacity component rather than an expensive and large additional earphone 110 or inductor component, and the analog circuit 2110 may realize an equilibrium state having a high detection sensitivity.

Figure 22:
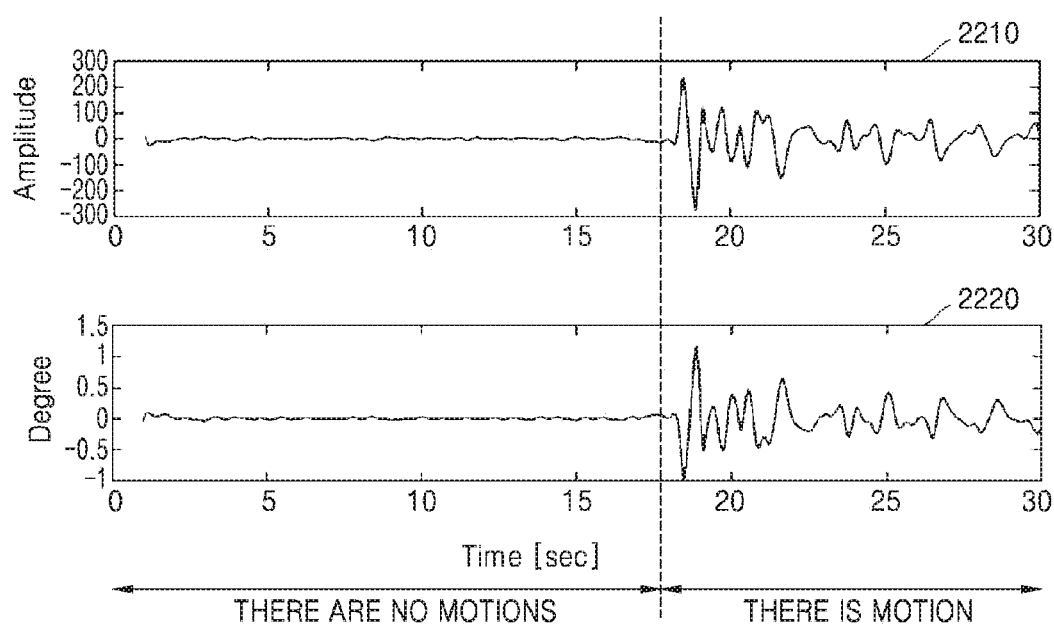
FIG. 22 illustrates amplitude and phase information of a detection signal according to an embodiment of the disclosure.

FIG. 22 illustrates amplitude and phase information of a detection signal according to an embodiment of the disclosure.

Figure 23:
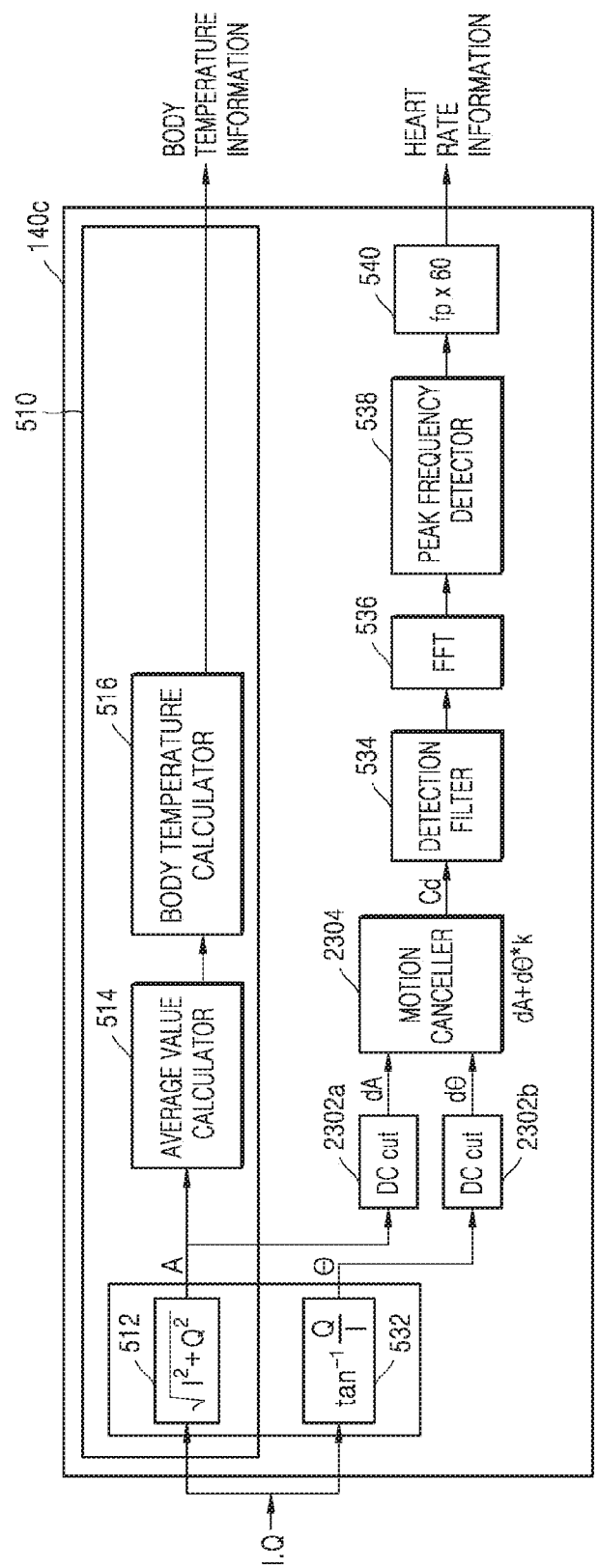
FIG. 23 is a block diagram of a processor according to an embodiment of the disclosure.

FIG. 23 is a block diagram of a processor according to an embodiment of the disclosure.

Figure 24:
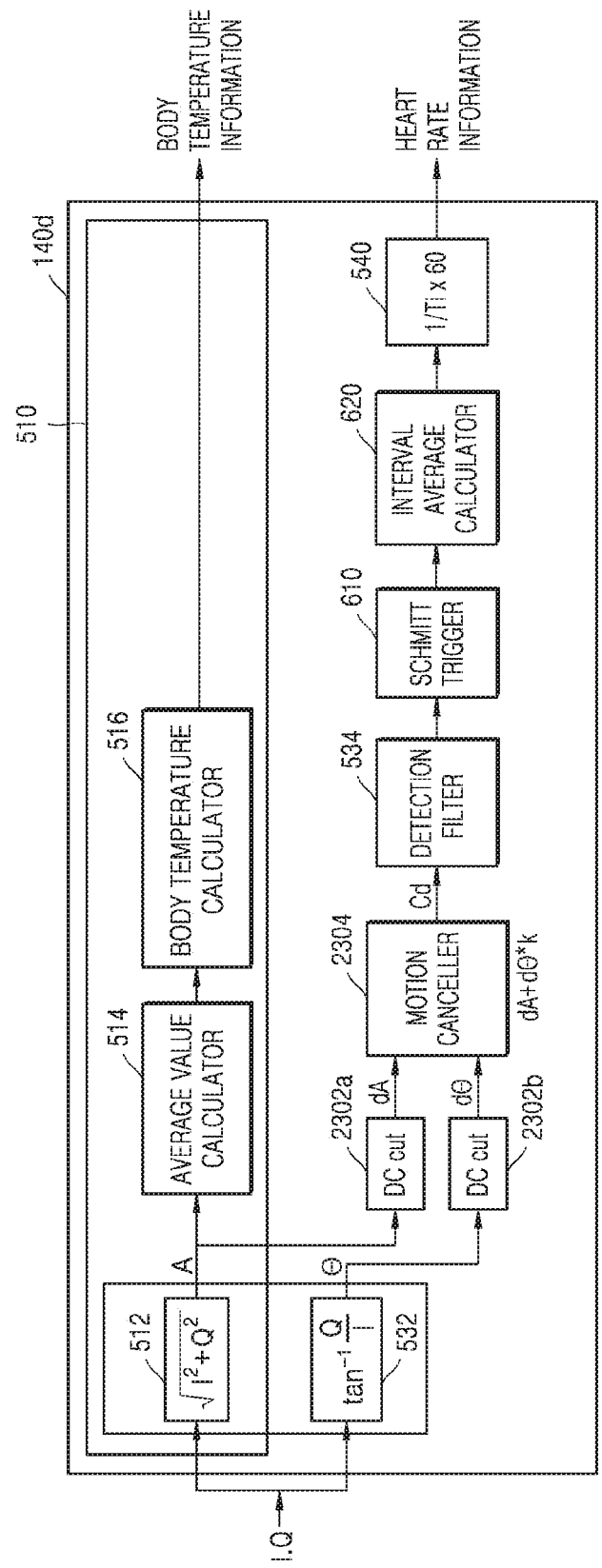
FIG. 24 is a block diagram of a processor according to an embodiment of the disclosure.

FIG. 24 is a block diagram of a processor according to an embodiment of the disclosure.

Compared with the processor 140a of FIG. 5, a processor 140c of FIG. 23 is different from the processor 140a of FIG. 5 in that DC component cutters 2302a and 2302b and a motion canceller 2304 are included. The processor 140d of FIG. 24 is different from the processor 140b of FIG. 6 in that the DC component cutters 2302a and 2302b and the motion canceller 2304 are included. Like reference numerals or characters are assigned to components of the electronic devices 100 of FIGS. 23 and 24 corresponding to those of the electronic devices 100 of FIGS. 5 and 6, and repeated descriptions thereof will be omitted.

In bio-signal detection, in particular, pulse wave detection, in the electronic devices 100 of FIGS. 5 and 6, a pulse wave component included in a detection signal is very weak. Accordingly, bio-signal detection in the electronic devices 100 of FIGS. 5 and 6 is easily influenced by a signal originating from a motion (body motion) of an examinee. FIG. 22 illustrates an amplitude graph 2210 showing an influence of a motion of an examinee with respect to an amplitude component, and a phase graph 2220 showing an influence of the motion of the examinee with respect to a phase component. In the amplitude graph 2210 of FIG. 22, the vertical axis indicates the amplitude size of a DC-cut amplitude component dA obtained by the DC component cutter 2302a of FIGS. 23 and 24, and the horizontal axis indicates time (second). In the phase graph 2220 of FIG. 22, the vertical axis indicates a DC-cut phase d$\theta$ obtained by the DC component cutter 2302b of FIGS. 23 and 24, and the horizontal axis indicates time (second). In FIG. 22, data when there are no motions of an examinee is shown until about 18 seconds, and data when there is a motion of the examinee is shown after about 18 seconds.

Referring to FIG. 22, variations in the DC-cut amplitude component dA and the DC-cut phase component d$\theta$ according to motions of the examinee are significantly greater than variations in the DC-cut amplitude component dA and the DC-cut phase component d$\theta$ according to a pulse wave of the examinee. Accordingly, when there is a motion of the examinee, it is difficult to extract a pulse wave of the examinee from the DC-cut amplitude component dA and the DC-cut phase component d$\theta$ of the detection signal.

Referring to FIGS. 23 and 24, the processors 140c and 140d remove a signal caused by a motion of the examinee.

The DC component cutter 2302a removes a DC component including a long-period variation caused by a temperature (body temperature) from the amplitude component A calculated by the amplitude calculator 512. Likewise, the DC component cutter 2302b removes a DC component including a long-period variation caused by a temperature (body temperature) from the phase component $\theta$ calculated by the phase calculator 532.

The motion canceller 2304 removes a motion component of the examinee from the DC-cut amplitude component dA obtained by the DC component cutter 2302a, according to Equation 13 below.

Likewise, the motion canceller 2304 removes a motion component of the examinee from the DC-cut phase component d$\theta$ obtained by the DC component cutter 2302b, according to Equation 13 below.

The motion canceller 2304 outputs, as a signal Cd, an amplitude component from which the motion component has been removed and a phase component from which the motion component has been removed.

$$Cd = dA + d\theta * k \quad \text{Equation 13}$$

where k is a fixed parameter representing a ratio between the amplitude component A and the phase component $\theta$, and is pre-defined by a circuit constant of the electronic device 100 or an operating point of a circuit.

Figure 25:
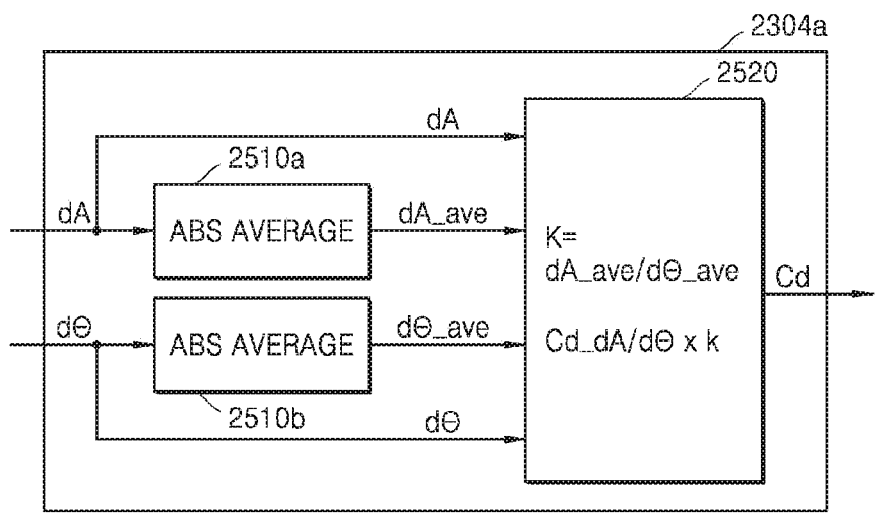
FIG. 25 is a block diagram of a structure of a motion canceller according to an embodiment of the disclosure.

FIG. 25 is a block diagram of a structure of a motion canceller according to an embodiment of the disclosure.

Referring to FIG. 25, a motion canceller 2304a calculates the fixed parameter k of Equation 13 from an average value of the DC-cut amplitude component dA and the DC-cut phase component d$\theta$. The motion canceller 2304a calculates an ABS average being an average value of the DC-cut amplitude component dA for a certain time period (indicated by reference numeral 2510a), and calculates an ABS average being an average value of the DC-cut phase component d$\theta$ for a certain time period (indicated by reference numeral 2510b). Next, the motion canceller 2304a calculates the fixed parameter k according to Equation 14 below (indicated by reference numeral 2520).

$$k = dA\_\text{ave}/d\theta\_\text{ave} \quad \text{Equation 14}$$

where dA_ave indicates the average value of the DC-cut amplitude component dA for a certain time period, and d$\theta$_ave indicates the average value of the DC-cut phase component d$\theta$ for a certain time period.

In the motion canceller 2304a of FIG. 25, due to dynamic calculation of an optimal fixed parameter k, even when an operating point of a circuit varies according to circumstances, the motion component may be removed based on the dynamically calculated optimal fixed parameter k.

Figure 26:
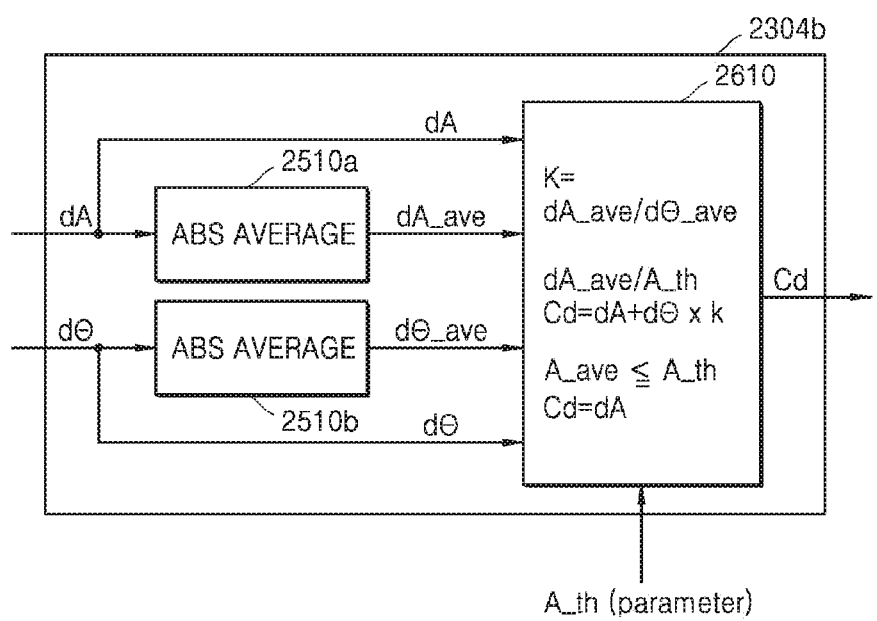
FIG. 26 is a block diagram of a structure of a motion canceller according to an embodiment of the disclosure.

FIG. 26 is a block diagram of a structure of a motion canceller according to an embodiment of the disclosure.

Referring to FIG. 26, a motion canceller 2304b removes a motion component from the DC-cut amplitude component dA and the DC-cut phase component dθ, only when a motion is detected. For example, in reference numeral 2610, when the average value dA_ave of the DC-cut amplitude component dA exceeds a pre-defined threshold value A_th, the motion canceller 2304b removes a motion component from the DC-cut amplitude component dA and the DC-cut phase component dθ according to Equation 13. Likewise, when the average value dθ_ave of the DC-cut phase component dθ exceeds a pre-defined threshold value θ_th, the motion canceller 2304b removes a motion component from the DC-cut amplitude component dA and the DC-cut phase component dθ according to Equation 13. In FIG. 26, k in Equation 13 is calculated according to Equation 14. However, according to another embodiment of the disclosure, k may be pre-defined by the circuit constant of the electronic device 100 or the operating point of the circuit.

Figure 27:
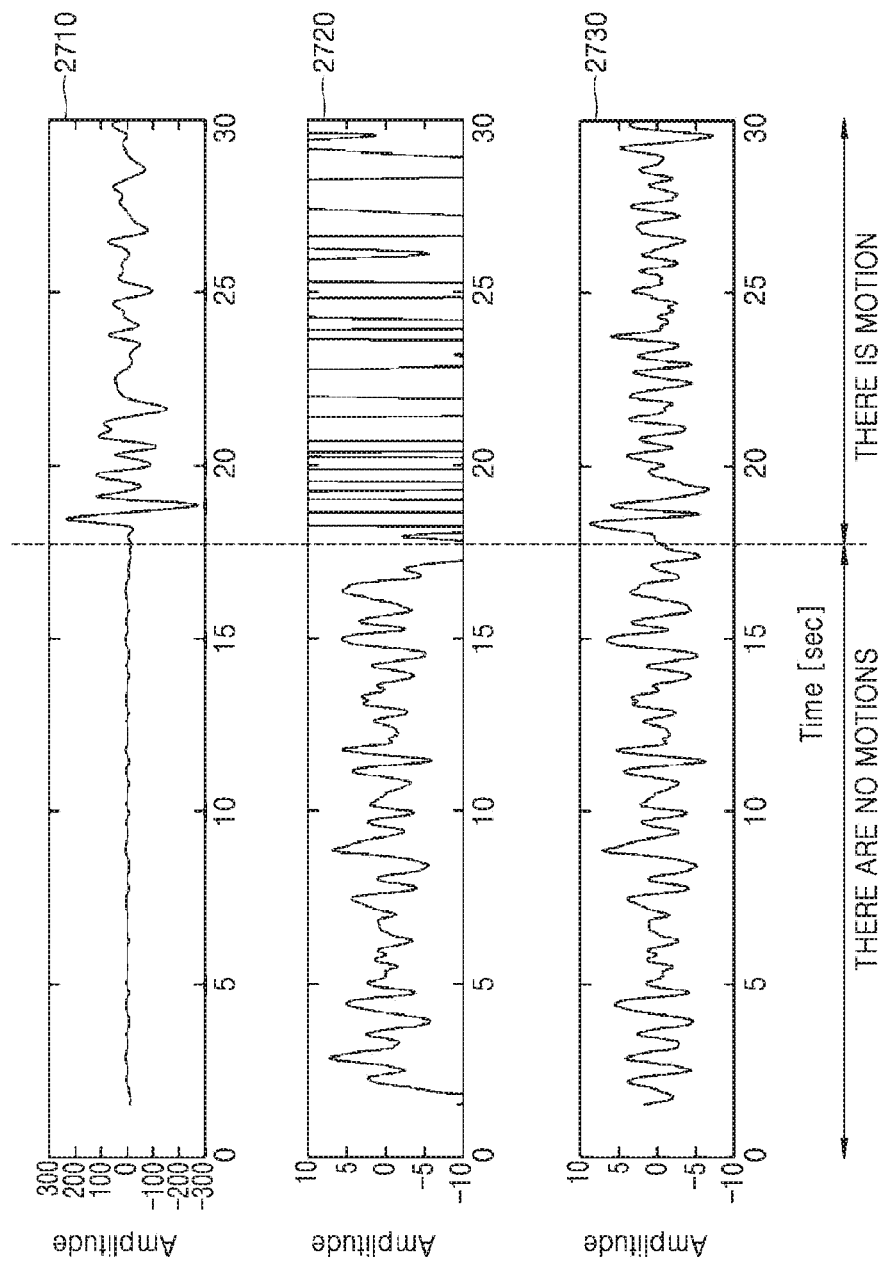
FIG. 27 illustrates a result of removal of a motion component by a motion canceller of FIG. 26 according to an embodiment of the disclosure.

FIG. 27 illustrates a result of removal of a motion component by a motion canceller of FIG. 26 according to an embodiment of the disclosure.

Referring to FIG. 27, a graph 2710 shows the DC-cut amplitude component dA output by the DC component cutter 2302a before the motion component is removed, and a graph 2720 shows a magnification of the vertical axis scale of the graph 2710 by 30 times. A graph 2730 shows the DC-cut amplitude component dA from which the motion component has been removed by the motion canceller 2304b. As shown in the graphs 2710 and 2720 of FIG. 27, a waveform caused by a wave pulse of an examinee is observed in a no-motion interval where there are no motions (until about 18 seconds), whereas a waveform caused by a motion of the examinee is big in a motion interval where there is a motion (after about 18 seconds), and thus the waveform caused by the wave pulse of the examinee is not observed. However, as shown in the graph 2730 of FIG. 27, when the motion component is removed by the motion canceller 2304b, the waveform caused by the wave pulse of the examinee may be observed even in the motion interval to the same degree as that in the no-motion interval. Referring to FIG. 27, it may be seen that the motion component has been properly removed from the DC-cut amplitude component dA by the motion canceller 2304b.

Figure 28:
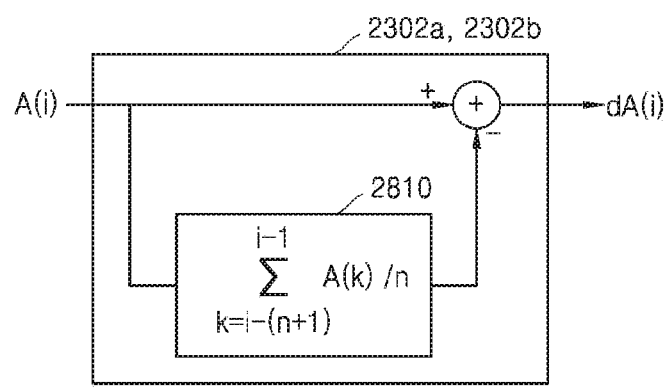
FIG. 28 illustrates direct current (DC) component cutters according to an embodiment of the disclosure.

FIG. 28 illustrates DC component cutters according to an embodiment of the disclosure.

Referring to FIG. 28, DC component cutters 2302a and 2302b remove a DC component of an input signal A(i) by subtracting an average value of input signals A(i) of past n samples from the input signal A(i). For example, the DC component cutters 2302a and 2302b calculate the average value of the input signals A(i) of the past n samples according to Equation 15 below, and remove the DC component from the input signal A(i). The DC component cutters 2302a and 2302b output a DC-cut signal dA(i).

$$\text{(Average value of } A(i) \text{ past } n \text{ samples)} = \sum_{k=i-(n+1)}^{i-1} A(k)/n \quad \text{Equation 15}$$

Figure 29:
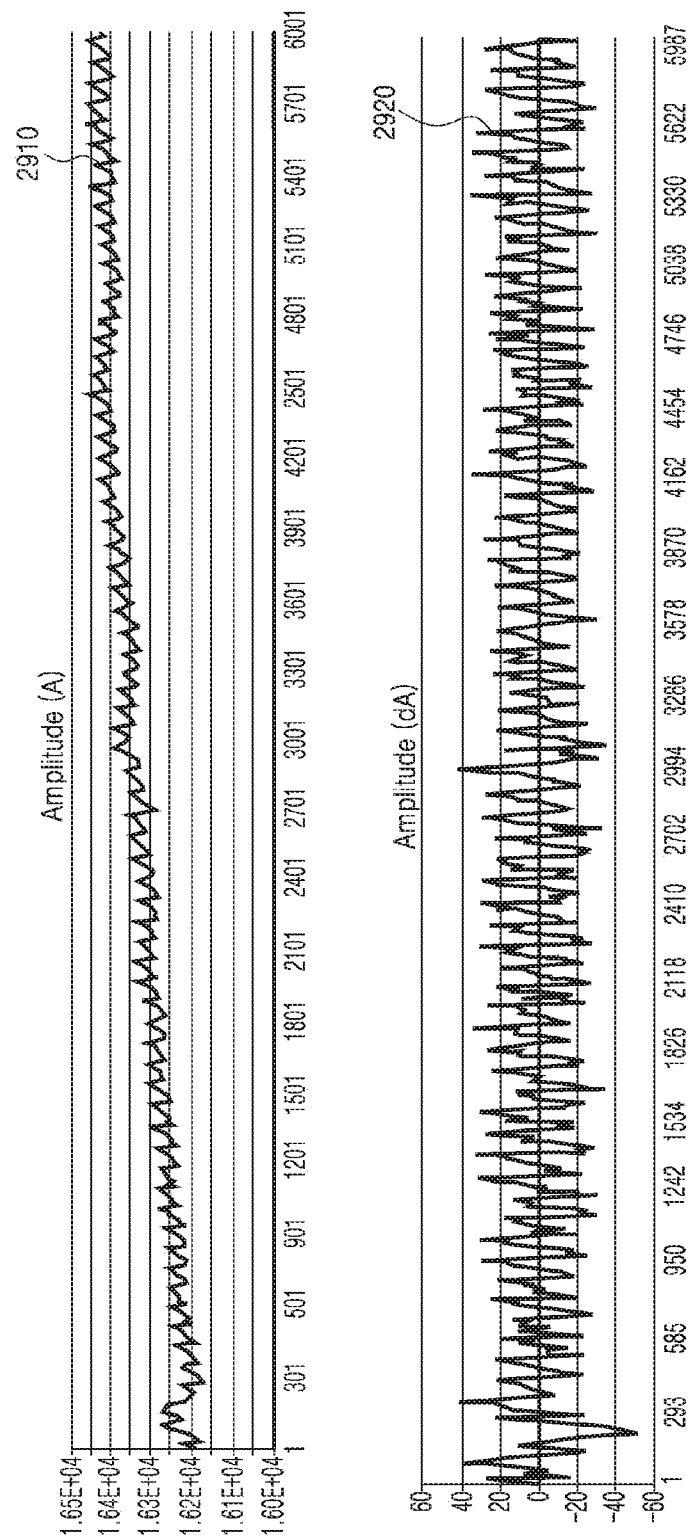
FIG. 29 illustrates a waveform of an amplitude component from which a DC component has not yet been removed, and a waveform of a DC-cut amplitude component from which the DC component has been removed according to an embodiment of the disclosure.

FIG. 29 illustrates a waveform of an amplitude component A from which a DC component has not yet been removed, and a waveform of a DC-cut amplitude component dA from which the DC component has been removed according to an embodiment of the disclosure.

Referring to FIG. 29, the vertical axis indicates an amplitude, and the horizontal axis thereof indicates the number of samples. In the horizontal axis of FIG. 29, one sample corresponds to 1/100 second. In other words, the horizontal axis of FIG. 29 indicates time. FIG. 29 illustrates respective waveforms of the amplitude component A and the DC-cut amplitude component dA during 0 to 60 seconds.

Referring to FIG. 29, as shown in a waveform 2910 of the amplitude component A from which the DC component has not yet been removed, the DC component temporally changes. However, even in this case, as shown in a waveform 2920 of the DC-cut amplitude component dA from which the DC component has been removed, the DC component cutters 2302a and 2302b may properly remove the DC component from the amplitude component A.

The value of n in Equation 15 above needs to be the number of samples within an interval that is longer than the period of a signal to be detected. For example, when a pulse is detected, n needs to be the number of samples that is greater than the number of samples for one second. For example, when a sampling frequency is 100 Hz, n needs to be 100 or greater. When n is too large, an action to a case where the DC component has changed is late, and thus a removable DC component is reduced. Accordingly, the value of n is suitably, for example, about 100 to about 200.

Figure 30:
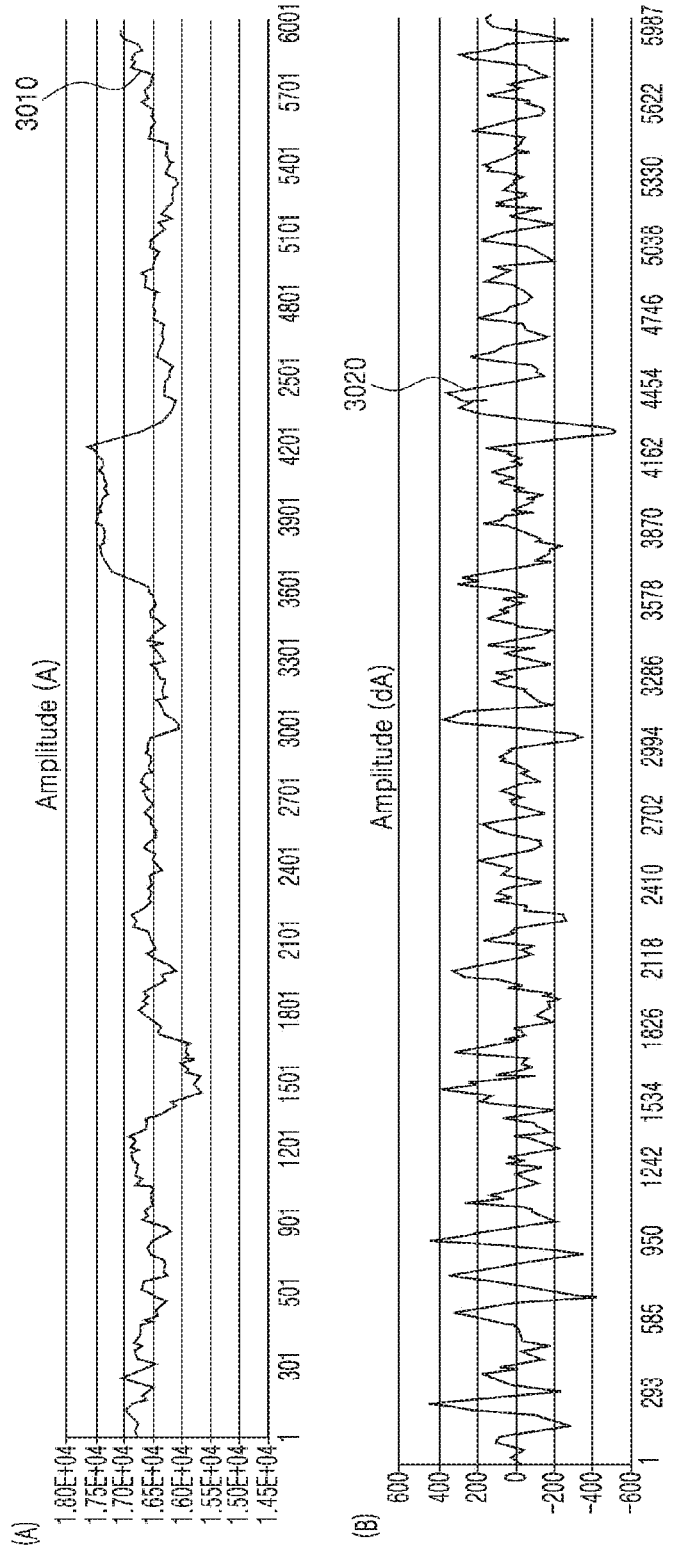
FIG. 30 illustrates a result of a removal of a DC component by DC component cutters of FIG. 28 according to an embodiment of the disclosure.

FIG. 30 illustrates a result of a removal of a DC component by DC component cutters according to an embodiment of the disclosure.

Referring to FIG. 30, a graph 3010 is illustrated of the amplitude component A from which the DC component has not yet been removed, and a graph 3020 of the DC-cut amplitude component dA from which the DC component has been removed. The vertical axis of FIG. 30 indicates an amplitude, and the horizontal axis thereof indicates the number of samples. In the horizontal axis of FIG. 30, one sample corresponds to 1/100 second. In other words, the horizontal axis of FIG. 30 indicates time. FIG. 30 illustrates respective waveforms of the amplitude component A from which the DC component has not yet been removed and the DC-cut amplitude component dA for 0 to 60 seconds. The amplitude component A shown in the graph 3010 of FIG. 30 includes not only the DC component but also a variation in the DC component according to a relatively gentle motion of an examinee.

Referring to FIG. 30, the graph 3020 not only the DC component but also the variation in the DC component according to the relatively gentle motion of the examinee have been removed from the amplitude component A by the DC component cutters 2302a and 2302b. Thus, according to an embodiment of the disclosure, the processor 140 may not include the motion canceller 2304, and may remove the motion component from the amplitude component A and the phase component θ by using the DC component cutters 2302a and 2302b.

All of the processors 140a and 140b of FIGS. 5 and 6 and the processors 140c and 140d of FIGS. 23 and 24 include the detection filter 534. The detection filter 534 is a BPF using a frequency including a desired bio-signal (for example, a pulse) as a central frequency, and, in the case of a phase component, removes a noise component and emphasizes a desired frequency (for example, the frequency of a pulse). According to embodiments of the disclosure, a motion component may be effectively removed by optimizing the frequency characteristics of the detection filter 534. For example, by optimizing the frequency characteristics of the detection filter 534 such that a low frequency component where a motion easily occurs, for example, a frequency component of about 0.5 Hz or less, is attenuated and about 1 Hz to about 2 Hz being a frequency component of a pulse wave is emphasized, a desired bio-signal component may be emphasized and also a motion component may be removed.

The processors 140a and 140b of FIGS. 5 and 6 perform pulse detection from the phase component θ, and may also perform pulse detection from the amplitude component A. The amplitude component A and the phase component θ have slightly different waveforms, but pulse detection from the amplitude component A and pulse detection from the phase component θ may be performed according to the same method. Pulse detection from the amplitude component A may be performed by optimizing the frequency characteristics of the detection filter 534 of FIG. 5 or 6 or a threshold value of the Schmitt trigger 610.

In the above-described electronic device 100 according to another embodiment of the disclosure, the same effects as those of the electronic device 100 of FIG. 5 or 6, or the electronic device 100 of FIG. 4, 11, 14, 15, 16, 18, or 21 may be obtained, and the motion canceller 2304 may remove the motion component of an examinee from an amplitude component and a phase component. Accordingly, the electronic device 100 according to the embodiment may detect a weak bio-signal with a high precision even when the examinee is moving.

Next, another embodiment of the disclosure will be described with reference to FIGS. 31 through 44.

Figure 31:
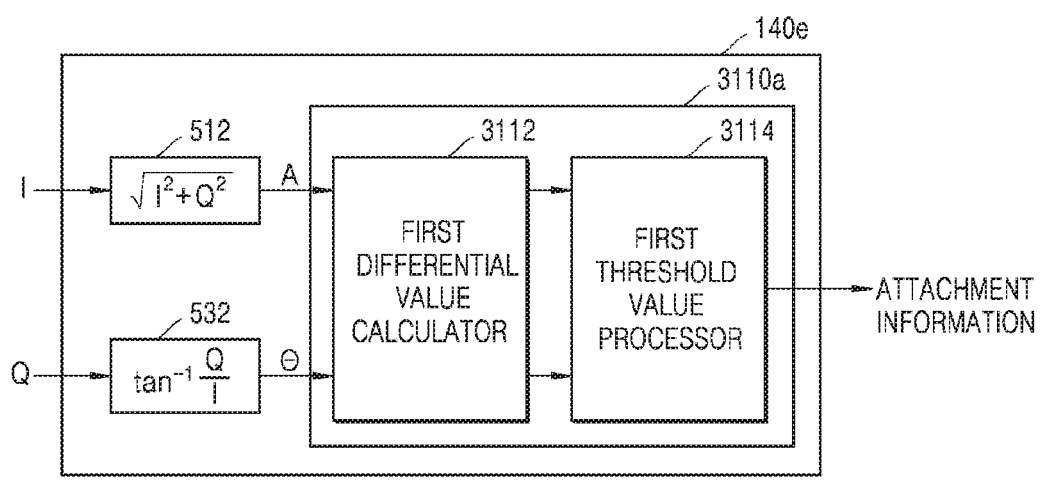
FIG. 31 is a block diagram of a processor according to an embodiment of the disclosure.
Figure 38:
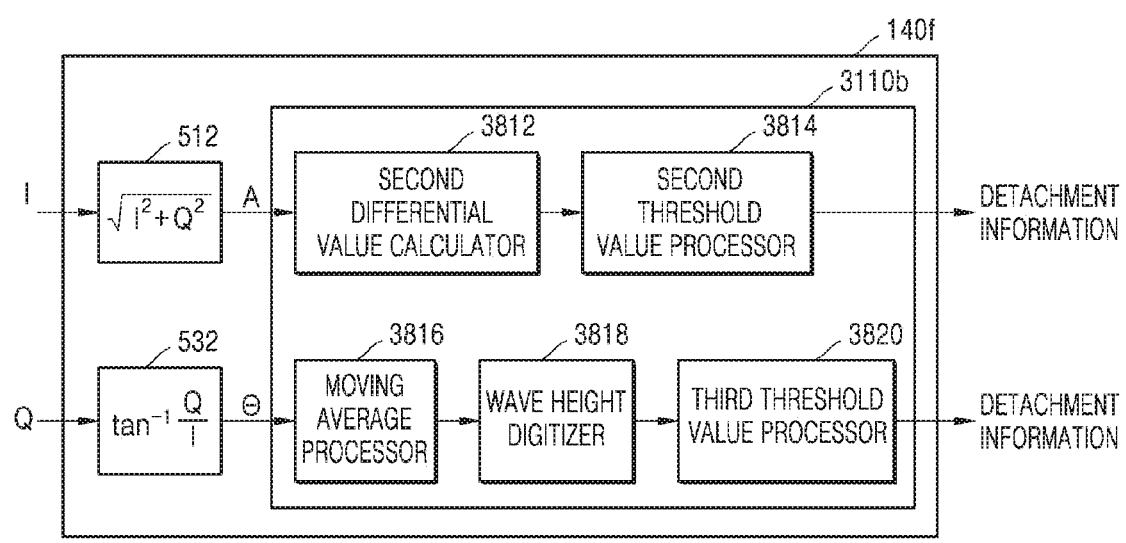
FIG. 38 is a block diagram of a processor according to an embodiment of the disclosure.

In the electronic device 100, as shown in FIGS. 31 and 38, processors 140e and 140f have different structures from the processor 140a, 140b, 140c, or 140d of FIG. 5, 6, 23, or 24.

Referring to FIGS. 31 and 38, the processors 140e and 140f include an attachment detector 3110a of the earphone 110 and a detachment detector 3110b of the earphone 110, respectively. In the electronic device 100, a biometric information calculator 112 may include at least one of the attachment detector 3110a of the earphone 110 or the detachment detector 3110b of the earphone 110. The other components of the electronic device 100 according to the embodiment may be the same as those of the processor 140a, 140b, 140c, or 140d of FIG. 5, 6, 23, or 24, or the components of FIG. 31 or 38 may be combined with the components of the processor 140a, 140b, 140c, or 140d. Like reference numerals or characters are assigned to components of FIG. 31 or 38 corresponding to those of FIG. 5, 6, 23, or 24, and detailed descriptions thereof will be omitted.

FIG. 31 is a block diagram of a processor 140e according to an embodiment of the disclosure.

The processor 140e of FIG. 31 may further include the attachment detector 3110a in addition to the components of the embodiment of FIG. 5, 6, 23, 24, or 38. The attachment detector 3110a includes a first differential value calculator 3112 and a first threshold value processor 3114.

FIG. 38 is a block diagram of a processor 140f according to an embodiment of the disclosure.

The processor 140f of FIG. 38 may further include the detachment detector 3110b in addition to the components of the embodiment of FIG. 5, 6, 23, 24, or 31.

Referring to FIG. 38, the detachment detector 3110b includes a second differential value calculator 3812, a second threshold value processor 3814, a moving average processor 3816, a wave height digitizer 3818, and a third threshold value processor 3820.

The other components of the processors 140e and 140f of FIGS. 31 and 38 are the same as those of the processor 140a, 140b, 140c, or 140d of FIG. 5, 6, 23, or 24, and thus illustrations thereof are omitted. The electronic device 100 according to the embodiment detects attachment and detachment of the earphone 110 by an examinee by using the analog circuit 1110, 1310, 1520, 1610, 1810, or 2110 of FIG. 4, 11, 13, 15, 16, 18, or 21. An in-phase component I and a quadrature phase component Q are generated from the voltage Δe output by the analog circuit 1110, 1310, 1520, 1610, 1810, or 2110 through the BPF 414, the ADC 416, and the orthogonal demodulator 420. The in-phase component I and the quadrature phase component Q are input to the processors 140e and 140f. In the description below, the amplitude component A is calculated from the in-phase component I by the amplitude calculator 512 of the processors 140e and 140f, and the phase component θ is calculated from the quadrature phase component Q by the phase calculator 532 of the processors 140e and 140f.

First, detection of attachment of the earphone 110 to an examinee will be described.

Figure 32:
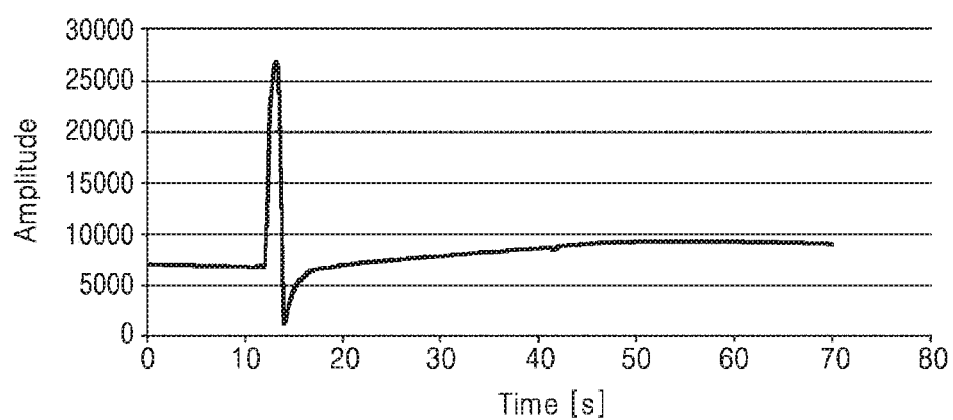
FIG. 32 illustrates a change, over time, in an amplitude component generated by a processor when an examinee wears an earphone according to an embodiment of the disclosure.

FIG. 32 illustrates a change, over time, in an amplitude component A generated by a processor when an examinee wears an earphone according to an embodiment of the disclosure.

Figure 33:
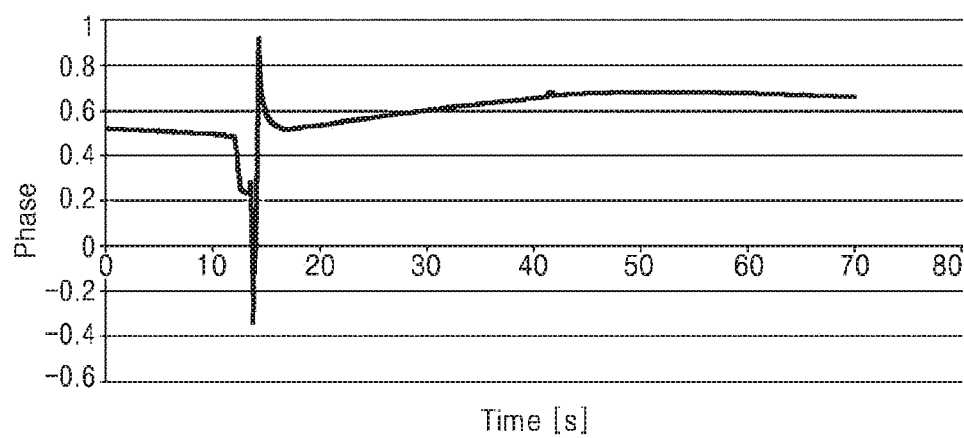
FIG. 33 illustrates a change, over time, in a phase component generated by a processor when an examinee wears an earphone according to an embodiment of the disclosure.

FIG. 33 illustrates a change, over time, in a phase component θ generated by a processor when an examinee wears an earphone according to an embodiment of the disclosure. The vertical axis of FIG. 32 indicates an amplitude, and the horizontal axis thereof indicates time (second). The vertical axis of FIG. 33 indicates a phase, and the horizontal axis thereof indicates time (second).

Referring to FIGS. 32 and 33, the amplitude component A and the phase component θ greatly changed at about 10 seconds, and at this time the examinee attached the earphone 110 to his or her ears. To more emphasize the changes in the amplitude component A and the phase component θ, the first differential value calculator 3112 performs time differentiation with respect to the amplitude component A and the phase component θ.

The first differential value calculator 3112 holds the amplitude component A calculated by the amplitude calculator 512 and the phase component θ calculated by the phase calculator 532, by a certain number of frames. The holding may be performed by using, for example, a buffer, a register, or a capacitor. For example, the first differential value calculator 3112 holds the amplitude component A and the phase component θ by 100 frames. When each frame is obtained with 100 Hz, 100 frames are the amount corresponding to one second.

Then, the first differential value calculator 3112 calculates an average value of first-half 50 frames among the held 100 frames and an average value of second-half 50 frames among the held 100 frames, and calculates a differential value by subtracting the average value of the first-half 50 frame from the average value of the second-half 50 frames.

The first differential value calculator 3112 repeats this process to perform time differentiation with respect to the amplitude component A and the phase component θ.

The number of held frames is appropriately determined according to a sampling rate of the in-phase component I and the quadrature phase component Q input to the processor 140e, and may be, for example, 1 frame or 1000 frames.

Figure 34:
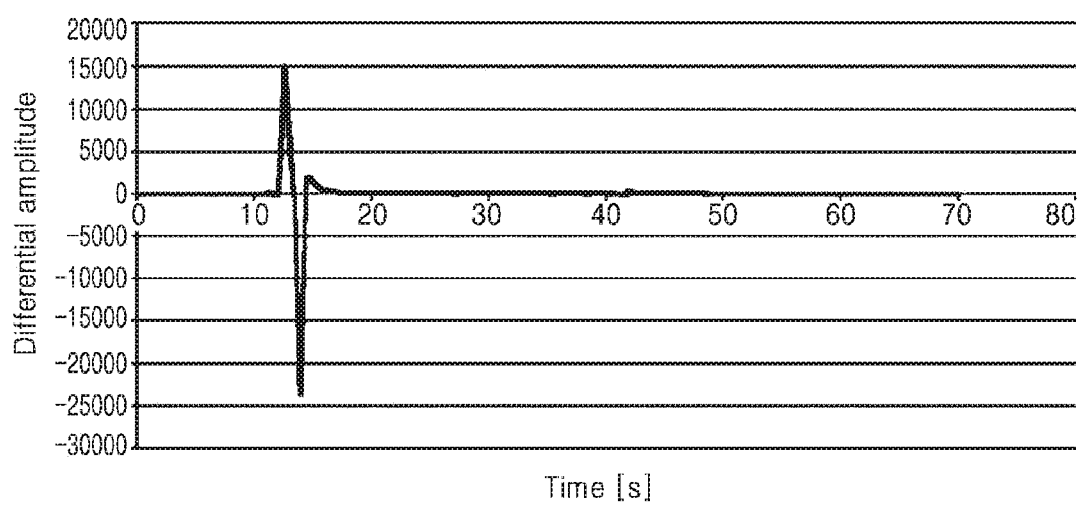
FIG. 34 illustrates a result of time differentiation with respect to an amplitude component according to an embodiment of the disclosure.

FIG. 34 illustrates a result of a time differentiation with respect to an amplitude component A according to an embodiment of the disclosure.

Figure 35:
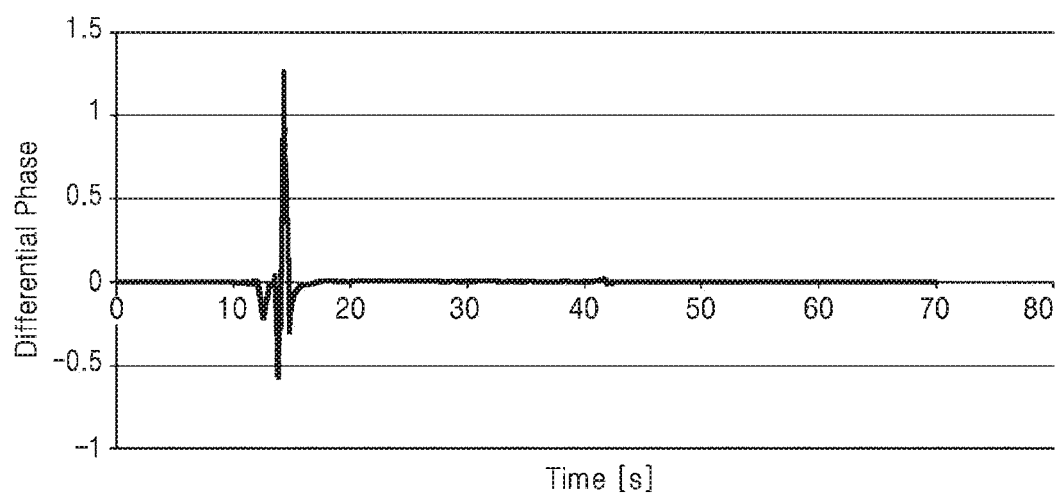
FIG. 35 illustrates a result of time differentiation with respect to a phase component according to an embodiment of the disclosure.

FIG. 35 illustrates a result of a time differentiation with respect to a phase component θ according to an embodiment of the disclosure.

Referring to FIGS. 34 and 35, the first threshold value processor 3114 determines whether the examinee has attached an earphone thereto, by performing threshold value processing with respect to the result of the time differentiation with respect to the amplitude component A of FIG. 34 and the result of the time differentiation with respect to the phase component θ of FIG. 35. Hereinafter, the amplitude component A having undergone time differentiation is referred to as a differential amplitude value, and the phase component θ having undergone time differentiation is referred to as a differential phase value.

Threshold value processing with respect to the differential amplitude value and the differential phase value will now be described with reference to FIGS. 36 and 37.

Figure 36:
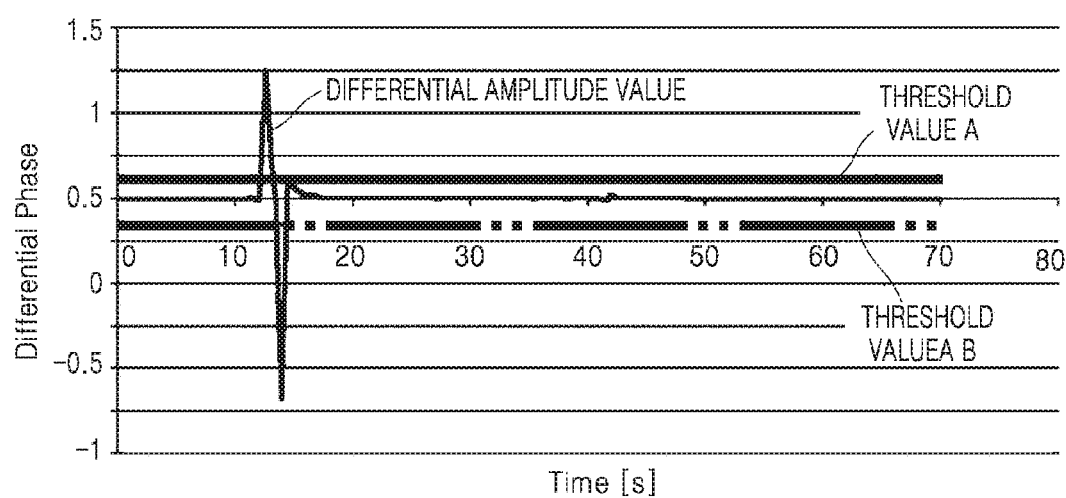
FIG. 36 is a graph illustrating a threshold value processing with respect to a differential amplitude value according to an embodiment of the disclosure.

FIG. 36 is a graph for illustrating a threshold value processing with respect to a differential amplitude value according to an embodiment of the disclosure.

Figure 37:
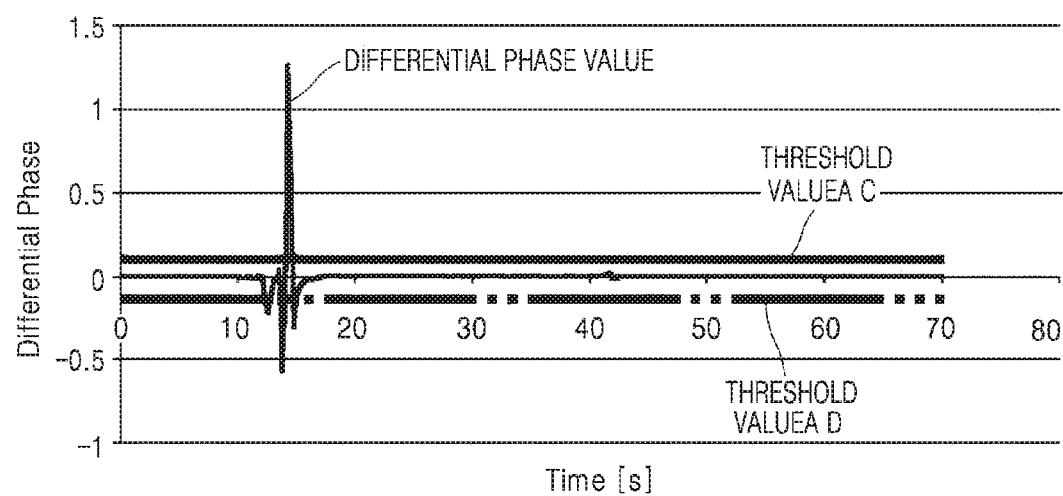
FIG. 37 is a graph illustrating a threshold value processing with respect to a differential phase value according to an embodiment of the disclosure.

FIG. 37 is a graph for illustrating a threshold value processing with respect to a differential phase value according to an embodiment of the disclosure.

Referring to FIG. 36, the first threshold value processor 3114 determines whether the examinee has attached the earphone 110 thereto, based on a comparison between the differential amplitude value and upper and lower threshold values A and B. The first threshold value processor 3114 sets up a flag when the differential amplitude value exceeds the upper threshold value A and then falls short of the lower threshold value B within a certain time period. When the differential amplitude value exceeds the upper threshold value A and then does not short of the lower threshold value B within the certain time period, information indicating that the differential amplitude value exceeded the upper threshold value A is reset. The certain time period may be, for example, about 0 to about 10 seconds.

Likewise, referring to FIG. 37, the first threshold value processor 3114 determines whether the examinee has attached the earphone 110 thereto, based on a comparison between the differential phase value and upper and lower threshold values C and D. The first threshold value processor 3114 sets up a flag when the differential phase value falls short of the lower threshold value D and then exceeds the upper threshold value C within a certain time period. When the differential phase value falls short of the lower threshold value D and then does not exceed the upper threshold value C within the certain time period, information indicating that the differential phase value fell short of the lower threshold value D is reset. The certain time period may be, for example, about 0 to about 10 seconds.

When flags are set up at both the differential amplitude value and the differential phase value, the first threshold value processor 3114 determines that the examinee has attached the earphone 110 thereto.

When a flag is set up at one of the differential amplitude value and the differential phase value and then a flag is not set up at the other within a certain time period, information indicating that a flag was set up is reset. The certain time period may be, for example, about 0 to about 10 seconds.

When a flag is set up at one of the differential amplitude value and the differential phase value, the first threshold value processor 3114 may determine that the examinee has attached the earphone 110 thereto. When the differential amplitude value exceeds the upper threshold value A, when the differential amplitude value falls short of the lower threshold value B, when the differential phase value falls short of the lower threshold value D, or when the differential phase value exceeds the upper threshold value C, the first threshold value processor 3114 may determine that the examinee has attached the earphone 110 thereto. In this case, even when the electronic device 100 does not perform threshold value processing with respect to all of the four upper and lower threshold values A, B, C, and D, the electronic device 100 may detect attachment of the earphone 110 to the examinee, and thus the time for the detection is short.

Then, detection of detachment of the earphone 110 from the examinee will be described.

In contrast with the detection of attachment of the earphone 110 to the examinee, detection of detachment of the earphone 110 from the examinee is performed with respect to the amplitude component A and the phase component θ according to a different algorithm Detection of detachment of the earphone 110 from the examinee based on the amplitude component A will be described first.

Figure 39:
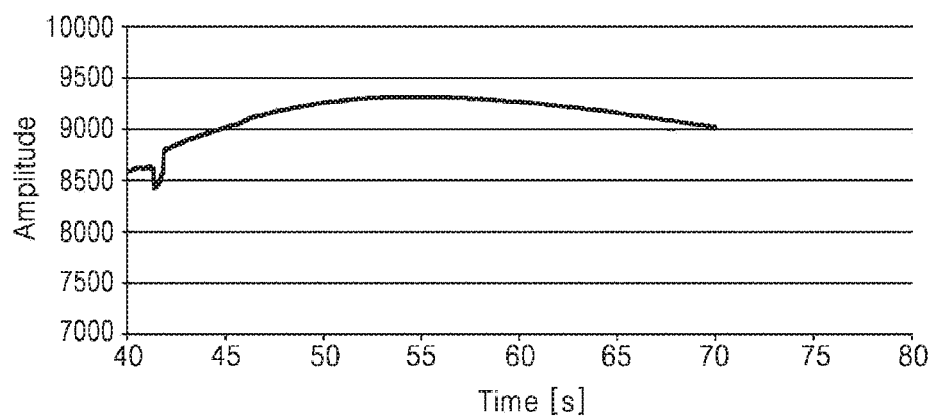
FIG. 39 illustrates a change, over time, in an amplitude component generated by a processor when an examinee has detached an earphone from his or her external auditory tube according to an embodiment of the disclosure.

FIG. 39 illustrates a change, over time, in an amplitude component A generated by a processor when an examinee has detached an earphone from his or her external auditory tube according to an embodiment of the disclosure.

Referring to FIG. 39, an amplitude is illustrated, and the horizontal axis thereof indicates time (second). In FIG. 39, the amplitude component A greatly changes at about 42 seconds. At this time, the examinee has separated or removed the earphone 110 from his or her external auditory tube. To more emphasize the change in the amplitude component A, the second differential value calculator 3812 performs time differentiation with respect to the amplitude component A. The time differentiation is already described above, and thus repeated descriptions thereof will be omitted.

Figure 40:
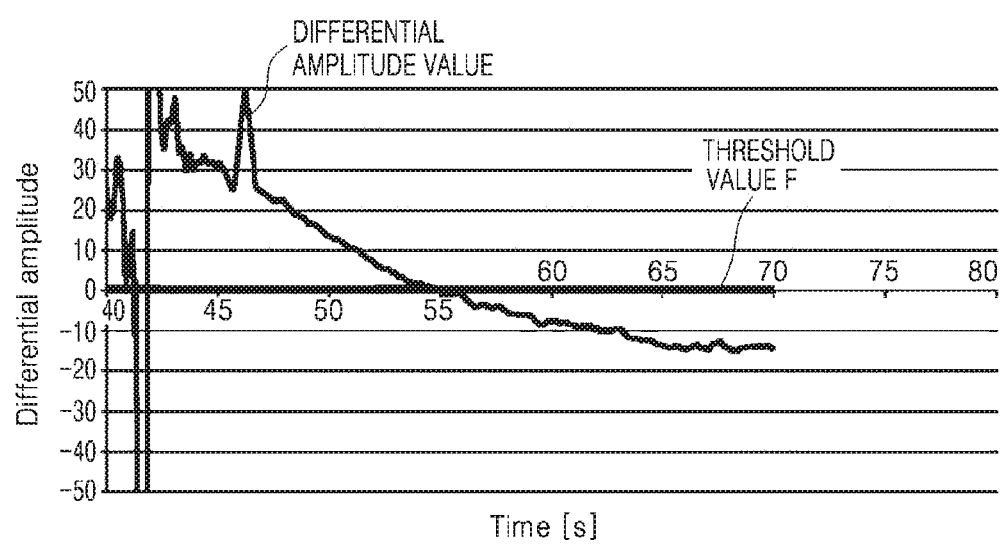
FIG. 40 illustrates a result of a time differentiation with respect to an amplitude component according to an embodiment of the disclosure.

FIG. 40 illustrates a result of the time differentiation with respect to an amplitude component A according to an embodiment of the disclosure.

Referring to FIG. 39, the amplitude of the amplitude component A starts decreasing.

Referring to FIG. 40, a differential amplitude value changes from a positive value to a negative value at about 55 seconds. When the decrease in the amplitude of the amplitude component A of FIG. 39 continues for a certain time period, the processor 140*f* may determine that the earphone 110 has been removed from the examinee. When the differential amplitude value continuously falls short of a threshold value F for a certain time period, the second threshold value processor 3814 determines that the earphone 110 has been removed from the examinee. According to an embodiment of the disclosure, in FIG. 40, the threshold value F may be 0, and the certain time period may be, for example, 0 to about 10 seconds.

Next, detection of detachment of the earphone 110 from the examinee based on the phase component θ will be described.

Figure 41:
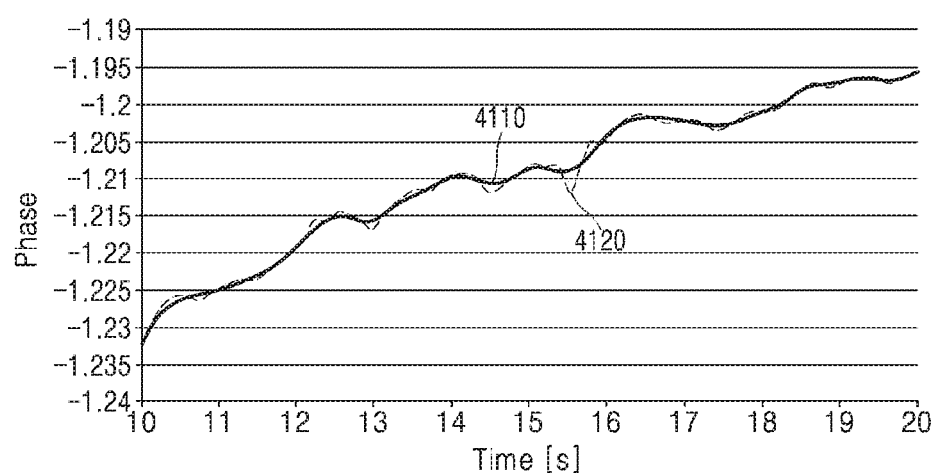
FIG. 41 illustrates a change, over time, in a phase component generated by a processor when an examinee has detached an earphone from his or her external auditory tube according to an embodiment of the disclosure.

FIG. 41 illustrates a change, over time, in a phase component θ generated by a processor when an examinee has detached an earphone from his or her external auditory tube according to an embodiment of the disclosure.

Referring to FIG. 41, a phase is illustrated, and the horizontal axis thereof indicates time (second).

Referring to FIG. 41, a broken line 4120 indicates a phase value, and gently goes up over time. Because it is difficult to extract a height of a wave of a waveform, namely, an AC component, the phase component θ that gently changes as described above, the moving average processor 3816 performs moving averaging with respect to the phase component θ. A solid line 4110 of FIG. 41 indicates a result of moving averaging of 5 points executed 20 times with respect to the phase value indicated by the broken line 4120. As shown in the solid line 4110 of FIG. 41, by perform moving averaging with respect to the phase component θ, an AC component may be removed from the phase component θ. Accordingly, the moving average processor 3816 calculates a differential value by subtracting a value indicated by the solid line 4110 from the phase value indicated by the broken line 4120, thereby extracting an AC component from the phase component θ.

Figure 42:
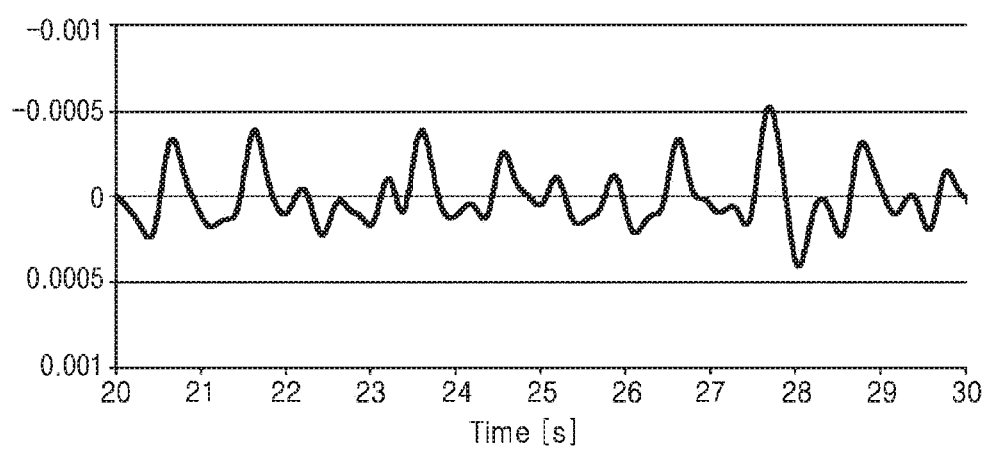
FIG. 42 illustrates an alternating current (AC) component of a phase component when an examinee wears an earphone according to an embodiment of the disclosure.

FIG. 42 illustrates an AC component of a phase component θ when an examinee wears an earphone according to an embodiment of the disclosure.

Figure 43:
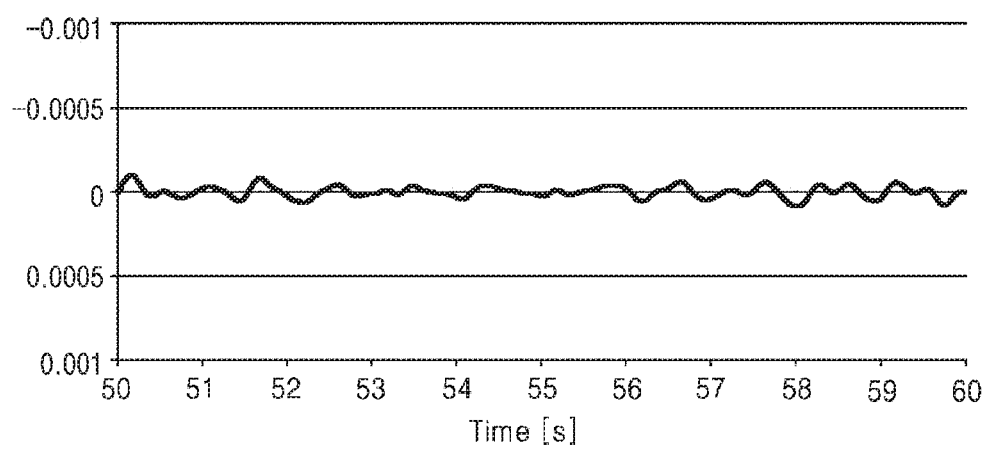
FIG. 43 illustrates an AC component of a phase component when an examinee does not wear an earphone according to an embodiment of the disclosure.

FIG. 43 illustrates an AC component of a phase component θ when an examinee does not wear an earphone according to an embodiment of the disclosure.

Referring to FIGS. 42 and 43, the waves of the phase components θ have different heights. In other words, the AC component of the phase component θ of FIG. 42 when the examinee wears the earphone 110 includes a variation originating from a pulse, and the AC component of the phase component θ of FIG. 43 when the examinee does not wear the earphone 110 does not include a variation originating from a pulse. Accordingly, to compare the AC components of FIGS. 42 and 43 with each other, the wave height digitizer 3818 digitizes the heights of the waves of the AC components of FIGS. 42 and 43.

The wave height digitizer 3818 digitizes the heights of the waves of the AC components of FIGS. 42 and 43 by calculating a differential value between the heights of a convex peak and a concave portion of the waveforms of the AC components of FIGS. 42 and 43. The wave height digitizer 3818 may calculate a differential value between an average value of the heights of concave peaks before and after a convex peak and the height of the convex peak, or may calculate a differential value between the height of one of the concave peaks before and after the convex peak and the height of the convex peak.

Figure 44:
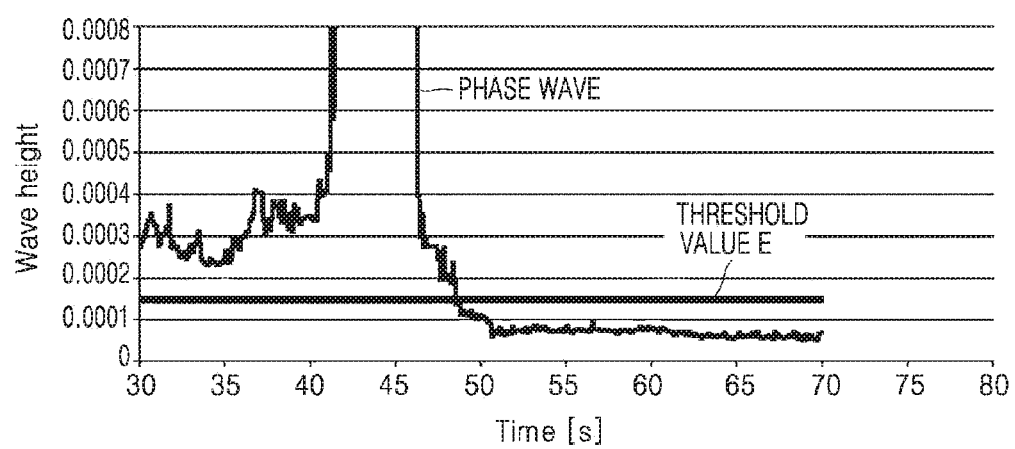
FIG. 44 illustrates a digitized wave height of an AC component of the phase component according to an embodiment of the disclosure.

FIG. 44 illustrates a digitized wave height of an AC component of a phase component θ according to an embodiment of the disclosure.

Referring to FIG. 44, the vertical axis indicates a digitized wave height, and the horizontal axis thereof indicates time (second). In FIG. 44, the examinee wears the earphone 110 between 30 seconds and 40 seconds, the examinee removes the earphone 110 between 40 seconds and 46 seconds, and the earphone 110 has been detached from the examinee after 46 seconds.

Referring to FIG. 44, the digitized wave height of the AC component of the phase component θ clearly differs when the examinee wears the earphone 110 (30 seconds to 40 seconds) and when the examinee takes off the earphone 110 (after 46 seconds). Accordingly, the third threshold value processor 3820 determines that the earphone 110 was removed from the examinee, when the digitized wave height of the AC component of the phase component θ falls short of a threshold value E.

As described above, in contrast with the detection of attachment of the earphone 110 to the examinee, the detection of detachment of the earphone 110 from the examinee is performed with respect to the amplitude component A and the phase component θ according to a different algorithm. Accordingly, the processor 140ƒ according to another embodiment of the disclosure may determine that the earphone 110 was separated from the examinee, based on the amplitude component A or the phase component θ. The processor 140ƒ according to another embodiment of the disclosure may determine that the earphone 110 was separated from the examinee, when separation of the earphone 110 from the examinee is detected from both the amplitude component A or the phase component θ.

In the electronic devices 100 employing the above-described processors 140e and 140ƒ, the same effects as those of the electronic devices 100 according to the previous embodiments may be obtained, and attachment of the earphone 110 to the examinee and detachment of the earphone 110 from the examinee may be detected based on at least one of the amplitude component A calculated from the in-phase component I by the amplitude calculator 512 or the phase component θ calculated from the quadrature phase component Q by the phase calculator 532. Accordingly, even when a proximity sensor or the like is not embedded in the earphone 110, attachment or detachment of the earphone 110 to or from the examinee may be detected. Thus, the electronic device 100 according to another embodiment of the disclosure may perform attachment or detachment of the earphone 110 to or from the examinee at low cost, may save the internal space of the earphone 110 by not including a special sensor, and may not increase power consumption. For example, when a battery is embedded in the earphone 110, such as a wireless earphone 110, attachment or detachment of the earphone 110 to or from the examinee is performed by a proximity sensor, and the battery is turned on/off. However, the electronic device 100 according to the embodiment may turn a battery on/off without including a proximity sensor.

Embodiments of the disclosure are not limited to the above-described embodiments, and suitable modifications may be made thereto without departing from the spirit of the disclosure. For example, in the embodiments of FIGS. 4, 11, 13, 15, 16, 18, 21, 23, and 24, the DACs 410, 1120, and 1122 and the ADC 416 are used. However, when the signal generator 130 and the orthogonal demodulator 420 are formed as analog circuits, the DACs 410, 1120, and 1122 and the ADC 416 may be omitted. Similarly, also in the embodiment of FIG. 14, when the signal generator 130 is formed as an analog circuit, the DAC 410 may be omitted.

According to embodiments of the disclosure, an example where a pulse and a body temperature are mainly detected as biometric information is illustrated. However, the biometric information detected by the electronic devices 100 according to embodiments of the disclosure are not limited to a pulse and a body temperature.

Moreover, according to embodiments of the disclosure, the electronic device 100 may be a wired earphone type or wireless earphone type electronic device.

Figure 45:
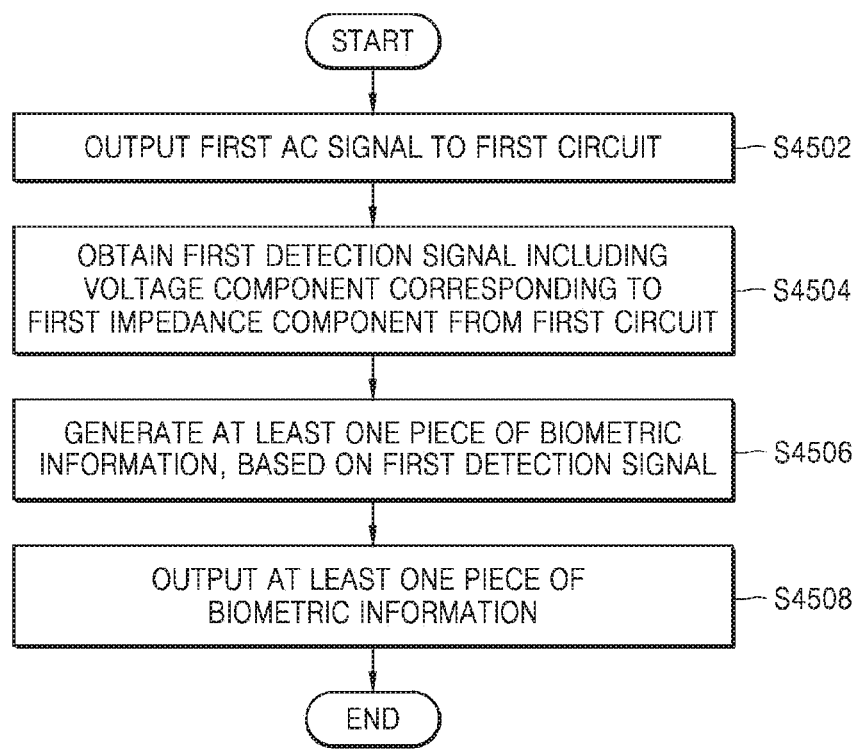
FIG. 45 is a flowchart of a method of controlling an electronic device according to an embodiment of the disclosure.

FIG. 45 is a flowchart of a method of controlling an electronic device according to an embodiment of the disclosure.

Referring to FIG. 45, the operations included in an electronic device controlling method according to the disclosure may be performed by various types of electronic devices including an earphone, a first circuit, and a processor. An embodiment in which an electronic device controlling method is performed by the electronic devices 100 according to embodiments of the disclosure will now be focused on and described. Thus, the embodiments described above regarding the electronic devices 100 are applicable to embodiments of an electronic device controlling method, and, inversely, the embodiments described above regarding the electronic device controlling method are applicable to the embodiments for the electronic devices 100 Electronic device controlling methods according to disclosed embodiments are performed by the above-described electronic devices 100, but embodiments are not limited thereto. The electronic device controlling methods according to embodiments may be performed by various types of electronic devices.

In operation S4502, the electronic device 100 outputs a first AC signal to a first circuit. The processor 140 of the electronic device 100 may control the signal generator 130 to output the first AC signal to the first circuit.

In operation S4504, the electronic device 100 obtains a first detection signal including a voltage component corresponding to a first impedance component from the first circuit. The processor 140 may obtain the first detection signal from an output terminal of the first circuit. The first circuit may perform analog-to-digital conversion with respect to a voltage detected by an analog circuit and outputs a result of the analog-to-digital conversion to the processor 140. According to an embodiment of the disclosure, the first detection signal may include an in-phase component signal I and a quadrature phase component signal Q. According to another embodiment of the disclosure, the first detection signal may include an amplitude component signal A and a DC component signal DC.

Next, in operation S4506, the electronic device 100 generates at least one piece of biometric information, based on the first detection signal. The at least one piece of biometric information may include at least one of heart rate information or body temperature information, or a combination thereof. The processor 140 may obtain amplitude information and phase information from the first detection signal, calculate the body temperature information from the amplitude information, and calculate the heart rate information from the phase information.

According to an embodiment of the disclosure, the processor 140 may include an operation of correcting a motion of a user, in an operation of calculating the heart rate information. The processor 140 may calculate an average value of a differential value from which a DC component has been removed from the amplitude information and an average value of a differential value from which a DC component has been removed from the phase information, and may generate, from the average values, the signal Cd from which a motion component has been removed. The operation of correcting the motion is similar to that in the embodiments of FIGS. 23 and 24, and thus a repeated description thereof will be omitted.

According to an embodiment of the disclosure, the processor 140 may include an operation of detecting attachment or detachment of an earphone from the first detection signal. The operation of detecting attachment or detachment of an earphone is similar to that in the embodiments of FIGS. 31 through 44, and thus a repeated description thereof will be omitted.

Next, in operation S4508, the electronic device 100 outputs at least one piece of biometric information. The electronic device 100 may output the at least one piece of biometric information to an external apparatus via a communication interface, or display the at least one piece of biometric information via a display, or output the at least one piece of biometric information as a sound via an earphone or the like.

Figure 46:
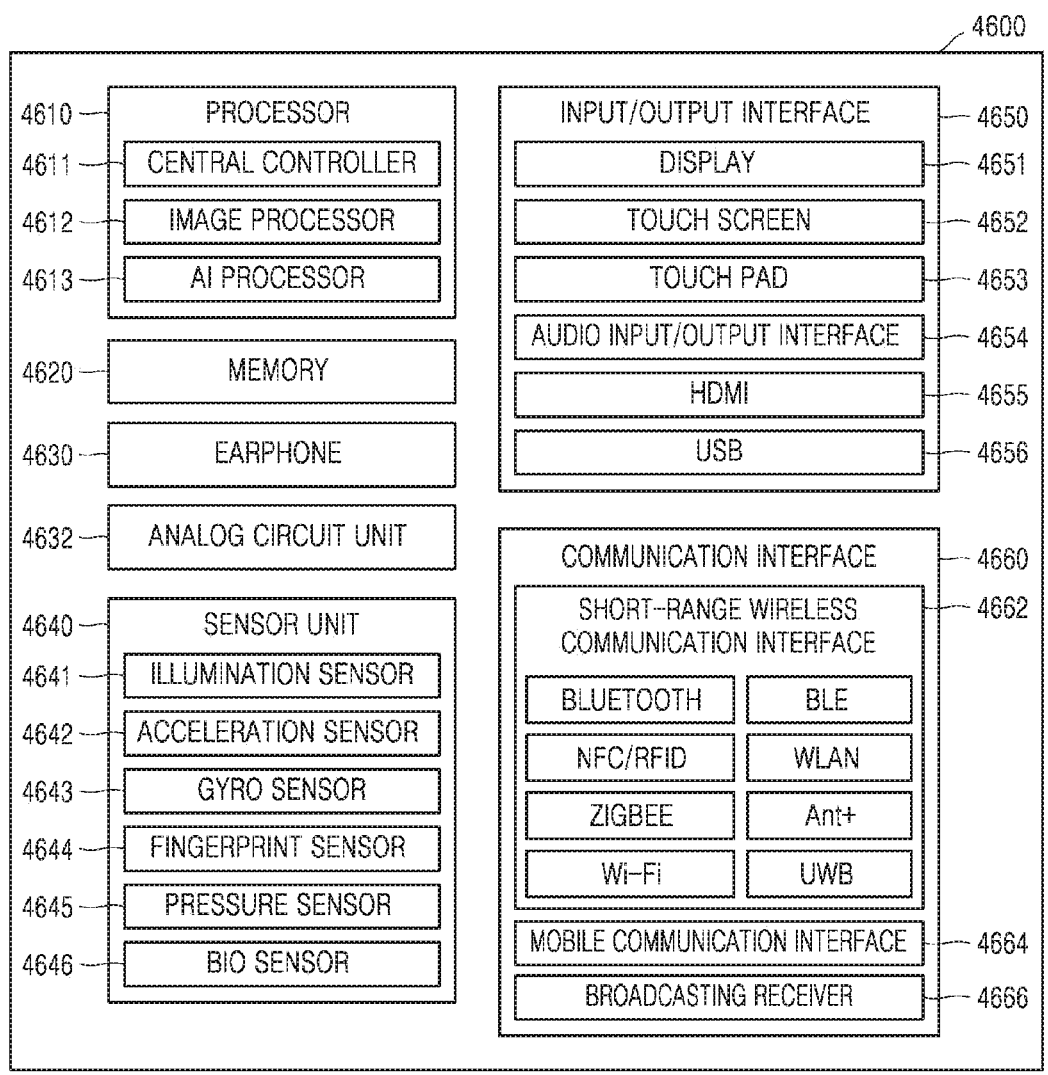
FIG. 46 is a block diagram of an electronic device according to an embodiment of the disclosure.

FIG. 46 is a block diagram of an electronic device according to an embodiment of the disclosure.

The electronic device 100 may be implemented in various types.

Referring to FIG. 46, an electronic device 4600 is illustrated according to an embodiment of the disclosure. The electronic device 4600 includes a processor 4610, a memory 4620, an earphone 4630, an analog circuit unit 4632, a sensor unit 4640, an input/output interface 4650, and a communication interface 4660. The earphone 110 of the electronic device 100 may correspond to the earphone 4630 of the electronic device 4600, the first circuit 120 and the signal generator 130 of the electronic device 100 may correspond to the analog circuit unit 4632 of the electronic device 4600, and the processor 140 of the electronic device 100 may correspond to the processor 4610 of the electronic device 4600.

The processor 4610 may include at least one processor. The processor 4610 may include dedicated processors, such as a central controller 4611, an image processor 4612, and an artificial intelligence (AI) processor 4613.

The memory 4620 may include a volatile storage medium, a non-volatile storage medium, or a combination thereof. The memory 4620 may include various types of memories, such as a main memory, a cache memory, a register, and a non-volatile memory. The memory 4620 may be implemented as any of various types of storage media. For example, the memory 4620 may include at least one type of storage medium selected from among a flash memory type, a hard disk type, a multimedia card micro type, a card type memory (for example, a secure digital (SD) or extreme digital (XD) memory), a random access memory (RAM), a static random access memory (SRAM), a read-only memory (ROM), an electrically erasable programmable ROM (EEPROM), a programmable ROM (PROM), magnetic memory, a magnetic disk, and an optical disk.

The earphone 4630 transforms an electrical signal into a sound wave signal and outputs the sound wave signal. The earphone 4630 may transform the electrical signal into the sound wave signal by operating a vibration plate.

The analog circuit unit 4632 generates, transmits, or processes an analog signal. The analog circuit unit 4632 may include at least one analog device, for example, an analog device, such as a resistor, a capacitor, or an inductor. The analog circuit unit 4632 may be implemented as a PCB, an FPCB, or an application specific integrated circuit (ASIC). The analog circuit unit 4632 may generate, transmit, or process a data signal, a control signal, a power signal, or the like.

The sensor unit 4640 may include various types of sensors. The sensor unit 4640 may include, for example, an illumination sensor 4641, an acceleration sensor 4642, a gyro sensor 4643, a fingerprint sensor 4644, a pressure sensor 4645, or a bio sensor 4646, or a combination thereof. A signal detected by the sensor unit 4640 may be input to the processor 4610, and the processor 4610 may perform, based on the signal output by the sensor unit 4640, a process, such as display brightness control, camera brightness control, motion detection, device orientation detection, fingerprint recognition, bio-signal detection and processing, and biometric authentication.

The input/output interface 4650 may include various types of input/output interfaces. The input/output interface 4650 may include, for example, a display 4651, a touch screen 4652, a touch pad 4653, an audio input/output interface 4654, an HDMI 4655, or a USB 4656, or a combination thereof. The communication interface 4660 may include various types of communication modules. The input/output interface 4650 may include various types of input/output components. The processor 4610 may perform gesture recognition, voice recognition, and the like, based on a signal received from the input/output interface 4650.

The communication interface 4660 may include at least one of a short-range wireless communication interface 4662, a mobile communication interface 4664, or a broadcasting receiver 4666, or a combination thereof. The short-range wireless communication interface 4662 may perform Bluetooth, Bluetooth Low Energy (BLE), Near Field Communication, Radio Frequency Identification (RFID), WLAN (Wi-Fi), Zigbee, infrared Data Association (IrDA) communication, Wi-Fi Direct (WFD), ultra wideband (UWB), Ant+ communication, or a combination thereof. The electronic device 4600 may communicate with various types of external apparatuses via the communication interface 4660. The electronic device 4600 may communicate with, for example, a server, another mobile device, a wearable device, another PC, or the like via the communication interface 4660, and thus may exchange data and a control signal.

The disclosed embodiments may be implemented as an S/W program including instructions stored in computer-readable storage media. In addition, the disclosed embodiments may be embodied in a computer readable storage medium storing a computer program.

A computer is a device capable of calling stored instructions from a storage medium and operating according to the disclosed embodiments according to the called instructions, and may include the electronic devices according to the disclosed embodiments.

The computer-readable storage medium may be provided as a non-transitory storage medium. Here, 'non-transitory' means that the storage medium does not include a signal and is tangible, but does not include distinguish whether data is stored semi-permanently or temporarily in the storage medium.

In addition, electronic devices and operation methods thereof according to the disclosed embodiments may be provided in a computer program product. The computer program product may be traded as a commodity between a seller and a purchaser.

The computer program product may include a software program and a computer-readable storage medium having the software program stored thereon. For example, the computer program product may include a product in the form of a software program (e.g., a downloadable app) that is electronically distributed through the manufacturer of an electronic device or an electronic market (e.g., Google Play Store, AppStore). For electronic distribution, at least a portion of the software program may be stored on a storage medium or may be created temporarily. In this case, the storage medium may be a server of a manufacturer, a server of an electronic market, or a storage medium of a relay server for temporarily storing an SW program.

The computer program product may include a storage medium of a server or a storage medium of a terminal in a system composed of a server and a terminal (e.g., an electronic device, a portable electronic device, a wearable device, and the like). Alternatively, when there is a third device (e.g., a smartphone) in communication with the server or terminal, the computer program product may include a storage medium of the third device. Alternatively, the computer program product may include the S/W program itself transmitted from the server to the terminal or the third device, or transmitted from the third device to the terminal.

In this case, one of the server, the terminal, and the third device may execute the computer program product to perform the methods according to the disclosed embodiments. Alternatively, at least two of the server, the terminal, and the third device may execute the computer program product to distribute and perform the methods according to the disclosed embodiments.

For example, a server (e.g., a cloud server or an AI server) may execute a computer program product stored on a server to control a terminal communicating with the server to perform the methods according to the disclosed embodiments.

As another example, a third device may execute a computer program product to control a terminal in communication with the third device to perform the methods according to the disclosed embodiments. For example, the third device may control an electronic device to perform an electronic device controlling method.

When the third device executes the computer program product, the third device may download the computer program product from the server and execute the downloaded computer program product. Alternatively, the third device may execute a computer program product provided in a preloaded state to perform methods according to the disclosed embodiments.

According to embodiments of the disclosure, provided is a device and a method of obtaining biometric information by using an earphone, so that a user is able to obtain the biometric information without performing a special action for obtaining the biometric information.

According to embodiments of the disclosure, provided is a device and a method of obtaining biometric information by using an earphone while outputting audio through the earphone.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
an earphone including a first impedance component;
a signal generator configured to output a first alternating current (AC) signal;
a first circuit including at least one first analog device having an impedance component electrically coupled to the first impedance component, and configured to receive the first AC signal and output a first detection signal including a voltage component corresponding to the first impedance component; and
at least one processor configured to:
generate at least one piece of biometric information, based on the first detection signal, and
output the at least one piece of biometric information.

2. The electronic device of claim 1,
wherein the electronic device includes a shape in which the earphone is inserted into an external auditory meatus of a human being, and
wherein a magnitude of the first impedance component varies according to a change in a pressure of the external auditory meatus.

3. The electronic device of claim 1,
wherein the at least one piece of biometric information comprises heart rate information, and
wherein the at least one processor is further configured to generate the heart rate information, based on a phase component of the first detection signal.

4. The electronic device of claim 1,
wherein the at least one piece of biometric information comprises body temperature information, and
wherein the at least one processor is further configured to generate the body temperature information, based on an amplitude component of the first detection signal.

5. The electronic device of claim 1, wherein the first AC signal includes a frequency in an ultrasonic range.

6. The electronic device of claim 1, wherein the first AC signal includes a frequency of 20 kHz to 40 kHz.

7. The electronic device of claim 1, wherein the first circuit is configured to:
generate the first detection signal including an in-phase signal of an in-phase component and an orthogonal signal of a quadrature phase component from the first AC signal and an intermediate detection signal of a node connected to the first analog device, and
output the first detection signal to the at least one processor.

8. The electronic device of claim 7, wherein the at least one processor is further configured to:
generate body temperature information, based on a sum of a square of the in-phase signal and a square of the orthogonal signal, and
generate heart rate information, based on phase information extracted from the in-phase signal and the orthogonal signal.

9. The electronic device of claim 1, wherein the first circuit comprises a second impedance device, a third impedance device, and a fourth impedance device connected with the first impedance component in a bridge circuit structure, and is configured to:
receive the first AC signal via at least one of a first node or a second node of the bridge circuit structure or a combination thereof,
generate an in-phase signal of an in-phase component and an orthogonal signal of a quadrature phase component from an intermediate detection signal of a third node of the bridge circuit structure, and
output the in-phase signal and the orthogonal signal to the at least one processor.

10. The electronic device of claim 9,
wherein two impedance devices directly connected to the first node have identical impedance values, and
wherein two impedance devices directly connected to the second node have identical impedance values.

11. The electronic device of claim 9,
wherein the first node receives the first AC signal,
wherein the second node receives a signal obtained by delaying a phase of the first AC signal by 180°,
wherein the first impedance component is connected between a fourth node and the first node, and
wherein the fourth node is connected to ground potential.

12. The electronic device of claim 9,
wherein the first node receives the first AC signal,
wherein the second node is connected to ground potential,
wherein the first impedance component is connected to between the second node and a fourth node, and
wherein the first circuit is configured to differentially amplify a signal of the fourth node and a signal of the third node to generate the first detection signal.

13. The electronic device of claim 9,
wherein the first impedance component is connected to between the second node and a fourth node,
wherein the second impedance device is connected to between the first node and the fourth node, the third impedance device is connected to between the first node and the third node, and the fourth impedance device is connected to between the second node and the third node,
wherein the earphone includes a first resistance component and a first inductance component,
wherein the second impedance device comprises a second resistor, the third impedance device comprises a third resistor and a third capacitor connected to the third resistor in parallel, and the fourth impedance device comprises a fourth resistor,
wherein the first resistance component and a resistance component of the fourth resistor include same magnitudes,
wherein the second resistor and the third resistor include resistance components of which magnitudes are same, and
wherein the third capacitor includes a capacitor component of a magnitude {first inductance component/(resistance component of third resistor*resistance component of fourth resistor)}.

14. The electronic device of claim 9,
wherein the first impedance component is connected between the second node and a fourth node,
wherein the second impedance device is connected between the first node and the fourth node, the third impedance device is connected between the first node and the third node, and the fourth impedance device is connected between the second node and the third node,
wherein the first impedance component includes a first first resistance component and a first inductance component serially connected to each other between the second node and the fourth node, and a second first resistance component connected to the first first resistance component and the first inductance component in parallel between the second node and the fourth node,
wherein the second impedance device comprises a second resistor,
wherein the third impedance device comprises a third resistor and a third capacitor connected to each other in parallel between the first node and the third node, and
wherein the fourth impedance device comprises a first fourth resistor, a second fourth resistor, and a fourth capacitor connected to one another in parallel between the second node and the third node.

15. The electronic device of claim 14,
wherein the first first resistance component and a resistance component of the first fourth resistor include same magnitudes,
wherein the second resistor and the third resistor include resistance components of which magnitudes are same,
wherein the second first resistance component and a resistance component of the second fourth resistor include same magnitudes, and
wherein the third capacitor includes a capacitor component of a magnitude {first inductance component/(resistance component of third resistor*resistance component of first fourth resistor)}.

16. The electronic device of claim 1,
wherein the first circuit comprises a band pass filter and an envelope detector, and is configured to:
generate a second intermediate detection signal by modulating a first intermediate detection signal of a node connected to the first analog device by using the band pass filter and the envelope detector, and
generate the first detection signal including an amplitude change component signal and a direct current (DC) component signal generated from the second intermediate detection signal, and wherein the at least one processor is further configured to:
generate heart rate information from the amplitude change component signal, and
generate body temperature information from the DC component signal.

17. The electronic device of claim 1, wherein the first circuit is configured to:
receive an electrical audio signal corresponding to an audio signal output via the earphone,
process the electrical audio signal by using a high pass filter, and
apply a result of the processing to at least one node of the first circuit.

18. The electronic device of claim 1,
wherein the first circuit is configured to generate the first detection signal including an in-phase signal of an in-phase component and an orthogonal signal of a quadrature phase component from the first AC signal and an intermediate detection signal of a node connected to the first analog device, and
wherein the at least one processor is further configured to:
generate an amplitude signal of an amplitude component and a phase signal of a phase component from the in-phase signal and the orthogonal signal, and
remove a motion component of the electronic device by using the amplitude signal and the phase signal.

19. The electronic device of claim 1,
wherein the first circuit is configured to generate the first detection signal including an in-phase signal of an in-phase component and an orthogonal signal of a quadrature phase component from the first AC signal and an intermediate detection signal of a node connected to the first analog device, and
wherein the at least one processor is further configured to:
generate an amplitude signal of an amplitude component and a phase signal of a phase component from the in-phase signal and the orthogonal signal, and
detect attachment or detachment of the electronic device, based on a variation in at least one of the amplitude signal or the phase signal.

20. A method of controlling an electronic device comprising an earphone including a first impedance component, and a first circuit including at least one first analog device including an impedance component electrically coupled to the first impedance component, the method comprising:
controlling a first AC signal to be output to the first circuit;
obtaining a first detection signal including a voltage component corresponding to the first impedance component from the first circuit;
generating at least one piece of biometric information, based on the first detection signal; and
outputting the at least one piece of biometric information.

* * * * *